(12) United States Patent
Lambert et al.

(10) Patent No.: US 10,976,324 B2
(45) Date of Patent: Apr. 13, 2021

(54) SYNERGISTIC COMBINATION OF BIOMARKERS FOR DETECTING AND ASSESSING HEPATIC FIBROSIS

(71) Applicants: BIO-RAD INNOVATIONS, Marnes la Coquette (FR); ASSISTANCE PUBLIQUE—HOPITAUX DE PARIS, Paris (FR); CENTRE NATIONAL DE LA RECHERCHE SCIENTIFIQUE, Paris (FR); UNIVERSITE PARIS DIDEROT—PARIS 7, Paris (FR)

(72) Inventors: Nadine Lambert, Chatou (FR); Benedicte Watelet, Saint Clement de Riviere (FR); Isabelle Catherine Batxelli, Aigues-Vives (FR); Tarik Asselah, Paris (FR)

( * ) Notice: Subject to any disclaimer, the term of this patent is extended or adjusted under 35 U.S.C. 154(b) by 748 days.

(21) Appl. No.: 15/320,862

(22) PCT Filed: Jun. 9, 2015

(86) PCT No.: PCT/FR2015/051518
§ 371 (c)(1),
(2) Date: Dec. 21, 2016

(87) PCT Pub. No.: WO2015/197934
PCT Pub. Date: Dec. 30, 2015

(65) Prior Publication Data
US 2017/0160289 A1 Jun. 8, 2017

(30) Foreign Application Priority Data
Jun. 27, 2014 (FR) .................................. 1456037

(51) Int. Cl.
*G01N 33/68* (2006.01)
*G16B 40/00* (2019.01)

(52) U.S. Cl.
CPC ......... *G01N 33/6893* (2013.01); *G16B 40/00* (2019.02); *G01N 2800/085* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 6,631,330 B1 | 10/2003 | Poynard | |
| 7,824,871 B2 | 11/2010 | Younossi et al. | |
| 9,624,541 B2 | 4/2017 | Watelet et al. | |
| 10,435,744 B2 | 10/2019 | Watelet et al. | |
| 2007/0172907 A1 | 7/2007 | Volker et al. | |
| 2008/0161203 A1 | 7/2008 | Su et al. | |
| 2010/0041069 A1 | 2/2010 | Lederkremer | |
| 2010/0136579 A1 | 6/2010 | Tseng et al. | |
| 2010/0203553 A1 | 8/2010 | Abdeen et al. | |
| 2011/0014126 A1 | 1/2011 | Evans et al. | |
| 2013/0316332 A1 | 11/2013 | Bieche et al. | |
| 2013/0323720 A1* | 12/2013 | Watelet | C12Q 1/6876 435/5 |
| 2017/0160289 A1 | 6/2017 | Lambert et al. | |
| 2020/0056235 A1 | 2/2020 | Watelet et al. | |
| 2020/0249242 A1 | 8/2020 | Batxelli-Molina et al. | |

FOREIGN PATENT DOCUMENTS

| | | |
|---|---|---|
| WO | WO 02/16949 | 2/2002 |
| WO | WO 2006/082522 | 8/2006 |
| WO | WO 2006/103570 | 10/2006 |
| WO | WO 2007/072290 | 6/2007 |
| WO | WO 2012/107528 | 8/2012 |
| WO | WO 2012/107530 | 8/2012 |
| WO | WO 2019/018610 | 1/2019 |

OTHER PUBLICATIONS

Seidler, Sebastian, et al. "Elevated circulating soluble interleukin-2 receptor in patients with chronic liver diseases is associated with non-classical monocytes." BMC gastroenterology 12.1 (2012): 38.*
EBioscience, FlowCytomix(TM) Multiple Analyte Detection User Guide, downloaded Aug. 2, 2020 from (http://www.inmunobiomedica.cl/docs/Flowcytomix-multiple-analyte-detection.pdf).*
Baker, Monya. "Blame it on the antibodies." Nature 521.7552 (2015): 274.*
Berglund, Lisa, et al. "A genecentric Human Protein Atlas for expression profiles based on antibodies." Molecular & cellular proteomics 7.10 (2008): 2019-2027.*
Egelhofer, Thea A., et al. "An assessment of histone-modification antibody quality." Nature structural & molecular biology 18.1 (2011): 91.*
Abe, T. et al. "CD44 Participates in IP-10 Induction in Cells in Which Hepatitis C Virus RNA is Replicating, through an Interaction with Toll-Like Receptor 2 and Hyaluronan" Journal of Virology, Jun. 2012, pp. 6159-6170, vol. 86, No. 11.
Mak, T.-M. et al. "Liver Fibrosis Assessment Using Transient Elastography Guided With Real-Time B-Mode Ultrasound Imaging: A Feasibility Study" *Ultrasound in Med. & Biol.*, 2013, pp. 956-966, vol. 39, No. 6.
Micheloud, D. et al. "Serum Levels of Fibrosis Progression Biomarkers Measured Early After LT are Associated to Severe HCV Recurrence" *Hepatology*, Oct. 2007, p. 476A, AASID Abstract #536, vol. 46, No. 4.

(Continued)

*Primary Examiner* — G Steven Vanni
(74) *Attorney, Agent, or Firm* — Saliwanchik, Lloyd & Eisenschenk

(57) ABSTRACT

The application relates to hepatic fibrosis, specifically to hepatic fibrosis that may appear in a patient infected with one or more hepatitis viruses and/or who is suffering from hepatitis, specifically chronic hepatitis. The application provides methods and means for determining the stage (or degree) of hepatic fibrosis of such a patient. Specifically, the methods and means of the application make it possible to determine whether or not the stage (or degree) of hepatic fibrosis of the patient has exceeded the stage of light fibrosis. The methods and means of the invention use a combination of biomarkers such as, in particular, the CXCL10 protein and hyaluronic acid (HA).

9 Claims, 11 Drawing Sheets
Specification includes a Sequence Listing.

(56) References Cited

OTHER PUBLICATIONS

Patel, K. et al. "Multiplex Protein Analysis to Determine Fibrosis Stage and Progression in Patients With Chronic Hepatitis C" *Clinical Gastroenterology and Hepatology*, 2014, pp. 2113-2120 and 2120e1-2120e3, vol. 12, No. 12.

El Raziky, M. et al. "A Novel Prediction Model for Liver Fibrosis in Patients With Chronic Hepatitis C Virus Using Fibroscan and Routine Laboratory Data" *Journal of Hepatology*, 2013, Poster #450, p. S184, vol. 58.

Wu, Y.-M. et al. "A simple noninvasive index to predict significant liver fibrosis in patients with advanced schistosomiasis japonica" *Parasitology International*, 2013, pp. 283-288, vol. 62.

Written Opinion in International Application No. PCT/FR2015/051518, dated Aug. 14, 2015, pp. 1-8.

Written Opinion in International Application No. PCT/US2018/042836, dated Sep. 19, 2018, pp. 1-10.

Claims pending in U.S. Appl. No. 16/632,404, filed Jan. 20, 2020, pp. 1-16.

Shin, et al. "SPP1 polymorphisms associated with HBV clearance and HCC occurrence" *International Journal of Epidemiology*, Oct. 2007, pp. 1001-1008, vol. 36, No. 5.

Schmilovitz-Weiss, H. et al. "Serum globulin levels in predicting the extent of hepatic fibrosis in patients with recurrent post-transplant hepatitis C infection" *Clinical Transplantation*, May 2007, pp. 391-397, vol. 21, No. 3.

Castera, et al. "Prospective Comparison of Transient Elastography, Fibrotest, APRI, and Liver Biopsy for the Assessment of Fibrosis in Chronic Hepatitis C" *Gastroenterology*, 2005, pp. 343-350, vol. 128.

Shaheen, et al. "FibroTest and FibroScan for the Prediction of Hepatitis C-Related Fibrosis: A Systematic Review of Diagnostic Test Accuracy" *American Journal of Gastroenterology*, 2007, pp. 2589-2600, vol. 102.

Asselah, et al. "Liver gene expression signature to predict response to pegylated interferon plus ribavirin combination therapy in patients with chronic hepatitis C" *Gut*, 2008, pp. 516-524, vol. 57.

Asselah, et al. "Liver Gene Expression Signature of Mild Fibrosis in Patients With Chronic Hepatitis C" *Gastroenterology*, 2005, pp. 2064-2075, vol. 129.

Bieche, et al. "Molecular profiling of early stage liver fibrosis in patients with chronic hepatitis C virus infection" *Virology*, 2005, pp. 130-144, vol. 332.

Chen, et al. "Cell-Type Specific Gene Expression Signature in Liver Underlies Response to Interferon Therapy in Chronic Hepatitis C Infection" *Gastroenterology*, 2010, pp. 1123-1133, vol. 138.

Huang, et al. "Plasma osteopontin concentration correlates with the severity of hepatic fibrosis and inflammation in HCV-infected subjects" *Clinica Chimica Acta*, 2010, pp. 675-678, vol. 411.

Patouraux, et al. "The Osteopontin Level in Liver, Adipose Tissue and Serum is Correlated with Fibrosis in Patients with Alcoholic Liver Disease" *PloS ONE*, Apr. 2012, pp. 1-10, vol. 7, No. 4, e35612.

International Search Report for PCT/EP2012/052234 dated Jun. 25, 2012.

Written Opinion of the International Searching Authority for PCT/EP2012/052234 dated Jun. 25, 2012.

Gene List, "Human Genome CGH Microarray 44B G4410B" *Agilent Technologies*, 2007.

Ducés, A. et al. "Liver Gene Expression Signature of Mild Fibrosis in Chronic Hepatitis C" *Gastroenterology*, May 2010, p. S-837, vol. 138, No. 5, Supplement 1, Abstract No. T1958.

Ducés, A. et al. "Liver Gene Expression Signature to Predict Response to Pegylated Interferon Plus Ribavirin in Chronic Hepatitis C" *Gastroenterology*, May 2010, p. S-846, vol. 138, No. 5, Supplement 1, Abstract No. T2000.

Ducés, A. et al. "Liver Gene Expression Signature to Predict Response to Pegylated Interferon Plus Ribavirin in Chronic Hepatitis C" *Journal of Hepatology*, Apr. 2010, pp. S266-S267, vol. 52, Supplement 1, Abstract No. 684.

Poster shown at the Meeting of the American of the American Association of the Study of Liver Diseases (AASLD) on Sep. 2, 2010.

French Search Report dated Jan. 31, 2012, issued in connection with FR 1151022.

Barsic, N. et al. "Overview and developments in noninvasive diagnosis of nonalcoholic fatty liver disease" *World Journal of Gastroenterology*, Aug. 14, 2012, pp. 3945-3954, vol. 18, No. 30.

Virakul, S. et al. "Histamine induces NF-[kappa]B controlled cytokine secretion by orbital fibroblasts via histamine receptor type-1" *Experimental Eye Research*, May 8, 2016, pp. 85-93, vol. 147.

Anonymous, "Elevated Inflammatory Biomarkers are Associated with Progression to AIDS and Death despite Viral Suppression" Jan. 1, 2010, XP055424021, Retrieved from the Internet: URL:http://www.hivandhepatitis.com/2010_conference/croi/docs/0309_2010_e.html [retrieved on Nov. 13, 2017].

Claims pending in U.S. Appl. No. 16/553,213, filed Nov. 11, 2019, pp. 1-2.

ABD El-Kader, S.M. et al. "Non-alcoholic fatty liver disease: The diagnosis and management" *World J Hepatol.*, Apr. 28, 2015, pp. 846-858, vol. 7, No. 6.

Vernon, G. et al. "Systematic review: the epidemiology and natural history of non-alcoholic fatty liver disease and non-alcoholic steatohepatitis in adults" *Aliment Pharmacol Ther*, 2011, pp. 274-285, vol. 34.

Hashimoto, E. et al. "Characteristics and diagnosis of NAFLD/NASH" *J Gastroenterol Hepatol*, 2013, pp. 64-70, vol. 28, Suppl 4.

Angulo, P. et al. "Non-alcoholic fatty liver disease" *J Gastroenterol Hepatol*, 2002, pp. S186-S190, vol. 17.

Beymer, C. et al. "Prevalence and Predictors of Asymptomatic Liver Disease in Patients Undergoing Gastric Bypass Surgery" *Arch Surg*, Nov. 2003, pp. 1240-1244, vol. 138.

Crespo, J. et al. "Are there Predictive Factors of Severe Liver Fibrosis in Morbidly Obese Patients with Non-alcoholic Steatohepatitis?" *Obesity Surgery*, 2001, pp. 254-257, vol. 11.

Dixon, J.B. et al. "Nonalcoholic Fatty Liver Disease: Predictors of Nonalcoholic Steatohepatitis and Liver Fibrosis in the Severely Obese" *Gastroenterology*, Jul. 2001, pp. 91-100, vol. 121, No. 1.

Gholam, P.M. et al. "Liver Pathology in Morbidly Obese Patients Undergoing Roux-en-Y Gastric Bypass Surgery" *Obesity Surgery*, 2002, pp. 49-51, vol. 12.

Moretto, M. et al. "Hepatic Steatosis In Patients Undergoing Bariatric Surgery and its Relationship to Body Mass Index and Co-Morbidities" *Obesity Surgery*, 2003, pp. 622-624, vol. 13.

Hsiao P.-J. et al. "Significant correlations between severe fatty liver and risk factors for metabolic syndrome" *J Gastroenterol Hepatol*, 2007, pp. 2118-2123, vol. 22.

Fracanzani, A.L. et al. "Risk of Severe Liver Disease in Nonalcoholic Fatty Liver Disease with Normal Aminotransferase Levels: A Role for Insulin Resistance and Diabetes" *Hepatology*, Sep. 2008, pp. 792-798, vol. 48, No. 3.

Angulo, P. et al., "Independent Predictors of Liver Fibrosis in Patients With Nonalcoholic Steatohepatitis" *Hepatology*, Dec. 1999, pp. 1356-1362, vol. 30, No. 6.

Chalasani, N. et al. "The Diagnosis and Management of Non-alcoholic Fatty Liver Disease: Practice Guideline by the American Gastroenterological Association, American Association for the Study of Liver Diseases, and American College of Gastroenterology" *Gastroenterology*, Jun. 2012, pp. 1592-1609, vol. 142, No. 7.

European Association for the Study of the Liver, et al. "EASL-EASD-EASCO Clinical Practice Guidelines for the Management of Non-Alcoholic Fatty Liver Disease" *Obes Facts*, 2016, pp. 65-90, vol. 9, No. 2.

Chalasani, N. et al. "The Diagnosis and Management of Non-alcoholic Fatty Liver Disease: Practice Guideline by the American Association for the Study of Liver Diseases, American College of Gastroenterology, and the American Gastroenterological Association" *Am J Gastroenterol*, Jun. 2012, pp. 811-826, vol. 107.

Farrell, G.C., et al. "Guidelines for the assessment and management of non-alcoholic fatty liver disease in the Asia-Pacific region: Executive summary" *J Gastroenterol Hepatol*, 2007, pp. 775-777, vol. 22.

(56) References Cited

OTHER PUBLICATIONS

Ratziu, V. et al. "A position statement on NAFLD/NASH based on the EASL 2009 special conference" *J Hepatol*, 2010, pp. 372-384, vol. 53.
Sanyal, A.J. et al. "AGA Technical Review on Nonalcoholic Fatty Liver Disease" *Gastroenterology*, Nov. 2002, pp. 1705-1725, vol. 123, No. 5.
Bedossa, P. et al. "Utility and Appropriateness of the Fatty Liver Inhibition of Progression (FLIP) Algorithm and Steatosis, Activity, and Fibrosis (SAF) Score in the Evaluation of Biopsies of Nonalcoholic Fatty Liver Disease" *Hepatology*, Aug. 2014, pp. 565-575, vol. 60, No. 2.
Kleiner, D.E. et al. "Nonalcoholic Fatty Liver Disease: Pathologic Patterns and Biopsy Evaluation in Clinical Research" *Semin Liver Dis*, 2012, pp. 3-13, vol. 32, No. 1.
Kleiner, D.E. et al. "Design and Validation of a Histological Scoring System for Nonalcoholic Fatty Liver Disease" *Hepatology*, Jun. 2005, pp. 1313-1321, vol. 41, No. 6.
Ratziu, V. et al. "Sampling Variability of Liver Biopsy in Nonalcoholic Fatty Liver Disease" *Gastroenterology*, Jun. 2005, pp. 1898-1906, vol. 128, No. 7.
Vuppalanchi, R. et al. "Nonalcoholic Fatty Liver Disease and Nonalcoholic Steatohepatitis: Selected Practical Issues in Their Evaluation and Management" *Hepatology*, Jan. 2009, pp. 306-317, vol. 49, No. 1.
Vuppalanchi, R. et al. "Non-alcoholic fatty liver disease and non-alcoholic steatohepatitis: Selected practical issues in their evaluation and management" *Hepatology*, Jan. 2009, pp. 1-23, author manuscript.
Musso, G. et al. "Meta-analysis: Natural history of non-alcoholic fatty liver disease (NAFLD) and diagnostic accuracy of non-invasive tests for liver disease severity" *Ann Med*, 2011, pp. 617-649, vol. 43, No. 8.
Ryan, M.C. et al. "Associations Between Liver Histology and Severity of the Metabolic Syndrome in Subjects With Nonalcoholic Fatty Liver Disease" *Diabetes Care*, May 2005, pp. 1222-1224, vol. 28, No. 5.
Marchesini, G. et al. "Nonalcoholic Fatty Liver, Steatohepatitis, and the Metabolic Syndrome" *Hepatology*, Apr. 2003, pp. 917-923, vol. 37, No. 4.
Bedogni, G. et al. "The Fatty Liver Index: a simple and accurate predictor of hepatic steatosis in the general population" *BMC Gastroenterol*, Nov. 2006, pp. 1-7, vol. 6, No. 33.
Lee, J.-H. et al. "Hepatic steatosis index: a simple screening tool reflecting nonalcoholic fatty liver disease" *Dig Liver Dis*, 2010, pp. 503-508, vol. 42.
Poynard, T. et al., "The diagnostic value of biomarkers (SteatoTest) for the prediction of liver steatosis" *Comp Hepatol*, 2005, pp. 1-14, vol. 4, No. 10.
Fedchuk, L. et al. "Performance and limitations of steatosis biomarkers in patients with nonalcoholic fatty liver disease" *Aliment Pharmacol Ther*, 2014, pp. 1209-1222, vol. 40.
Fishbein, M. et al. "Hepatic MRI for Fat Quantitation: Its Relationship to Fat Morphology, Diagnosis, and Ultrasound" *J Clin Gastroenterol*, Aug. 2005, pp. 619-625, vol. 39, No. 7.
Saadeh, S. et al. "The Utility of Radiological Imaging in Nonalcoholic Fatty Liver Disease" *Gastroenterology*, Sep. 2002, pp. 745-750, vol. 123, No. 3.
Angulo, P. et al. "The Nafld Fibrosis Score: a Noninvasive System That Identifies Liver Fibrosis in Patients with NAFLD" *Hepatology*, Apr. 2007, pp. 846-854, vol. 45, No. 4.
Boursier, J. et al. "Diagnostic accuracy and prognostic significance of blood fibrosis tests and liver stiffness measurement by FibroScan in non-alcoholic fatty liver disease" *J Hepatol*, 2016, pp. 570-578, vol. 65.
Koplay, M. et al. "Importance of imaging and recent developments in diagnosis of nonalcoholic fatty liver disease" *World J Hepatol*, Apr. 18, 2015, pp. 769-776, vol. 7, No. 5.
Castera, L. et al. "Pitfalls of Liver Stiffness Measurement: a 5-Year Prospective Study of 13,369 Examinations" *Hepatology*, Mar. 2010, pp. 828-835, vol. 51, No, 3.
Wong, V. W-S. et al. "Diagnosis of Fibrosis and Cirrhosis Using Liver Stiffness Measurement in Nonalcoholic Fatty Liver Disease" *Hepatology*, Feb. 2010, pp. 454-462, vol. 51, No. 2.
Wong, V. W-S. et al. "Liver Stiffness Measurement Using XL Probe in Patients With Nonalcoholic Fatty Liver Disease" *Am J Gastroenterol*, Dec. 2012, pp. 1862-1871, vol. 107.
Tilg, H. "Adipocytokines in Nonalcoholic Fatty Liver Disease: Key Players Regulating Steatosis, Inflammation and Fibrosis" *Cuff Pharm Des*, 2010, pp. 1893-1895, vol. 16, No. 17.
Jamali, R. et al. "Serum adipokines might predict liver histology findings in non-alcoholic fatty liver disease" *World J Gastroenterol*, Jun. 7, 2016, pp. 5096-5103, vol. 22, No. 21.
Cusi, K. et al. "Limited value of plasma cytokeratin-18 as a biomarker for NASH and fibrosis in patients with non-alcoholic fatty liver disease" *J Hepatol*, 2014, pp. 167-174, vol. 60.
Grigorescu, M. et al. "A novel pathophysiological-based panel of biomarkers for the diagnosis of nonalcoholic steatohepatitis" *J Physiol Pharmacol*, 2012, pp. 347-353, vol. 63, No. 4.
Pirvulescu, I. et al. "Noninvasive Clinical Model for the Diagnosis of Nonalcoholic Steatohepatitis in Overweight and Morbidly Obese Patients undergoing Bariatric Surgery" *Chirurgia*, 2012, pp. 772-779, vol. 107, No. 6.
Polyzos, S.A. et al. "Adipokines in nonalcoholic fatty liver disease" *Metabolism*, 2016, pp. 1062-1079, vol. 65.
Larter, C.Z. et al. "A fresh look at Nash pathogenesis. Part 1: the metabolic movers" *J Gastroenterol Hepatol*, 2010, pp. 672-690, vol. 25.
Park, S.H. et al. "Body Fat Distribution and Insulin Resistance: Beyond Obesity in Nonalcoholic Fatty Liver Disease among Overweight Men" *J Am Coll Nutr*, 2007, pp. 321-326, vol. 26, No. 4.
Park, B.J. et al. "Visceral adipose tissue area is an independent risk factor for hepatic steatosis" *J Gastroenterol Hepatol*, 2008, pp. 900-907, vol. 23.
Harris, R.B.S. et al., "Location, Location, Location . . ." *Cell Metab*, May 2008, pp. 359-361, vol. 7.
Zhang, X. et al., "CXCL10 plays a key role as an inflammatory mediator and a non-invasive biomarker of non-alcoholic steatohepatitis" *J Hepatol*, 2014, pp. 1365-1375, vol. 61.
Du Plessis, J. et al. "Association of Adipose Tissue Inflammation With Histologic Severity of Nonalcoholic Fatty Liver Disease" *Gastroenterology*, 2015, pp. 635-648, vol. 149, No. 3, Supplemental Materials pp. e1-e14.
Shah, A.G. et al. "Comparison of Noninvasive Markers of Fibrosis in Patients With Nonalcoholic Fatty Liver Disease" *Clin Gastroenterol Hepatol*, Oct. 2009, pp. 1104-1112, vol. 7, No. 10.
Angulo, P. et al. "Simple Noninvasive Systems Predict Long-term Outcomes of Patients With Nonalcoholic Fatty Liver Disease" *Gastroenterology*, Oct. 2013, pp. 1-17, vol. 145, No. 4.
Yoneda, M. et al. "Noninvasive scoring systems in patients with nonalcoholic fatty liver disease with normal alanine aminotransferase levels" *J Gastroenterol*, 2013, pp. 1051-1060, vol. 48.
Brunt, E.M. et al. "Nonalcoholic Steatohepatitis: A Proposal for Grading and Staging the Histological Lesions" *Am J Gastroenterol*, 1999, pp. 2467-2474, vol. 94, No. 9.
Castera, L. et al. "Non-invasive evaluation of liver fibrosis using transient elastography" *J Hepatol*, 2008, pp. 835-847, vol. 48.
Imbert-Bismut, F. et al. "Biochemical markers of liver fibrosis in patients with hepatitis C virus infection: a prospective study" *Lancet*, Apr. 7, 2001, pp. 1069-1075, vol. 357, No. 9262.
Adams, L.A. et al. "Hepascore: An Accurate Validated Predictor of Liver Fibrosis in Chronic Hepatitis C Infection" *Clin Chem*, 2005, pp. 1867-1873, vol. 51, No. 10.
Forns, X. et al. "Identification of Chronic Hepatitis C Patients Without Hepatic Fibrosis by a Simple Predictive Model" *Hepatology*, Oct. 2002, pp. 986-992, vol. 36, No. 4.
Wai, C-T. et al. "A Simple Noninvasive Index Can Predict Both Significant Fibrosis and Cirrhosis in Patients With Chronic Hepatitis C" *Hepatology*, Aug. 2003, pp. 518-526, vol. 38, No. 2.

(56) References Cited

OTHER PUBLICATIONS

Sterling, R.K. et al. "Development of a Simple Noninvasive Index to Predict Significant Fibrosis in Patients With HIV/HCV Coinfection" *Hepatology*, Jun. 2006, pp. 1317-1325, vol. 43, No. 6.

Flanagan, J.J. et al. "Development of monoclonal antibodies to pre-haptoglobin 2 and their use in an enzyme-linked immunosorbent assay (ElISA)" *J Immunol Methods*, 2014, pp. 34-42, vol. 406.

Team, R.C., R: A language and environment for statistical computing. R Foundation for Statistical Computing, Vienna, Austria, http://www.R-project.org/, 2015, pp. 1-16.

Benjamini, Y. et al. "Controlling the False Discovery Rate: a Practical and Powerful Approach to Multiple Testing" *J Roy Statist Soc Ser B*, 1995, pp. 289-300, vol. 57, No. 1.

Youden, W.J. "Index for Rating Diagnostic Tests" Cancer, Jan. 1950, pp. 32-35.

* cited by examiner

SYNERGISTIC COMBINATION OF BIOMARKERS FOR DETECTING AND ASSESSING HEPATIC FIBROSIS

CROSS-REFERENCE TO RELATED APPLICATION

This application is the U.S. national stage application of International Patent Application No. PCT/FR2015/051518, filed Jun. 9, 2015.

The Sequence Listing for this application is labeled "Seq-List.txt" which was created on Dec. 16, 2016 and is 7 KB. The entire content of the sequence listing is incorporated herein by reference in its entirety.

FIELD OF THE INVENTION

The application relates to hepatic fibroses, especially to hepatic fibroses that may appear in a patient infected with one or more hepatitis viruses and/or who is suffering from hepatitis, specifically chronic hepatitis.

The application provides methods and means for determining the stage (or degree) of the hepatic fibrosis of such a patient. More particularly, the methods and means of the application allow to determine, whether or not the stage (or degree) of the hepatic fibrosis of this patient has passed beyond the stage of mild fibrosis.

The methods and means of the invention employ a combination of biomarkers, such as, in particular, the protein CXCL10 and hyaluronic acid (HA).

BACKGROUND OF THE INVENTION

Various diseases cause or lead to tissue lesions of the liver known as hepatic fibrosis. A hepatic fibrosis results, in particular, from excessive accumulation of molecular compounds of the altered extracellular matrix in the hepatic parenchy-ma.

The stage of damage of the liver tissue, especially the nature and extent of hepatic tissue lesions, is evaluated by a score of hepatic fibrosis, especially by the F Metavir score system, which comprises 5 stages from F0 to F4 (cf. Table 25 below). The determination of the score of hepatic fibrosis is essential to the physician since it is a prognostic score.

In fact, this determination is the basis that allows the physician to make a decision of administrating or not administrating a treatment in view of treating these lesions, or at least in view of alleviating their effects. It is also on this basis that the physician decides to initiate a treatment. In particular, if the Metavir fibrosis score is at most F1 (mild fibrosis), the physician generally decides that no treatment should be administered, whereas, if the Metavir fibrosis score is at least F2, it is recommendable to administer a treatment, regardless of the necroinflammatory activity. However, possible treatments bring about major side effects for the patient (treatments including interferon), or their cost is very high (novel antiviral agents).

In this context, it is of crucial importance to the patient to be able to determine reliably whether or not a patient has passed beyond the stage of mild fibrosis.

Now, even though it is relatively easy to identify the stage of cirrhosis (Metavir fibrosis score F4), for example, by transient elastography (FIBROSCAN™), it is nevertheless much more complicated to distinguish in a non-invasive, but still clinically reliable way:

the stages for which the fibrosis is mild at most (Metavir fibrosis score F0 or F1);

advanced fibrosis stages (Metavir fibrosis score F2 or F3).

There are different non-invasive tests that can be applied in the clinic to a patient to attempt to determine the stage of hepatic fibrosis. They employ different biomarkers.

For example, the biomarker HA is employed in the clinical tests ELF™ (U.S. Pat. No. 7,141,380 B2), HEPASCORE™ (Adams et al. 2005; US 2007/0225919 Å1), FIBROSPECT™ (U.S. Pat. No. 6,986,995 B2), FIBROMETER™ (U.S. Pat. No. 8,489,335 B2), and SHASTA™ (Kelleher et al. 2005).

These tests do not employ the protein CXCL10, however.

In fact, the protein CXCL10 is essentially known as a biomarker of the response to anti-HCV therapy using interferon, and has scarcely been described in the context of hepatic fibrosis.

HA has the capacity of inducing the expression of the protein CXCL10. Thus, an increase in HA induces an increase of CXCL10. The concentrations of the two molecules develop into the same direction (an increase of the concentration of HA results in an increase of the concentration of CXCL10). Thus, it was not expected from the beginning that a combination of these two molecules as biomarkers would lead to an extra result in addition to that obtained with only one of the two molecules. However, the present application describes that a synergistic effect is obtained that goes beyond that of a simple juxtaposition of the two molecules as biomarkers.

In addition, the prior art describes experiments trying to associate the protein CXCL10 with other biomarkers to attempt to reliably discriminate the Metavir fibrosis scores F0-F1 from the Metavir fibrosis scores F2-F4, and reports that such experiments are fruitless (Zeremski et al. 2009, page 179, left column, first sentence: "The combination of multiple parameters did not improve the ability to identify patients with minimal fibrosis"). Thus, the subject matter of the present application has overcome a technical prejudice.

SUMMARY OF THE INVENTION

The application relates to methods and means allowing to determine the stage (or degree) of hepatic fibrosis of a patient, especially to determine whether or not the stage (or degree) of hepatic fibrosis of said patient has passed beyond the stage of mild fibrosis.

The inventors have identified particular biomarkers for this purpose, such as CXCL10 (ligand 10 of chemokine (motif CXC)) and HA (hyaluronic acid or hyaluronan). In particular, the inventors have identified particular combinations of biomarkers that, like the combination of CXCL10 with HA, lead to a synergistic effect.

In fact, the inventors demonstrate, in particular, that the combination of marker CXCL10 with marker HA leads to performances that go beyond a simple juxtaposition of their respective individual performances (AUC performances and/or correct classification rate and/or sensitivity and/or NPV and/or specificity and/or PPV). Experimental demonstrations are presented in the Examples below, in particular:

in Example 1 (cf. Table 3),
in Example 3 (cf. Tables 8 and 10), and
in Example 7 (cf. Tables 20 and 21).

The inventors demonstrate that the synergistic effect observed with the combination of CXCL10 and HA is independent of the application of an mROC function for the classification of the patient; cf. the Examples below, in particular:

Example 7, especially Tables 20, 21 and 23,
Example 8, especially Table 24.

The inventors demonstrate that the performances of the combination of CXCL10 with HA are particularly robust (AUC performances and/or correct classification rate and/or sensitivity and/or NPV and/or specificity and/or PPV): cf. Example 9 below.

Comparisons with non-invasive tests of the prior art are furthermore presented in Examples 2 and 4 below.

According to an advantageous embodiment, the detection of HA and CXCL10 is effected as a multiplex detection: cf. Example 10 below. Certain markers of the prior art, such as A2M, have a very high serum concentration and thus cannot be employed in multiplex detection with the markers whose serum concentration is much lower (such as HA and CXCL10).

The means of the invention comprise, in particular:
- methods comprising the quantification of the selected biomarkers (such as CXCL10 and HA, in particular);
- products or reagents specifically suitable for such quantification;
- articles of manufacture, compositions, pharmaceutical compositions, kits, tubes, solid supports comprising such products or reagents, as well as
- computing systems (especially computer program and computing device product), which are especially suitable for the application of the means of the invention.

This model or algorithm can further comprise a preliminary step allowing to classify the patients according to whether their Metavir hepatic fibrosis score is below F4, or equal to F4, for example, by measuring the stiffness of the liver, for example, by FIBROSCAN™.

Figure 9:
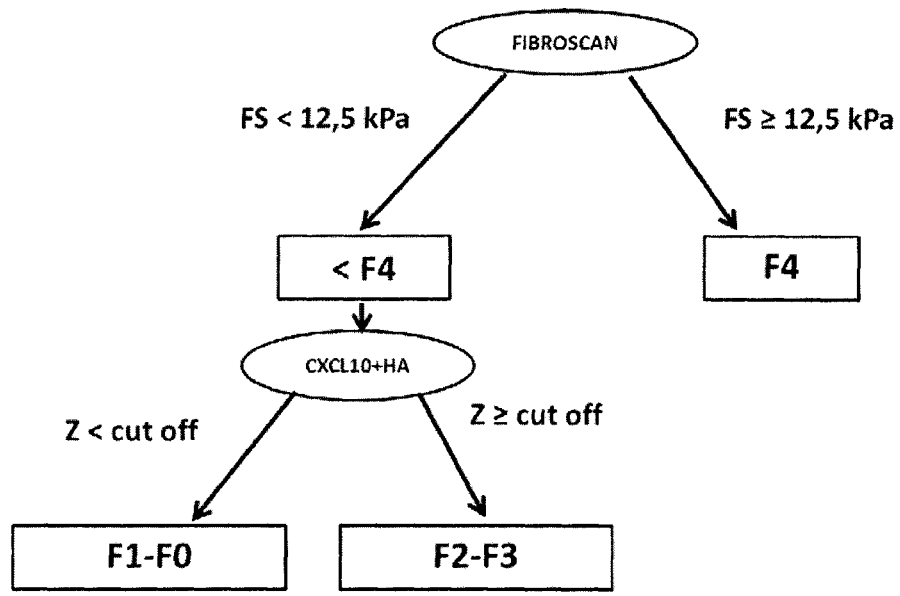
FIGS. 9, 10 and 11 each present a classification model or algorithm comprising the combination of marker HA and marker CXCL10 for the classification of patients as a function of their stage of hepatic fibrosis (Metavir hepatic fibrosis score F0-F1 or F2-F3).

FIG. 9: combination of HA and CXCL10.

Figure 10:
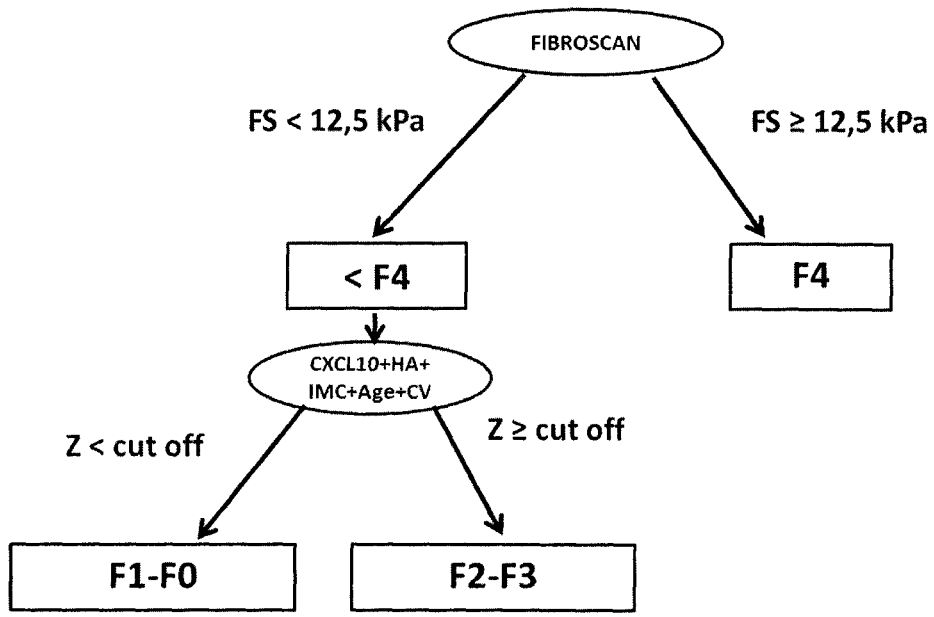
Figure 11:
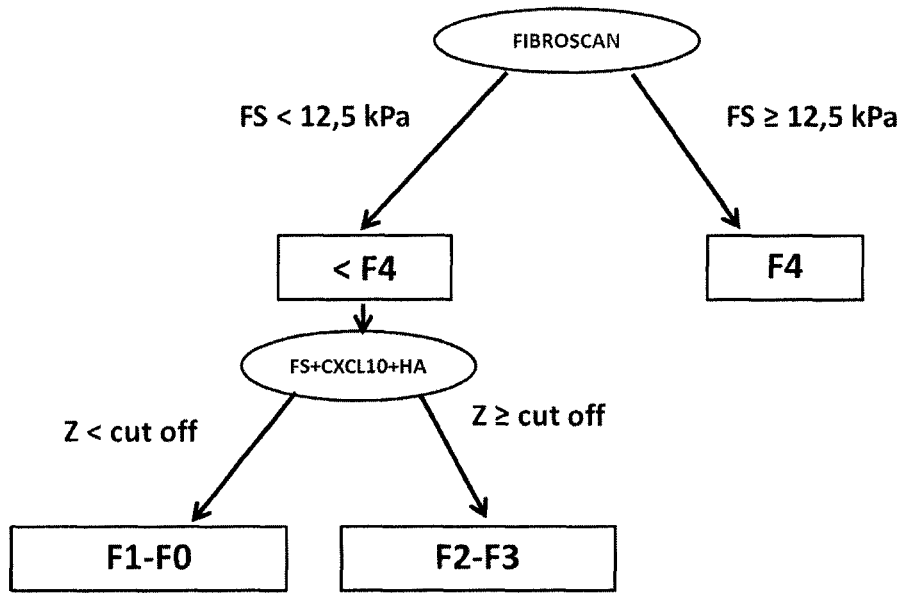

FIGS. 10 and 11: combination of HA, CXCL10 and one or more other additional markers.

FIG. 10: combination of HA, CXCL10 and one or more other additional markers [clinical or anatomical marker(s) and/or virological marker(s)], in this case: body mass index (BMI), age at the sampling date (Age), viral load at the sampling date (VL).

FIG. 11: combination of HA, CXCL10 and the measurement of liver stiffness, measured, for example, by FIBROSCAN™ (FS).

Figure 12:
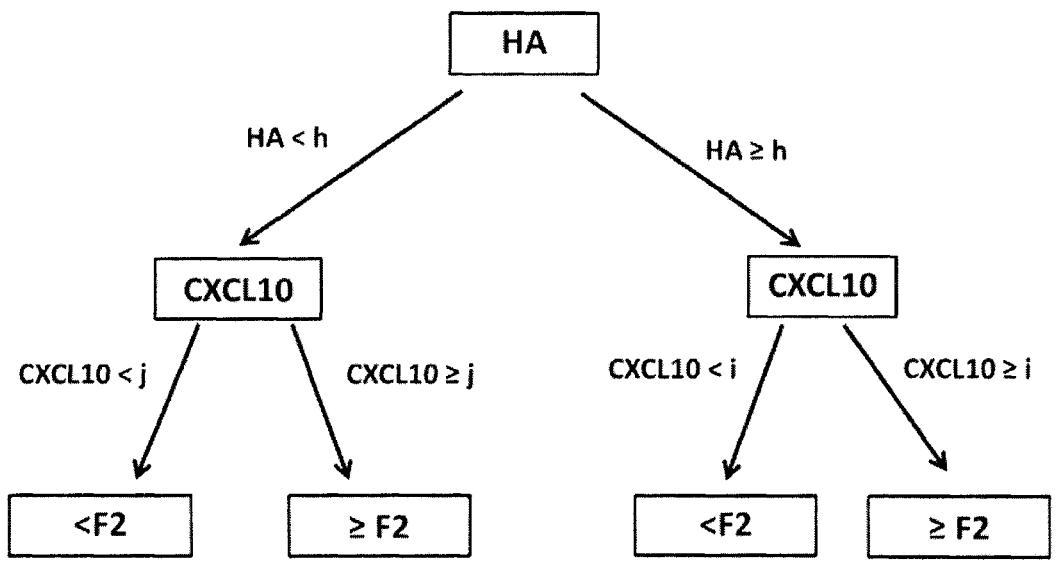

FIG. 12 presents a classification model or algorithm that is not based on a linear function: this model or algorithm is based on a CART (Classification And Regression Tree) classification model and comprises the combination of marker HA and marker CXCL10 (cf. Example 7 below).

FIGS. 13A to 16B illustrate the performances of the combination HA+CXCL10 by means of the method known under the name of Bootstrap (cf. Example 3 below; 1000 subpopulations of the same size randomly chosen from a population of 310 patients; draws with replacement).

The values of AUC and correct classification rate were measured:
- on the one hand, when the applied mROC discriminating rule has those coefficients initially determined on the population of 310 patients ("fix coefficients" or "coef fix"); and
- on the other hand, when the applied mROC discriminating rule has those coefficients determined for each of the 1000 subpopulations ("optimized coefficients" or "coef optim").

AUC=area under the ROC curve
correct classification rate=percentage of correctly classified patients.

Figure 13A:
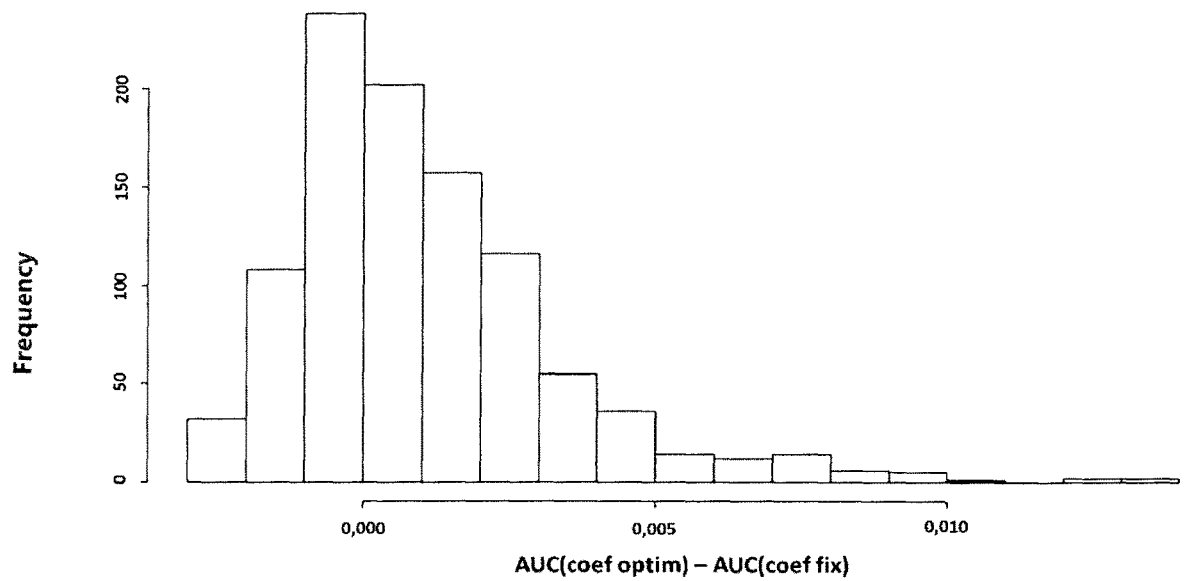
Figure 13B:
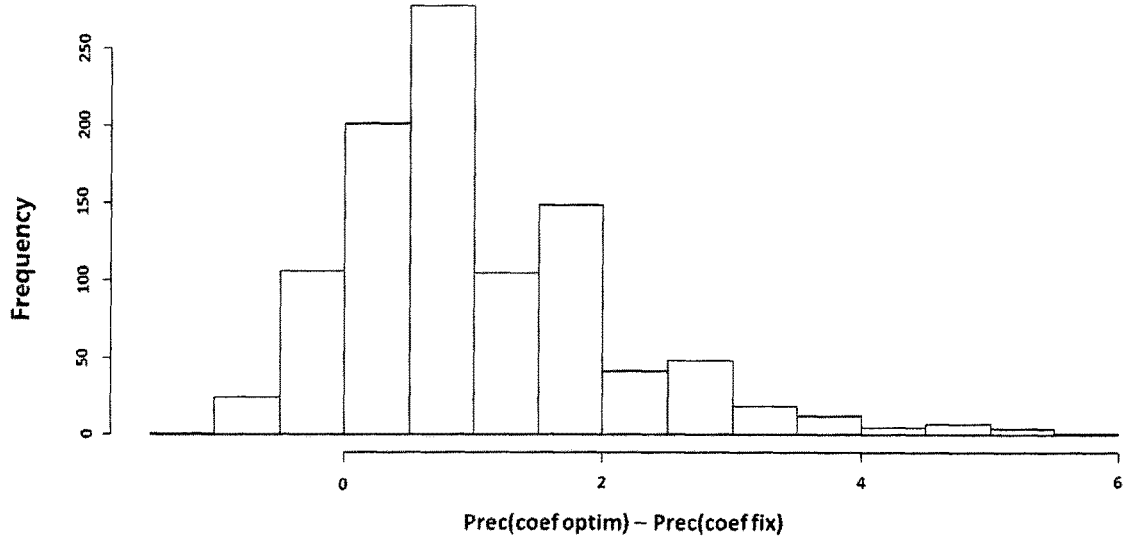

FIGS. 13A and 13B present the values of the differences of AUC and precision that have been measured between, on the one hand, the mROC discriminating rule with "fix coefficients" (or "coef fix") and, on the other hand, the mROC discriminating rule with "optimized coefficients" (or "coef optim") in the form of histograms.

In FIGS. 13A and 13B, the mROC discriminating rule employed the combination of HA+CXCL10.

FIG. 13A presents the histogram of the AUC differences with the fix or optimized coefficients for the combination of HA+CXCL10 in Bootstrap (B=1000) [abscissa: 0.000; 0.005; 0.010].

FIG. 13B presents the histogram of the differences of correct classification rate (percentage of correctly classified patients) with the fix or optimized coefficients for the combination of HA+CXCL10 in Bootstrap (B=1000).

FIGS. 13A and 13B present the values of the differences of AUC and precision that have been measured for the mROC discriminating rule with "fix coefficients" ("coef fix") between, on the one hand, the combination of HA+CXCL10 and, on the other hand, the HA marker alone in the form of histograms.

Figure 14A:
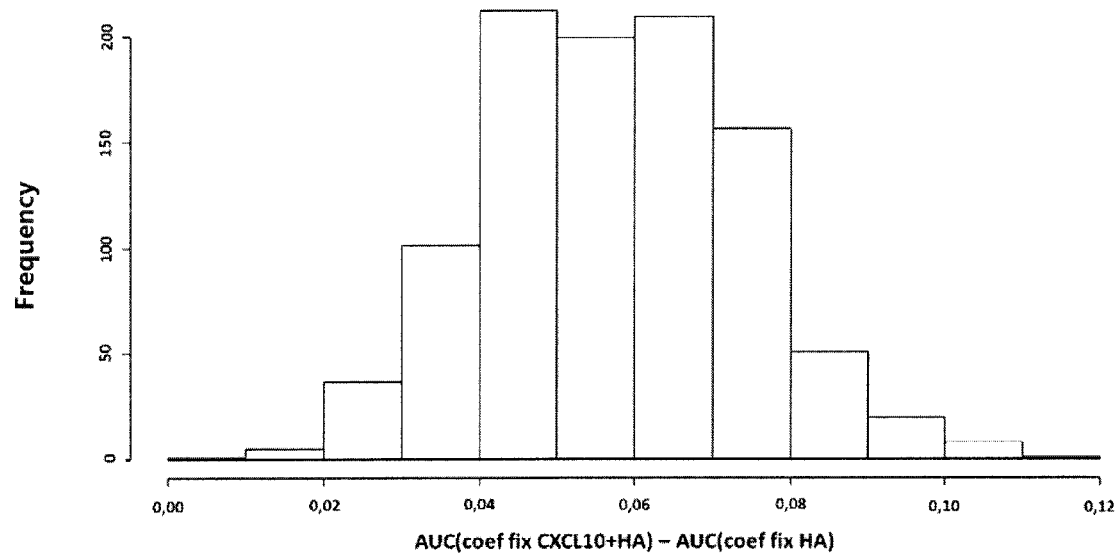

FIG. 14A presents the histogram of the AUC differences between, on the one hand, the combination of HA+CXCL10 and, on the other hand, the HA marker alone in Bootstrap (B=1000) with fix coefficients ("coef fix") [abscissa: 0.02; 0.04; 0.06; 0.08; 0.10; 0.12].

Figure 14B:
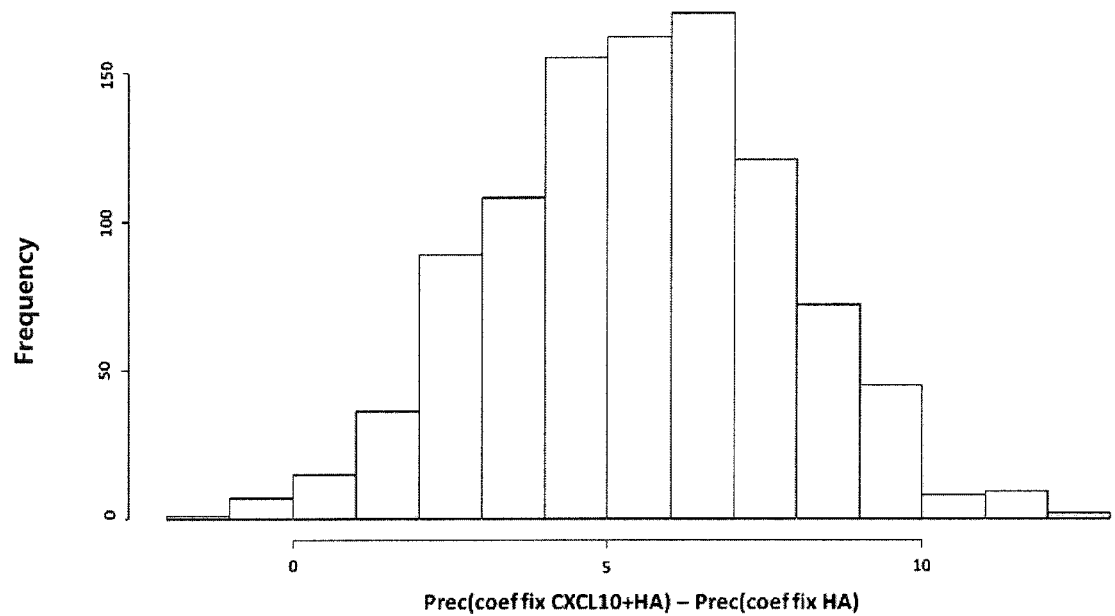

FIG. 14B presents the histogram of the differences of correct classification rate between, on the one hand, the combination of HA+CXCL10 and, on the other hand, the HA marker alone in Bootstrap (B=1000) with fix coefficients ("coef fix").

Figure 15:
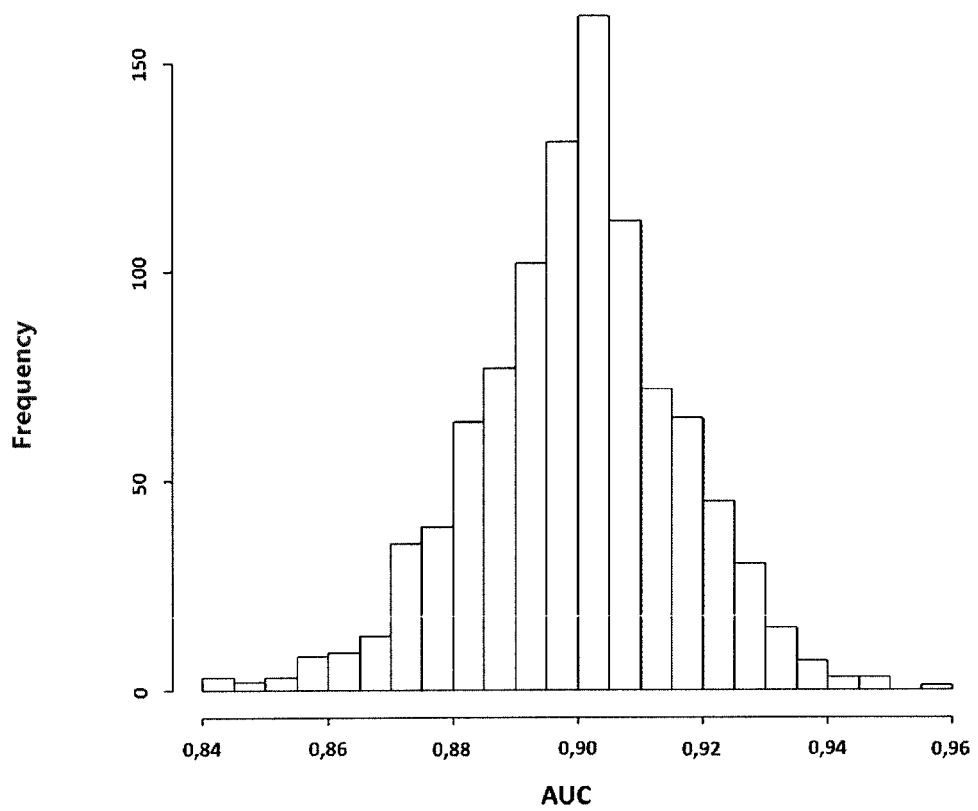

FIG. 15 presents the histogram of AUC for the combination of HA+CXCL10 in Bootstrap (B=1000) with fix coefficients ("coef fix") [abscissa: 0.84; 0.86; 0.88; 0.90; 0.92; 0.94; 0.96]; cf. Example 9 below.

Figure 16A:
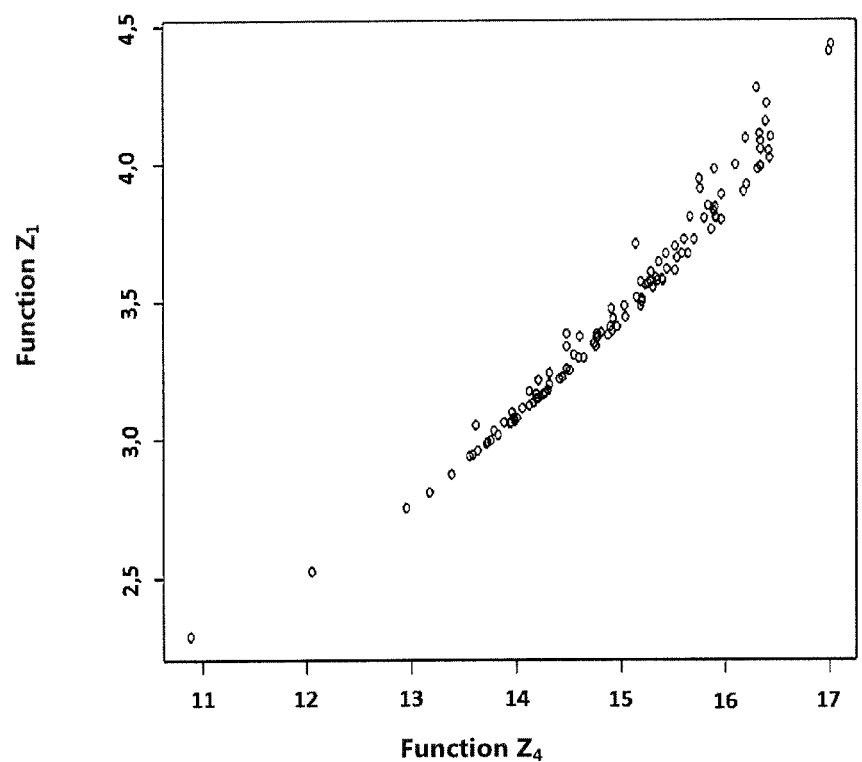
Figure 16B:
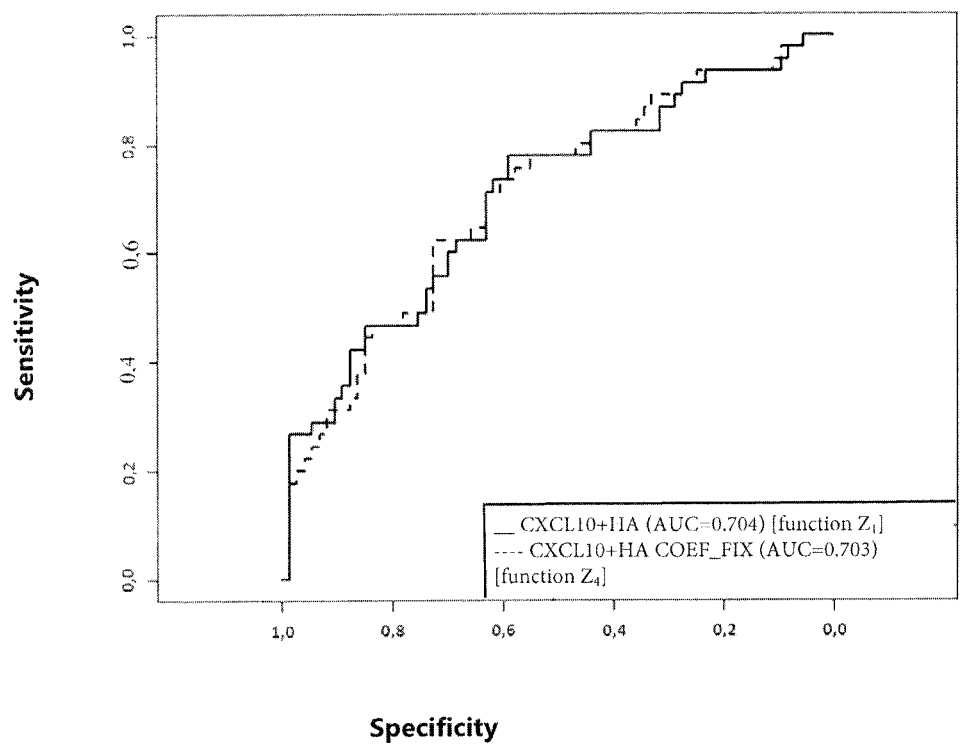

FIGS. 16A and 16B compare the performances of the mROC function obtained on the population of 118 patients of Example 1 (markers HA+CXCL10; function Z1; cf. Table 2 below) with those of the function mROC obtained on the population of 310 patients of Example 3 (markers HA+CXCL10; function Z4; cf. Table 7 below), when both are applied to the population of 118 patients; cf. Example 9 below.

FIG. 16A: ordinate, function Z1 of Example 1 [Z=(0.3686)×CXCL10$^r$+(0.3064)×HA$^r$, with λCXCL10=−0.013 and λHA=0.099]; abscissa, function Z4 of Example 3 [Z=(1.999)×CXCL10$^r$+(2.852)×HA$^r$, with λCXCL10=−0.116 and λHA=−0.288].

FIG. 16B. ordinate, sensitivity; abscissa, specificity; curves of Z1 and Z4 (the two curves merge).

DETAILED DESCRIPTION OF THE INVENTION

The application relates to the subject matter as defined in the claims as filed, to the subject matter described above, and to the subject matter illustrated in the "Examples" part.

In the application, unless specified otherwise or dictated otherwise by the context, all terms have their usual meanings in the fields in question.

The application relates to a process for determining, especially for determining with a high probability, the stage (or degree) of hepatic fibrosis in a patient infected with one or more hepatitis viruses and/or who is suffering from hepatitis, specifically chronic hepatitis.

The hepatitis virus of viruses can be, for example, one or more hepatitis C viruses and/or hepatitis B viruses and/or hepatitis D viruses, especially hepatitis C viruses.

Said hepatitis C virus may be of any genotype. For example, the genotype of said hepatitis C virus may be genotype 1, 2, 3, 4, 5, 6 or 7, especially genotype 1 or 4.

Said patient is a mammal, especially a human.

The process of the application employs the quantification of different markers, which can all be measured or determined in an essentially non-invasive way (the degree of invasive intervention with the body of the patient does not go beyond a simple sampling of biological fluid). The process of the application can be performed in vitro.

In particular, the process of the application is a process for determining, especially for determining with a high probability, whether or not the stage (or degree) of hepatic fibrosis of said patient has passed beyond the stage of mild fibrosis.

Said "stage (or degree) of hepatic fibrosis that has not passed beyond the stage of mild fibrosis" means a stage that is equal to or lower than that of mild fibrosis.

Said "stage (or degree) of hepatic fibrosis that has passed beyond the stage of mild fibrosis" means a stage that is higher than that of mild fibrosis.

The different stages of hepatic fibrosis are as follows (in the order from a weak degree to a stronger degree):
absence of fibrosis,
portal fibrosis without septum,
portal fibrosis with septums (i.e., with at least one or more septums),
septal fibrosis without cirrhosis, and
cirrhosis.

Said stage of mild fibrosis is that of a portal fibrosis without septum.

When the stage of hepatic fibrosis of said patient has not passed beyond the stage of mild fibrosis, the liver of this patient is thus either free of fibrosis (absence of fibrosis), or suffering from a portal fibrosis without septum.

When the stage of hepatic fibrosis of said patient has passed beyond the stage of mild fibrosis, the liver of this patient is thus suffering from a portal fibrosis with septums, or from a septal fibrosis without cirrhosis, or from a cirrhosis.

There are various systems of hepatic fibrosis scores. The most common is the Metavir score system.

TABLE 25

Correspondence between the stages of fibrosis and the Metavir fibrosis scores.

| Stage of fibrosis | Metavir fibrosis score |
| --- | --- |
| Absence of fibrosis | F0 |
| Portal fibrosis without septum | F1 |
| Portal fibrosis with septums | F2 |
| Septal fibrosis without cirrhosis | F3 |
| Cirrhosis | F4 |

Said stage of mild fibrosis is thus a degree of hepatic fibrosis that has a score of F1 according to the Metavir scores system.

Thus, a score of hepatic fibrosis indicating that the liver of said patient has not passed beyond the stage of mild fibrosis is a score of at most F1, i.e., a score of F0 or F1, according to the Metavir scores system.

Thus, a score of hepatic fibrosis indicating that the liver of said patient has passed beyond the stage of mild fibrosis is a score of at least F2, i.e., a score of F2, F3 or F4, according to the Metavir scores system.

Another hepatic fibrosis scores system is Ishak's system (Goodman 2007).

TABLE 26

Correspondence between the stages of fibrosis and Ishak's fibrosis scores.

| Stage of fibrosis | Ishak's fibrosis score |
| --- | --- |
| Absence of fibrosis | F0 |
| Portal fibrosis without septum | F1/F2 |
| Portal fibrosis with septums | F3 |
| Septal fibrosis without cirrhosis | F4 |
| Cirrhosis | F5/F6 |

Said stage of mild fibrosis is thus a degree of hepatic fibrosis that has a score of F1/F2 according to Ishak's scores system.

Thus, a score of hepatic fibrosis indicating that the liver of said patient has not passed beyond the stage of mild fibrosis is a score of at most F2, i.e., a score of F0, F1 or F2, according to Ishak's scores system.

Thus, a score of hepatic fibrosis indicating that the liver of said patient has passed beyond the stage of mild fibrosis is a score of at least F3, i.e., a score of F3, F4, F5 or F6, according to Ishak's scores system.

Determining whether or not the stage (or degree) of the hepatic fibrosis of a patient infected with one or more hepatitis viruses and/or who is suffering from hepatitis, specifically chronic hepatitis, has passed beyond the stage of mild fibrosis is particularly essential to the physician.

In fact, most of the treatments (whether they be an antihepatitis, anti-HCV or anti-hepatic fibrosis treatment), and more particularly those comprising the administration of interferon, show extremely severe side effects. These treatments are thus generally administered only when the liver of said patient has passed beyond the stage of mild fibrosis (Metavir score of at least F2).

Thus, the process of the application can be used not only in the diagnostic of hepatic fibrosis or of the stage of hepatic fibrosis, but also in the treatment of a liver disease, especially to determine the moment when a treatment must be administered to the patient. The process of the invention can thus be a process for the therapy of a patient, comprising administering an antihepatitis and/or anti-HCV and/or anti-hepatic fibrosis treatment only when it has been determined, using the means of the application, that the patient has passed beyond the stage of mild fibrosis, or else a process for the therapy of a patient, comprising adjusting an antihepatitis and/or anti-HCV and/or anti-hepatic fibrosis treatment as a function of the response of the hepatic tissue of the patient, as determined using the means of the application. In particular, said treatment can be a treatment aiming at blocking or slowing down the progression of hepatic fibrosis by eliminating the virus (especially in the case of hepatitis C) and/or by blocking the replication of the virus (especially in the case of hepatitis B).

Advantageously, the process of the application is applicable to whatever stage of hepatic fibrosis of the patient: this stage can be one from an absence of hepatic fibrosis to one of cirrhosis.

Thus, the hepatic fibrosis score of said patient can be F0, F1, F2, F3 or F4, especially F0, F1, F2 or F3, especially F0, F1 or F2, especially F1, F2 or F3, especially F1 or F2, according to the Metavir fibrosis scores system.

Said patient can be a patient in which the stiffness of the liver has been measured beforehand, especially by a non-invasive method, such as transient elastography (for example, by FIBROSCAN™).

The process of the application employs the quantification, especially the detection and quantification, of biological markers (or variables).

The biological markers (or biomarkers) selected for performing the process include several different circulating molecules. They may further include zero, one or more additional markers that are not circulating molecules.

Circulating Molecules

The term "circulating molecules" is understood to have its usual meaning in the field. Generally, the circulating molecules are molecules that are present in the blood of a mammal, especially of a human, in acellular form: they are contained neither in a circulating cell nor in a tissue cell. Generally, the molecules circulating in the blood are also circulating in the plasma. Generally, the molecules circulating in the blood are also circulating in the serum. The circulating molecules can be, for example, proteins, glycoproteins, enzymes, polysaccharides, lipids, glycerides, hormones. The circulating molecules can be, for example, molecules or metabolites produced by the cells of the organism of said patient. In particular, the circulating molecules can be, for example, molecules (or metabolites) produced by the cells of the organism of said patient, but not produced by a virus, especially a hepatitis virus. The formed elements of the blood, such as the platelets, as well as the viruses, such as the hepatitis virus, are circulating, but are not molecules. Thus, they are not part of the circulating molecules within the meaning of the invention. When said patient is a human, these circulating molecules are human circulating molecules. Examples of circulating molecules include, in particular:

the protein CXCL10 (complete form and cleaved forms),
hyaluronic acid or hyaluronan (HA),
gamma-glutamyl transpeptidase (GGT),
aspartate aminotransferase (AST),
alanine aminotransferase (ALT),
apolipoprotein A1 (ApoA1),
alpha-2-macroglobuline (A2M),
inhibitor 1 of metalloproteinase (TIMP1),
vimentin (VIM),
secreted phosphoprotein-1 (SPP1),
interleukin-6 signal transducer (IL6ST),
cyclin-dependent kinase 2A inhibitor (p14ARF),
matrix metallopeptidase 9 (MMP9),
angiopoietin 2 (ANGPT2),
chemokine ligand 11 motif CXC (CXCL11),
matrix metallopeptidase 2 (MMP2),
matrix metalloproteinase 7 (MMP7),
S100 calcium binding protein A4 (S100A4),
inhibitor 1 of metalloproteinase (TIMP1),
chitinase-3 type protein 1 (CHI3L1),
collagen alpha-1(I) chain (COL1A1),
chemokine 1 of the growth-controlling protein alpha motif CXC (CXCL1),
chemokine ligand 6 motif CXC (CXCL6),
"Indian hedgehog" protein (IHH),
interferon-stimulated transcription factor 3G (IRF9),
matrix metalloproteinase 1 (MMP1).

In order to quantify, especially to detect and quantify, one or more of the circulating molecules, a biological sample, especially a sample of a biological fluid, must be or must have been taken from the patient.

In accordance with the application, the circulating molecules selected for performing the process comprise (or consist of) at least two different circulating molecules.

In particular, the selected circulating molecules comprise (or consist of) at least hyaluronic acid (HA) and the protein CXCL10 (CXCL10).

The inventors demonstrate that the combination of marker CXCL10 with marker HA leads to a synergistic effect, i.e., performances that go beyond a simple juxtaposition of their respective individual performances (AUC performances and/or correct classification rate and/or sensitivity and/or NPV and/or specificity and/or PPV). Experimental demonstrations are presented in the Examples below, in particular:

in Example 1 (cf. Table 3),
in Example 3 (cf. Tables 8 and 10), and
in Example 7 (cf. Tables 20 and 21).

Comparisons with non-invasive tests of the prior art are further presented in Examples 2 and 4 below.

Hyaluronic acid (HA) and the protein CXCL10 (CXCL10) are well known to the skilled person.

HA is one of the principal components of the extracellular matrix. It is a glycosaminoglycane of empirical formula $C_{14}H_{23}NO_{12}$ ($C_{14}H_{21}NO_{11}$)$_n$ (CAS number=9004-61-9). Its molar mass is about 776.647 g/mol. HA is a polymer of hyalobiuronic acid; its structural formula is as follows:

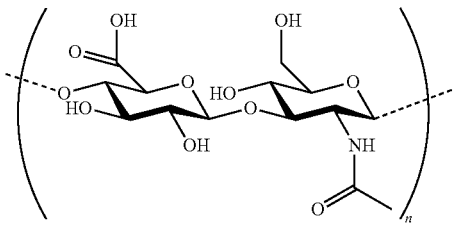

CXCL10 is the ligand 10 to chemokine (motif CXC) [C-X-C motif chemokine 10], also known under the designation of C7; IFI10; INP10; IP-10; SCYB10; crg-2; gIP-10 or mob-1. Its human sequence is described in data bases under the accession number NM_001565.

The precursor form of the protein CXCL10 (human) is a protein constituted of 98 amino acids of the following sequence:

[SEQ ID NO: 1]
MNQTAILICCLIFLTLSGIQGVPLSRTVRCTCISISNQPVNPRSLEKLE
IIPASQFCPRVEIIATMKKKGEKRCLNPESKAIKNLLKAVSKERSKRSP
or

[SEQ ID NO: 2]
MNQTAILICCLIFLTLSGIQGVPLSRTVRCTCISISNQPVNPRSLEKLE
IIPASQFCPRVEIIATMKKKGEKRCLNPESKAIKNLLKAVSKEMSKRSP, wherein these two sequences differ by only one amino acid positioned in the C-terminal portion (ERS in the C-terminal portion of SEQ ID NO: 1 versus EMS in the C-terminal portion of SEQ ID NO: 2).

The signal peptide of the precursor form of CXCL10 is a peptide constituted of 21 amino acids that is identical with fragment 1-21 of the sequence of SEQ ID NO: 1 or 2, namely:

[SEQ ID NO: 3]
MNQTAILICCLIFLTLSGIQG,

There are at least three circulating forms of the protein CXCL10, namely:
- a form called agonist, constituted of 77 amino acids;
- a form called antagonist, constituted of 75 amino acids; and
- a form resulting from cleavage after secretion (proteolytic cleavage by keratinocytes), constituted of 73 amino acids.

The agonist form of CXCL10 is a protein of 77 amino acids of the following sequence:
VPLSRTVRCTCISISNQPVNPRSLEKLEIIPASQFCPRVEIIATMKKKGEKRCLNPES
KAIKNLLKAVSKERSKRSP [SEQ ID NO: 4], or
VPLSRTVRCTCISISNQPVNPRSLEKLEIIPASQFCPRVEIIATMMKGEKRCLNPES
KAIKNLLKAVSKEMSKRSP [SEQ ID NO: 5]. The structure of this protein of 77 amino acids was determined by NMR (PDB identity=1LV9, published on Sep. 18, 2002; cf. Booth et al. 2002), and by X rays (PDB identity at 3 Å=107Y; PDB identity at 2 Å=1080; PDB identity at 1.92 Å=107Z; Swaminathan et al. 2003).

The antagonist form of CXCL10 is a protein of 75 amino acids whose sequence is that of the agonist form truncated by 2 N-terminal amino acids. The antagonist form of CXCL10 has thus the following sequence:

[SEQ ID NO: 6]
LSRTVRCTCISISNQPVNPRSLEKLEIIPASQFCPRVEIIATMKKKGEK
RCLNPESKAIKNLLKAVSKERSKRSP,
or

[SEQ ID NO: 7]
LSRTVRCTCISISNQPVNPRSLEKLEIIPASQFCPRVEIIATMKKKGEK
CLNPESKAIKNLLKAVSKEMSKRSP,

The form CXCL10, which results from cleavage after secretion, is a protein of 73 amino acids, whose sequence is that of the agonist form truncated by 4 C-terminal amino acids. The form CXCL10, which results from cleavage after secretion, has thus the following sequence:

[SEQ ID NO: 8]
VPLSRTVRCTCISISNQPVNPRSLEKLEIIPASQFCPRVEIIATMKKKGE
KRCLNPESKAIKNLLKAVSKERS,
or

[SEQ ID NO: 9]
VPLSRTVRCTCISISNQPVNPRSLEKLEIIPASQFCPRVEIIATMKKKGE
KRCLNPESKAIKNLLKAVSKEMS,

The circulating forms of protein CXCL10 (human) thus comprise the proteins of SEQ ID NO: 4 to NO: 9, especially:
SEQ ID NO: 4 and/or NO: 5,
SEQ ID NO: 6 and/or NO: 7, and
SEQ ID NO: 8 and/or NO: 9.

In accordance with the application, the quantification, especially the detection and quantification, of CXCL10 includes the quantification, or detection and quantification, of at least one, especially more than one, especially all the circulating forms of protein CXCL10.

In accordance with the application, the quantification, especially the detection and quantification, of CXCL10 includes the quantification, or detection and quantification, of at least one, especially more than one, especially all the circulating forms of the proteins of SEQ ID NOS: 4 to 9.

The circulating molecules selected for performing the process can be constituted of protein CXCL10 and HA. In this case, CXCL10 and HA are the only two circulating molecules that are selected or used as biological markers.

Alternatively, one or more other (different) circulating proteins may be selected in addition to HA and CXCL10.

According to an alternative or complementary embodiment, these other selected circulating molecules do not comprise alpha-2 macroglobulin (A2M). In fact, in contrast to HA and to protein CXCL10, the protein A2M is present in high amounts in the blood of human patients. Therefore, it is not possible, or at least very difficult in routine, to measure the concentration of A2M in multiplex detection with those of HA and of protein CXCL10.

According to an alternative or complementary embodiment, these other selected circulating molecules do not comprise "granulocyte-macrophage colony-stimulating factor" (GMCSF).

According to an alternative or complementary embodiment, these other selected circulating molecules do not comprise interleukin 12 (IL 12).

According to an alternative or complementary embodiment, these other selected circulating molecules do not comprise interleukin 2 (IL 2).

According to an alternative or complementary embodiment, these other selected circulating molecules do not comprise matrix metallopeptidase 13 (MMP13).

According to an alternative or complementary embodiment, these other selected circulating molecules do not comprise alanine aminotransferase (ALT).

According to an alternative or complementary embodiment, these other selected circulating molecules do not comprise gamma glutamyl transpeptidase (GGT).

According to an alternative or complementary embodiment, these other selected circulating molecules do not comprise the protein "intercellular adhesion molecule" (ICAM1).

According to an alternative or complementary embodiment, these other selected circulating molecules do not comprise interleukin 4 (IL 4).

According to an alternative or complementary embodiment, these other selected circulating molecules do not comprise ligand 6 to chemokine motif CXC (CXCL9).

According to an alternative or complementary embodiment, these other selected circulating molecules do not comprise the protein "vascular cell adhesion molecule 1" (VCAM1).

According to an alternative or complementary embodiment, these other selected circulating molecules do not comprise "retinol binding protein 4" (RBP4).

According to an alternative or complementary embodiment, these other selected circulating molecules do not comprise inhibitor 1 of metalloproteinase (TIMP1).

According to an alternative or complementary embodiment, these other selected circulating molecules do not comprise vimentin (VIM).

According to an alternative or complementary embodiment, these other selected circulating molecules do not comprise secreted phosphoprotein 1 (SPP1).

According to an alternative or complementary embodiment, these other selected circulating molecules do not comprise aspartate aminotransferase (AST).

According to an alternative or complementary embodiment, these other selected circulating molecules do not comprise apolipoprotein A1 (ApoA1).

According to an alternative or complementary embodiment, these other selected circulating molecules do not comprise interleukin-6 signal transducer (IL6ST).

According to an alternative or complementary embodiment, these other selected circulating molecules do not comprise the inhibitor of cyclin-dependent kinase 2A (p14ARF).

According to an alternative or complementary embodiment, these other selected circulating molecules do not comprise matrix metallopeptidase 9 (MMP9).

According to an alternative or complementary embodiment, these other selected circulating molecules do not comprise angiopoietin 2 (ANGPT2).

According to an alternative or complementary embodiment, these other selected circulating molecules do not comprise ligand 11 to chemokine motif CXC (CXCL11).

According to an alternative or complementary embodiment, these other selected circulating molecules do not comprise matrix metallopeptidase 2 (MMP2).

According to an alternative or complementary embodiment, these other selected circulating molecules do not comprise matrix metallopeptidase 7 (MMP1).

According to an alternative or complementary embodiment, these other selected circulating molecules do not comprise S100 calcium binding protein A4 (S100A4).

According to an alternative or complementary embodiment, these other selected circulating molecules do not comprise inhibitor 1 of metalloproteinase (TIMP1).

According to an alternative or complementary embodiment, these other selected circulating molecules do not comprise protein 1 of the chitinase-3 type (CHI3L1).

According to an alternative or complementary embodiment, these other selected circulating molecules do not comprise the alpha-1(I) chain of collagen (COL1A1).

According to an alternative or complementary embodiment, these other selected circulating molecules do not comprise chemokine 1 of the growth-controlling protein alpha motif CXC (CXCL1).

According to an alternative or complementary embodiment, these other selected circulating molecules do not comprise ligand 6 to chemokine motif CXC (CXCL6).

According to an alternative or complementary embodiment, these other selected circulating molecules do not comprise the protein "Indian hedgehog" (IHH).

According to an alternative or complementary embodiment, these other selected circulating molecules do not comprise the interferon-stimulated transcription factor 3G (IRF9).

According to an alternative or complementary embodiment, these other selected circulating molecules do not comprise matrix metalloproteinase 1 (MMP1).

According to an alternative or complementary embodiment, these other selected circulating molecules do not comprise any of proteins GMCSF, IL-12, IL-2 and MMP13.

According to an alternative or complementary embodiment, these other selected circulating molecules do not comprise any of proteins A2M, GMCSF, IL-12, IL-2 and MMP13.

According to an alternative or complementary embodiment, these other selected circulating molecules do not comprise any of proteins ALT, GGT, ICAMI, IL-4, CXCL9, VCAM1 and RBP4.

According to an alternative or complementary embodiment, these other selected circulating molecules do not comprise any of proteins A2M, ALT, GGT, ICAMI, IL4, CXCL9, VCAM1 and RBP4.

According to an alternative or complementary embodiment, these other selected circulating molecules do not comprise any of proteins A2M, TIMP1, VIM and SPP1.

According to an alternative or complementary embodiment, these other selected circulating molecules do not comprise any of proteins A2M, AST, ApoA1, IL6ST, p14ARF, MMP9, ANGPT2, CXCL11, MMP2, MMP7, S100A4, TIMP1, CHI3L1, COL1A1, CXCL1, CXCL6, IHH, IRF9 and MMP1.

According to an alternative or complementary embodiment, these other selected circulating molecules do not comprise any of proteins A2M, GMCSF, IL-12, IL-2, MMP13, ALT, GGT, ICAMI, IL4, CXCL9, VCAM1, RBP4, TIMP1, VIM, SPP1, AST, ApoA1, IL6ST, p14ARF, MMP9, ANGPT2, CXCL11, MMP2, MMP7, S100A4, TIMP1, CH13L1, COL1A1, CXCL1, CXCL6, IHH, IRF9 and MMP1.

According to an alternative or complementary embodiment, the total number of (different) circulating molecules are selected in numbers of six, five, four, three or two, especially in numbers of five, four, three or two, especially in numbers of four, three or two, especially in numbers of three or two, especially in numbers of two.

Optional Additional Marker(s) [that are not Circulating Molecules]

In addition to the circulating molecules (and especially in addition to HA and CXCL10), the selected biological markers can further comprise zero, one or more additional marker(s) that are not circulating molecules, in particular, that are not human circulating molecules.

The term "additional marker(s)" (or "selected additional marker(s)") herein means those of the selected biological markers that are not one of the circulating molecules, in particular, that are not one of the human circulating molecules.

For example, the selected biological markers can comprise, in addition to said circulating molecules (and especially in addition to HA and CXCL10), one or more additional markers selected from:
the formed elements of the blood (for example, the platelets),
the clinical or anatomical characteristics (or markers) of said patient, and
the virological characteristics (or markers) of said patient.
In particular, the additional markers are selected from:
the clinical or anatomical characteristics (or markers) of said patient, and
the virological characteristics (or markers) of said patient.

The clinical or anatomical characteristics (or markers) are advantageously characteristics the measurement of which does not require detection or quantification in a sample of biological fluid of said patient, and more generally the measurement of which can be performed without taking a biological sample from said patient. For example, the age, body mass index (BMI), sex and liver stiffness are clinical or anatomical characteristics (or markers) that can be quantified by extracorporeal measurement without taking a sample of biological fluid, and more generally without taking a biological sample from said patient (the stiffness of the liver can be measured by transient elastography, especially by FIBROSCAN™, and more generally without any invasive intervention.

Examples of clinical or anatomical characteristics of said patient include, in particular, the age of said patient, the BMI of said patient, the sex of said patient, and the stiffness of the liver of said patient (FS), more particularly the age of said patient, the BMI of said patient, and the stiffness of the liver of said patient (FS).

The marker "age of said patient" includes, in particular:
the age of said patient at the date when the taking of the sample of biological fluid required for the detection or quantification of the circulating molecules was done;
the age of said patient at the date when the diagnostics of an infection by a hepatitis virus was done;
the age of said patient at the date when they received an antihepatitis therapy for the first time;
more particularly the age of said patient at the date when the taking of the sample of biological fluid required for the detection or quantification of the circulating molecules was done.

The marker "BMI of said patient" includes, in particular:
the BMI of said patient at the date when the taking of the sample of biological fluid required for the detection or quantification of the circulating molecules was done;
the BMI of said patient at the date when the diagnostics of an infection by a hepatitis virus was done;
the BMI of said patient at the date when they received an antihepatitis therapy for the first time;
more particularly the BMI of said patient at the date when the taking of the sample of biological fluid required for the detection or quantification of the circulating molecules was done.

Thus, examples of clinical or anatomical characteristics of said patient include, more particularly:
the age of said patient at the date when the taking of the sample of biological fluid required for the detection or quantification of the circulating molecules was done;
the BMI of said patient at the date when the taking of the sample of biological fluid required for the detection or quantification of the circulating molecules was done;
the sex of said patient (male or female), and
the stiffness of the liver of said patient (FS);
more particularly:
the age of said patient at the date when the taking of the sample of biological fluid required for the detection or quantification of the circulating molecules was done;
the BMI of said patient at the date when the taking of the sample of biological fluid required for the detection or quantification of the circulating molecules was done; and
the stiffness of the liver of said patient (FS).

According to an alternative or complementary embodiment, the total number of (different) clinical or anatomical markers selected as additional markers is zero, one, two or three, more particularly zero, one or two, more particularly zero or one, for example, zero, for example, one, for example, two, for example, one, two or three, for example, one or two.

For example, the selected clinical or anatomical markers are one, two or three (different) markers, more particularly one or two (different) markers, for example, one marker, for example, two different markers, selected from:
the age of said patient (more particularly the age of said patient at the date when the taking of the sample of biological fluid required for the detection or quantification of the circulating molecules was done);
the BMI of said patient (more particularly the BMI of said patient at the date when the taking of the sample of biological fluid required for the detection or quantification of the circulating molecules was done); and
the stiffness of the liver of said patient (FS).

The virological characteristics (or markers) of said patient, on the other hand, are characteristics that require detection or quantification in a sample of biological fluid of said patient. Advantageously, this sample of biological fluid is the same, or at least of the same nature, as that employed to detect or quantify said circulating molecules (such as CXCL10 and HA).

Examples of virological characteristics of said patient include, in particular:
the nature of the virus(es) contained in the blood of said patient;
the viral load of said patient (VL), more particularly their viral load of hepatitis virus;
the genotype(s) of said hepatitis virus(es) with which said patient is infected.

The marker "nature of the virus(es) contained in the blood of said patient" includes, in particular, the nature of the hepatitis virus(es) contained in the blood of said patient: for example, HCV and/or HBV and/or HDV, more particularly HCV and/or HBV, more particularly HCV.

The marker "viral load of said patient" (VL) includes, in particular, the viral load of said patient in hepatitis virus, for example, their viral load in HCV and/or HBV and/or HDV, more particularly in HCV and/or HBV, more particularly in HCV.

The marker "genotype(s) of said hepatitis virus(es) with which said patient is infected" includes, in particular, the genotype(s) of said hepatitis virus(es) with which said patient is infected, for example, genotypes 1 and/or 2 and/or 3 and/or 4 and/or 5 and/or 6 and/or 7.

Examples of virological characteristics of said patient include, more particularly, the viral load of said patient in hepatitis virus, more particularly the viral load of said patient in HCV and/or HBV and/or HDV, more particularly in HCV and/or HBV, more particularly in HCV.

According to an alternative or complementary embodiment, the total number of (different) virological markers selected as additional markers is zero, one or two, more particularly zero or one, more particularly one or two, more particularly one, more particularly zero.

For example, no virological marker is selected, or else only one virological marker is selected and is the viral load of said patient (more particularly their viral load in hepatitis virus, more particularly the viral load of said patient in HCV and/or HBV and/or HDV, more particularly in HCV and/or HBV, more particularly in HCV).

According to an alternative or complementary embodiment, the total number of different additional markers selected in addition to said circulating molecules (and especially in addition to HA and CXCL10) is zero, one, two, three, four, five, or more than five.

More particularly, the total number of different additional markers as described above is zero, one, two, three, four or five, more particularly zero, one, two, three or four, more particularly zero, one, two or three, more particularly zero, one or two, more particularly zero or one, more particularly zero, more particularly one, two, three, four or five, or more than five, more particularly one, two, three, four or five, more particularly one, two, three or four, more particularly one, two or three, more particularly one or two, more particularly one, more particularly two, more particularly three, more particularly four, more particularly five.

Thus, in addition to said circulating molecules (and especially in addition to HA and CXCL10), said additional markers can comprise (or consist of), for example:
  zero, one, two or three (different) clinical or anatomical markers as described above; and
  zero or one virological marker as described above.

Thus, in addition to said circulating molecules (and especially in addition to HA and CXCL10), said additional markers can comprise (or consist of), for example:
  zero clinical or anatomical marker as described above, or else one, two or three (different) markers selected from the age, BMI and stiffness of the liver; and
  zero virological marker as described above, or else the virological marker viral load.

Selected Biological Markers:

Thus, the selected biological markers can comprise (or consist of):
  six, five, four, three or two different circulating molecules as described above, more particularly five, four, three or two circulating molecules as described above, more particularly four, three or two circulating molecules as described above, more particularly three or two circulating molecules as described above, more particularly two circulating molecules as described above, said different circulating molecules comprising at least HA and CXCL10; and
  zero, one, two, three, four or five, or more than five different additional markers selected from:
    the age of said patient (more particularly the age of said patient at the date when the taking of the sample of biological fluid required for the detection or quantification of the circulating molecules was done);
    the BMI of said patient (more particularly the BMI of said patient at the date when the taking of the sample of biological fluid required for the detection or quantification of the circulating molecules was done);
    the stiffness of the liver of said patient (FS); and
    the viral load of said patient (VL), more particularly the viral load of said patient in hepatitis virus, for example, their viral load in HCV and/or HBV and/or HDV, more particularly in HCV and/or HBV, more particularly in HCV.

The total number of different additional markers selected as above is more particularly zero, one, two, three, four or five, more particularly zero, one, two, three or four, more particularly zero, one, two or three, more particularly zero, one or two, more particularly zero or one, more particularly zero, more particularly one, two, three, four, five, or more than five, more particularly one, two, three, four or five, more particularly one, two, three or four, more particularly one, two or three, more particularly one or two, more particularly one, more particularly two, more particularly three, more particularly four, more particularly five.

Thus, the selected biological markers can comprise (or consist of):
  two different circulating molecules as described above, said two different circulating molecules consisting of HA and CXCL10; and
  zero, one, two, three, four, five, or more than five different additional markers selected from:
    the age of said patient (more particularly the age of said patient at the date when the taking of the sample of biological fluid required for the detection or quantification of the circulating molecules was done);
    the BMI of said patient (more particularly the BMI of said patient at the date when the taking of the sample of biological fluid required for the detection or quantification of the circulating molecules was done);
    the stiffness of the liver of said patient (FS); and
    the viral load of said patient (VL), more particularly the viral load of said patient in hepatitis virus, for example, their viral load in HCV and/or HBV and/or HDV, more particularly in HCV and/or HBV, more particularly in HCV.

The total number of different additional markers selected as above is more particularly zero, one, two, three, four or five, more particularly zero, one, two, three or four, more particularly zero, one, two or three, more particularly zero, one or two, more particularly zero or one, more particularly zero, more particularly one, two, three, four, five, or more than five, more particularly one, two, three, four or five, more particularly one, two, three or four, more particularly one, two or three, more particularly one or two, more particularly one, more particularly two, more particularly three, more particularly four, more particularly five.

Thus, the selected biological markers can comprise (or consist of):
  two different circulating molecules as described above, said two different circulating molecules consisting of HA and CXCL10; and
  zero, one, two or three or four different additional markers selected from:

the age of said patient (more particularly the age of said patient at the date when the taking of the sample of biological fluid required for the detection or quantification of the circulating molecules was done);

the BMI of said patient (more particularly the BMI of said patient at the date when the taking of the sample of biological fluid required for the detection or quantification of the circulating molecules was done);

the stiffness of the liver of said patient (FS); and the viral load of said patient (VL), more particularly the viral load of said patient in hepatitis virus, for example, their viral load in HCV and/or HBV and/or HDV, more particularly in HCV and/or HBV, more particularly in HCV.

The total number of different additional markers selected as above is more particularly zero, one, two or three, more particularly one, two or three, more particularly two or three, more particularly zero, one or two, more particularly zero or one, more particularly zero, more particularly one, two or three, more particularly one or two, more particularly one, more particularly two, more particularly three, more particularly four.

For example, the selected biological markers can comprise (or consist of) HA and CXCL10.

For example, the selected biological markers can comprise (or consist of) HA, CXCL10, and the age of said patient (more particularly the age of said patient at the date when the taking of the sample of biological fluid required for the detection or quantification of the circulating molecules was done).

For example, the selected biological markers can comprise (or consist of) HA, CXCL10, and the BMI of said patient (more particularly the BMI of said patient at the date when the taking of the sample of biological fluid required for the detection or quantification of the circulating molecules was done).

For example, the selected biological markers can comprise (or consist of) HA, CXCL10, and the stiffness of the liver of said patient (FS).

For example, the selected biological markers can comprise (or consist of) HA, CXCL10, and the viral load of said patient (VL), more particularly the viral load of said patient in hepatitis virus, for example, their viral load in HCV and/or HBV and/or HDV, more particularly in HCV and/or HBV, more particularly in HCV.

For example, the selected biological markers can comprise (or consist of):
HA;
CXCL10;
the age of said patient (more particularly the age of said patient at the date when the taking of the sample of biological fluid required for the detection or quantification of the circulating molecules was done); and
the BMI of said patient (more particularly the BMI of said patient at the date when the taking of the sample of biological fluid required for the detection or quantification of the circulating molecules was done).

For example, the selected biological markers can comprise (or consist of):
HA;
CXCL10;
the age of said patient (more particularly the age of said patient at the date when the taking of the sample of biological fluid required for the detection or quantification of the circulating molecules was done); and
the viral load of said patient (VL), more particularly the viral load of said patient in hepatitis virus, for example, their viral load in HCV and/or HBV and/or HDV, more particularly in HCV and/or HBV, more particularly in HCV.

For example, the selected biological markers can comprise (or consist of):
HA;
CXCL10;
the age of said patient (more particularly the age of said patient at the date when the taking of the sample of biological fluid required for the detection or quantification of the circulating molecules was done); and
the stiffness of the liver of said patient (FS).

For example, the selected biological markers can comprise (or consist of):
HA;
CXCL10;
the BMI of said patient (more particularly the BMI of said patient at the date when the taking of the sample of biological fluid required for the detection or quantification of the circulating molecules was done); and
the viral load of said patient (VL), more particularly the viral load of said patient in hepatitis virus, for example, their viral load in HCV and/or HBV and/or HDV, more particularly in HCV and/or HBV, more particularly in HCV.

For example, the selected biological markers can comprise (or consist of):
HA;
CXCL10;
the BMI of said patient (more particularly the BMI of said patient at the date when the taking of the sample of biological fluid required for the detection or quantification of the circulating molecules was done); and
the stiffness of the liver of said patient (FS).

For example, the selected biological markers can comprise (or consist of):
HA;
CXCL10;
the viral load of said patient (VL), more particularly the viral load of said patient in hepatitis virus, for example, their viral load in HCV and/or HBV and/or HDV, more particularly in HCV and/or HBV, more particularly in HCV; and
the stiffness of the liver of said patient (FS).

For example, the selected biological markers can comprise (or consist of):
HA;
CXCL10;
the age of said patient (more particularly the age of said patient at the date when the taking of the sample of biological fluid required for the detection or quantification of the circulating molecules was done);
the BMI of said patient (more particularly the BMI of said patient at the date when the taking of the sample of biological fluid required for the detection or quantification of the circulating molecules was done); and
the viral load of said patient (VL), more particularly the viral load of said patient in hepatitis virus, for example, their viral load in HCV and/or HBV and/or HDV, more particularly in HCV and/or HBV, more particularly in HCV.

For example, the selected biological markers can comprise (or consist of):
HA;
CXCL10;
the age of said patient (more particularly the age of said patient at the date when the taking of the sample of biological fluid required for the detection or quantification of the circulating molecules was done);

the BMI of said patient (more particularly the BMI of said patient at the date when the taking of the sample of biological fluid required for the detection or quantification of the circulating molecules was done); and the stiffness of the liver of said patient (FS).

For example, the selected biological markers can comprise (or consist of):

HA;

CXCL10;

the BMI of said patient (more particularly the BMI of said patient at the date when the taking of the sample of biological fluid required for the detection or quantification of the circulating molecules was done);

the viral load of said patient (VL), more particularly the viral load of said patient in hepatitis virus, for example, their viral load in HCV and/or HBV and/or HDV, more particularly in HCV and/or HBV, more particularly in HCV; and the stiffness of the liver of said patient (FS).

In the functions LOGIT, mROC and CART herein described ($LOGIT_1$ to $LOGIT_4$, $Z_1$ to $Z_{13}$, $CART_1$ to $CART_4$; cf. below), the biomarkers are more particularly as follows:

the biomarker CXCL10 is the value of quantification of circulating forms of CXCL10 in said patient, more particularly the serum concentration of CXCL10, expressed, for example, in mg/mL, µg/mL, ng/mL or µg/mL, more particularly in pg/m L;

the biomarker HA is the value of quantification of HA in said patient, more particularly may be the serum concentration of HA, expressed, for example, in mg/mL, µg/mL, ng/mL or µg/mL, more particularly in ng/mL;

the biomarker BMI is the BMI of said patient, more particularly the BMI calculated as the mass of said patient in kg divided by (the height of said patient in m)$^2$, more particularly the BMI of said patient at the date when the taking of the sample of biological fluid required for the detection or quantification of the circulating molecules CXCL10 and HA was done;

the biomarker age is the age of said patient, expressed, for example, in the number of years (whole number or with decimals), more particularly the age of said patient at the date when the taking of the sample of biological fluid required for the detection or quantification of the circulating molecules CXCL10 and HA was done;

the biomarker VL is the viral load of said patient in hepatitis virus, for example, their viral load in HCV and/or HBV and/or HDV, more particularly in HCV and/or HBV, more particularly in HCV, expressed, for example, in copies/mL, or in IU/mL, or as a multiple of one of these units, such as $10^3$ copies/mL, more particularly this load at the date when the taking of the sample of biological fluid required for the detection or quantification of the circulating molecules CXCL10 and HA was done;

the biomarker FS is the stiffness of the liver of said patient, expressed, for example, in kPA (this measurement can be done non-invasively by transient elastography, especially by FIBROSCAN™.

Detection and Quantification of the Biological Markers:

The process of the application for determining whether the liver of a patient infected with one or more hepatitis viruses and/or who is suffering from hepatitis, specifically chronic hepatitis, has not passed beyond the stage of portal fibrosis without septum, or whether they have on the contrary passed beyond this stage, comprises the step of quantifying, more particularly detecting and quantifying, the selected biological markers for this patient (cf. above).

The selected circulating molecules (comprising at least HA and CXCL10) are quantified, more particularly detected and quantified, in a sample of biological fluid of said patient.

A process of the application may thus comprise the step of taking a sample of biological fluid from said patient. However, if the process is an in vitro process, this step of taking a sample is a step that precedes the process.

A sample of biological fluid from said patient is, for example, a sample of blood, of serum, of plasma or of urine, more particularly a sample of blood, of serum, or of plasma, more particularly a sample of serum, or of plasma, more particularly a sample of serum. This sample of biological fluid can be transformed after collection. It may for example have undergone a treatment of purification and/or concentration and/or extraction, such as, for example, by purification and/or concentration and/or extraction of the serum proteins and/or polypeptides and/or peptides, or by purification and/or extraction and/or concentration of a protein fraction. The purification and/or concentration can, for example, be done by filtration and/or by a density gradient method.

The values of quantification of the circulating molecules, more particularly of HA and CXCL10, are values of concentration or proportion, more particularly values of concentration. They may be expressed in mg/mL, µg/mL, ng/mL or pg/mL. For example, the value of quantification of HA is a value of concentration expressed in ng/mL. For example, the value of quantification of CXCL10 is a value of concentration expressed in pg/mL.

These values of concentration or proportion, more particularly these values of concentration, may be those measured in said sample of biological fluid or in an extract of filtrate of this sample. For example, if the collected sample of biological fluid undergoes a treatment of purification by filtration before the measurement of said concentrations or proportions, the values of quantification may be those measured in the filtrate of purification of said biological sample. For example, if the collected sample of biological fluid is blood and if serum is prepared from this blood, the values of quantification may be those measured in the serum.

Thus, each of the values of quantification of said circulating molecules, more particularly HA and CXCL10, may be a value of concentration (or proportion) in blood, plasma or serum, more particularly in serum.

Advantageously, the values of quantification of all the selected circulating molecules, more particularly HA and CXCL10, are measured in the same sample, or at least in a sample of identical nature. For example, the values of quantification of each of the selected circulating molecules, more particularly HA and CXCL10, are all measured in a sample of serum that has not undergone any treatment after collection, or else are all measured in a sample of serum that has undergone the same treatment after collection (for example, the same treatment of purification).

Advantageously, the values of quantification of all the selected circulating molecules, more particularly HA and CXCL10, can be measured in an undiluted sample of serum.

Advantageously, the values of quantification of all the selected circulating molecules, more particularly HA and CXCL10, can be measured in one and the same biological sample, more particularly in one and the same sample of serum, more particularly in one and the same undiluted sample of serum.

In the process of the application, said step of quantification may, in particular, comprise in vitro detection of each of the circulating molecules selected as biological markers, such as HA and CXCL10.

According to an advantageous embodiment, the detection of each of the circulating molecules selected as biological markers, more particularly HA and CXCL10 (for the purpose of quantification), is done in multiplex detection (simultaneous detection in one and the same sample of biological fluid); cf. Example 10 below. Certain markers of the prior art, such as A2M, have a very high serum concentration: their quantification thus cannot be done in multiplex detection with markers whose serum concentration is much lower, such as HA and CXCL10. The combinations of biomarkers described in the application on the other hand allow for multiplex performance.

For the quantification, more particularly detection and quantification, of each of the circulating molecules selected as biological markers, such as HA and CXCL10, a ligand specific of this circulating molecule can be used. This ligand can directly bear a detection marker (such as a chemiluminescent marker or fluorophor). This ligand can be used as a capture ligand and/or detection ligand.

This ligand can, for example, be an organic molecule or complex, or an inorganic molecule or complex. For example, this ligand may be a protein (more particularly an antibody, more particularly a monoclonal antibody or a polyclonal antibody), a polysaccharide, a lipid, or a complex of protein(s) and/or polysaccharide(s) and/or lipid(s).

For the quantification, more particularly detection and quantification, of HA in the biological fluid, proteins that bind specifically to HA, such as an anti-HA antibody (polyclonal or monoclonal), or such as the recombinant human protein aggrecan [protein G1-IGD-G2 commercially available from the company R&D SYSTEMS, Inc. (614 McKinley Place NE; Minneapolis, Minn. 55413; USA), under the catalogue reference 1220-PG-025], may be used as ligands.

For the quantification, more particularly detection and quantification, of CXCL10 in the biological fluid, i.e., of circulating forms of CXCL10, an antibody or antibodies (polyclonal or monoclonal) can be used as ligands. This antibody (or these antibodies) can bind specifically to one, more or all the circulating forms of CXCL10. For example, an antibody (polyclonal or monoclonal) may be employed that binds specifically to one, more or all the proteins of SEQ ID NOS: 4 to 9, more particularly to all the proteins of SEQ ID NOS: 4 to 9 [for example, monoclonal mouse anti-human CXCL10 antibody, commercially available from R&D SYSTEMS, Inc. (614 McKinley Place NE; Minneapolis, Minn. 55413; USA), under the catalogue reference MAB266 (clone 33036, class IgG1)].

If the biological markers further comprise one or more additional markers that are not circulating molecules, more particularly that are not human circulating molecules (cf. above), this or these additional markers are also quantified.

The value of quantification of this, or each of these, additional markers can be determined by measuring it or collecting it for or on said patient, for example, by collecting the value of quantification of this, or each of these, additional markers measured in advance for or on said patient.

For example, if this (these) additional marker(s) is (include) the marker age, the value of quantification of this marker can be determined (or determined in advance) by collecting the value of the age of said patient [for example, a value expressed in number of years (whole number or with decimals)].

For example, if this (these) additional marker(s) is (include) the marker sex, the value of quantification of this marker can be determined (or determined in advance) by assigning a value of quantification to the nature (female or male) of the sex of said patient [for example, a value of 0 for a female sex, and a value of 1 for a male sex].

For example, if this (these) additional marker(s) is (include) the marker body mass index, the value of quantification of this marker can be determined (or determined in advance) on said patient by measuring the mass and height of said patient (for example, by measuring the height in m and the mass in kg), in order to calculate the ratio of mass to the square of the height [BMI=mass divided by (height)$^2$, more particularly mass in kg divided by (height in meters)$^2$].

For example, if this (these) additional marker(s) is (include) the marker viral load, the value of quantification of this marker can be determined (or determined in advance) by measuring in vitro the value of the load or concentration of hepatitis virus (more particularly of HCV and/or HCV and/or HDV, more particularly HCV) in a sample of biological fluid obtained in advance from said patient (human), more particularly by measuring in vitro the value of the quantity of hepatitis virus in a sample of biological fluid obtained in advance from said patient (human) and determining the value of this viral load or concentration. The value of this load of hepatitis virus can, for example, be expressed in copies/mL, or in IU/mL, or as a multiple of one of these units, such as $10^3$ copies/mL.

The value of this or of each of these additional markers is advantageously the value of said marker at the date when said biological fluid was collected for in vitro measuring the concentrations of each of said (human) circulating molecules, more particularly at the date when said biological fluid was collected for in vitro measuring the concentrations of HA and of the protein CXCL10.

Determination of the Stage of Hepatic Fibrosis from the Values of Quantification of the Biological Markers The values of quantification of the selected biological markers (especially those of HA and CXCL10) are compared to their values, or to the distribution of their values, in the predefined reference cohorts according to the stage of hepatic fibrosis, in order to classify said patient into the one of these reference cohorts to which they most probably belong.

Said reference cohorts include or are:
- a first reference cohort in which the stage of hepatic fibrosis of the individuals does not pass beyond said stage of mild fibrosis (i.e., a first reference cohort in which the stage of hepatic fibrosis of the individuals does not pass beyond that of the stages of hepatic fibrosis that show a score F1 according to the Metavir fibrosis scores system); and
- a second reference cohort in which the stage of hepatic fibrosis of the individuals passes beyond said stage of mild fibrosis (i.e., a second reference cohort in which the stage of hepatic fibrosis of the individuals passes beyond that of the stages of hepatic fibrosis that show a score F1 according to the Metavir fibrosis scores system).

In other words, the values of quantification of the selected biological markers (especially those of HA and CXCL10) are compared to a predetermined reference value (cut-off or threshold) for the classification of said patient into either the first cohort or the second cohort.

Classification into the first cohort determines or indicates that the stage of hepatic fibrosis of said patient does not pass beyond the stage of portal fibrosis without septum.

Classification into the second cohort determines or indicates that the stage of hepatic fibrosis of said patient passes beyond the stage of portal fibrosis without septum.

According to an aspect of the application, the individuals of said reference cohorts are individuals of the same species as said patient [for example, humans of said patient is human], and are infected with one or more hepatitis viruses that belong to different genotypes.

For example, the individuals of said reference cohorts are humans infected with HCV, and the HCV strains of these individuals belong to at least two different genotypes, more particularly at least three, more particularly at least four, more particularly at least five, more particularly at least six, more particularly at least seven, different genotypes.

For example, the individuals of said reference cohorts are humans infected with HCV, and the HCV strains of these individuals belong to at least four different genotypes including the genotypes 1, 2, 3 and 4.

For example, the individuals of said reference cohorts are humans infected with HCV, and the HCV strains of these individuals belong to at least five different genotypes including the genotypes 1, 2, 3, 4 and 5.

For example, the individuals of said reference cohorts are humans infected with HCV, and the HCV strains of these individuals belong to at least six different genotypes including the genotypes 1, 2, 3, 4, 5 and 6.

The individuals of said first reference cohort include at least individuals whose stage of hepatic fibrosis is that of a fibrosis without septum (score F1 according to the Metavir fibrosis scores system).

The individuals of said first reference cohort can thus be comprised of individuals whose stage of hepatic fibrosis is that of a portal fibrosis without septum [score F1 according to the Metavir fibrosis scores system].

The individuals of said first reference cohort can thus be comprised of individuals whose stage of hepatic fibrosis is that of a portal fibrosis without septum and of individuals infected with one or more hepatitis viruses and/or who are suffering from hepatitis (specifically chronic hepatitis), but who do not have hepatic fibrosis [scores F0 and F1 according to the Metavir fibrosis scores system].

The individuals of said second reference cohort include at least individuals whose stage of hepatic fibrosis is that of a portal fibrosis with septum(s) (score F2 according to the Metavir fibrosis scores system).

The individuals of said second reference cohort can be comprised of individuals whose stage of hepatic fibrosis is that of a portal fibrosis with septum [score F2 according to the Metavir fibrosis scores system].

The individuals of said second reference cohort can be comprised of individuals whose stage of hepatic fibrosis is that of a portal fibrosis with septums and of individuals whose stage of hepatic fibrosis is that of a septal fibrosis without cirrhosis [scores F2 and F3 according to the Metavir fibrosis scores system].

The individuals of said second reference cohort can be comprised of individuals whose stage of hepatic fibrosis is that of a portal fibrosis with septums, of individuals whose stage of hepatic fibrosis is that of a septal fibrosis without cirrhosis, and of individuals whose stage of hepatic fibrosis is that of a cirrhosis [scores F2, F3 and F4 according to the Metavir fibrosis scores system].

The total number of individuals who form said first reference cohort and said second reference cohort may be at least 100, more particularly at least 200, advantageously at least 300.

Each of these two cohorts is comprised of a plurality of individuals and represents 30% to 70% of the overall population of the individuals (the total of the individuals of said first reference cohort and said second reference cohort being 100%). For example, the number of individuals constituting said first reference cohort and said second reference cohort make a total of 100, said first reference cohort is comprised of 30 individuals, and said second reference cohort is comprised of 70 individuals.

More particularly, each of these two cohorts is comprised of a plurality of individuals and represents 40% to 60% of the overall population of the individuals, more particularly 40% to 55%, more particularly 45% to 55%, more particularly 45% to 50% of the overall population of the individuals (the total of the individuals of said first reference cohort and said second reference cohort being 100%). For example, the number of individuals constituting said first reference cohort and said second reference cohort make a total of more than 300, and said first reference cohort is comprised of a number of individuals representing 40% to 60% of this overall population of more than 300 individuals (said second reference cohort is thus comprised of a number of individuals representing the complementary percentage to make a total of 100%).

A process of the application is thus a process (in vitro) for determining (more particularly for determining with a high probability) whether the stage of hepatic fibrosis of a (human) patient infected with one or more hepatitis viruses and/or who is suffering from hepatitis, specifically chronic hepatitis, has not passed beyond the stage of mild fibrosis, or whether they have on the contrary passed beyond this stage, said stage of mild fibrosis being that of a portal fibrosis without septum (according to the Metavir fibrosis scores system, the stage of a portal fibrosis without septum is a score F1), said process comprising the following steps:

i) in a sample of biological fluid obtained in advance from said (human) patient, measuring the quantities of several (human) circulating molecules in said sample to obtain the value of the concentration of each of said circulating molecules, said (human) circulating molecules comprising or consisting of hyaluronic acid (HA) and the protein CXCL10 (cf. "Circulating molecules", "Selected biological markers", and "Detection and quantification of the biological markers" above);

ii) comparing the thus obtained values of concentrations for each of said circulating molecules to their values, or to the distribution of their values, in the predefined reference cohorts according to the stage (or degree) of hepatic fibrosis, in order to classify said patient into the one of these reference cohorts to which they most probably belong, said reference cohorts including or being:

a first reference cohort in which the stage of hepatic fibrosis of the individuals does not pass beyond said stage of mild fibrosis; and a second reference cohort in which the stage of hepatic fibrosis of the individuals passes beyond said stage of mild fibrosis;

classification into said first cohort indicating that the stage of hepatic fibrosis of said patient has not passed beyond the stage of portal fibrosis without septum;

classification into said second cohort indicating that the stage of hepatic fibrosis of said patient has passed beyond the stage of portal fibrosis without septum.

More particularly, a process of the application is a process (in vitro) for determining (more particularly for determining with a high probability) whether the stage of hepatic fibrosis of a (human) patient infected with one or more hepatitis viruses and/or who is suffering from hepatitis, specifically chronic hepatitis, has not passed beyond the stage of mild fibrosis, or whether they have on the contrary passed beyond this stage, said stage of mild fibrosis being that of a portal fibrosis without septum (according to the Metavir fibrosis scores system, the stage of a portal fibrosis without septum is a score F1), said process comprising the following steps:
i) selecting different biological markers (or variables), the selected different biological markers (or variables) comprising or consisting of:
  a) different (human) circulating molecules, said different (human) circulating molecules comprising or consisting of HA and CXCL10 (cf. "Circulating molecules", "Selected biological markers", and "Detection and quantification of the biological markers" above); and
  b) zero, one, two, three or four additional markers from the list of markers comprised of the age, body mass index (BMI), viral load (VL) and the stiffness of the liver (FS) (cf. "Optional additional markers", "Selected biological markers", and "Detection and quantification of the biological markers" above);
ii) quantifying the different biological markers (or variables) selected in step i) by measuring in vitro the concentrations of each of said (human) circulating molecules of step i)a) above in a sample of biological fluid obtained in advance from said patient, more particularly by measuring in vitro the quantities of each of said (human) circulating molecules of step i)a) above in a sample of biological fluid obtained in advance from said (human) patient to determine the value of the concentration of each of said circulating molecules [in said sample and/or in said patient]; and
when one, two, three, four or five additional markers are selected from said list of step i)b) above, and when this (or these) additional marker(s) is (are) or includes (include) one or more markers selected from the age, body mass index and stiffness of the liver: by collecting the value of quantification of this or each of these additional markers that was determined in advance for or on said patient;
when one, two, three, four or five additional markers are selected from said list of step i)b) above, and when this (or these) additional marker(s) is (are) or includes (include) the viral load: by measuring this viral load in vitro in a sample of biological fluid obtained in advance from said patient, or by collecting the value of this viral load that was determined in advance for said patient;
iii) comparing the values of quantification obtained in step ii) to their values, or to the distribution of their values, in the predefined reference cohorts according to the stage (or degree) of hepatic fibrosis, in order to classify said patient into the one of these reference cohorts to which they most probably belong, said reference cohorts including or being:
  a first reference cohort in which the stage of hepatic fibrosis of the individuals does not pass beyond said stage of mild fibrosis; and
  a second reference cohort in which the stage of hepatic fibrosis of the individuals passes beyond said stage of mild fibrosis;
classification into said first cohort indicating that the stage of hepatic fibrosis of said patient has not passed beyond the stage of portal fibrosis without septum;
classification into said second cohort indicating that the stage of hepatic fibrosis of said patient has passed beyond the stage of portal fibrosis without septum.

In said step i)b), there are more particularly selected zero, one, two or three additional markers selected from the list of markers consisting of the age, body mass index (BMI), viral load (VL) and stiffness of the liver (FS) from this list (cf. "Optional additional markers" above).

For example, no additional marker is selected, or the additional marker stiffness of the liver, or the additional markers age and BMI, or the additional markers age, BMI and viral load are selected.

Thus, the different biological markers selected in step i) may, for example, comprise or consist of:
  hyaluronic acid (HA) and the protein CXCL10, or
  hyaluronic acid (HA), the protein CXCL10, the age and the BMI, or
  hyaluronic acid (HA), the protein CXCL10, the age, the BMI, and the viral load (VL), or
  hyaluronic acid (HA), the protein CXCL10, and the stiffness of the liver (FS);
cf. "Circulating molecules", "Optional additional markers", "Selected biological markers", and "Detection and quantification of the biological markers" above.

Said step of comparing the values of quantification of the biological markers to their values, or to the distribution of their values, in the predefined reference cohorts according to the stage (or degree) of hepatic fibrosis, in order to classify said patient into the one of these reference cohorts to which they most probably belong, can be realized by any means that the skilled person considers appropriate.

In particular, this comparison can be done by classification, more particularly by combining the determined (or measured) values obtained for said patient in a classification model, more particularly in a multivariate classification model.

Such a classification model compares (in a combined manner) the determined values obtained for said patient to their values, or to the distribution of their values, in the predefined reference cohorts according to the stage of hepatic fibrosis, in order to classify said patient into the one of these reference cohorts to which they most probably belong, for example, by attributing to them an output value indicating the hepatic fibrosis score of said patient.

Such a classification model can be created, especially created in advance, by making a comparison between the cohorts of the determined values obtained for said reference cohorts, or the distribution of these determined values.

More particularly, such a classification model can be created, especially created in advance, by measuring or collecting the values of quantification of the biological markers in reference cohorts predefined according to their score of hepatic fibrosis, and by analyzing these determined values, or the distribution thereof, by a statistical method for creating a classification model, more particularly a multivariate classification model, which induces or determines a score of hepatic fibrosis from said values of quantification.

A classification model can, for example, be created (in advance) by:
  constituting at least two reference cohorts created in advance according to the stage (or degree or score) of hepatic fibrosis;
    a first reference cohort consisting of individuals in which the stage of hepatic fibrosis does not pass beyond said stage of mild fibrosis, and
    a second reference cohort consisting of individuals in which the stage of hepatic fibrosis passes beyond said stage of mild fibrosis (cf. "Determination of the stage of hepatic fibrosis from values of quantification of biological markers" above);
  quantifying each of said selected different biological markers in said first reference cohort and in said second reference cohort;

comparison (mathematical and/or statistical) of the values of quantification shown by said markers in the first reference cohort to those they show (respectively) in the second reference cohort.

More particularly, said classification model can be created (in advance) as follows:

α) for a population of individuals of the same species as said patient, infected with the same hepatitis virus(es) as said patient, determining the stage (or degree or score) of hepatic fibrosis of each of said individuals of the population, and classifying them into subpopulations according to their stage (or degree or score) of hepatic fibrosis, thus constituting the reference cohorts created according to their stage (or degree or score) of hepatic fibrosis, said reference cohorts including or being:

a first reference cohort in which the stage (or degree or score) of hepatic fibrosis of the individuals does not pass beyond the stage of portal fibrosis without septum (i.e., does not pass beyond the Metavir fibrosis score F1); and a second reference cohort in which the stage (or degree or score) of hepatic fibrosis of the individuals passes beyond the stage of portal fibrosis without septum (i.e., passes beyond the Metavir fibrosis score F1);

β) for each of said individuals, quantifying the different biological markers selected in step i) of claim 1; and γ) making a comparison between the cohorts of the values of quantification obtained in step β), or the distribution of these values, to create a classification model that, from the values of quantification of said selected biological markers (more particularly, from a combination of these values), induces classification into one of said reference cohorts.

Said step of comparison can be realized by classifying the values of quantification obtained for said patient in a classification model, more particularly, a multivariate classification model, in order to assign to said patient a score (Z) indicating whether or not the stage (or degree) of the hepatic fibrosis of said patient has passed beyond the stage of mild fibrosis.

Said classification model can be a model that, from a combination of the values of quantification of said biological markers, induces a score value (Z) from the combination of the values of quantification of said selected biological markers.

More particularly, said step of comparison can be realized by applying a predetermined discriminating classification rule to the values of quantification obtained for said patient, in order to classify said patient into the one of said reference cohorts to which they most probably belong (more particularly, in order to classify said patient into said first reference cohort or into said second reference cohort).

This discriminating rule can be a rule that compares the values of quantification obtained for the selected biological markers to one or more threshold values predetermined by classification, in order to classify said patient into the one of said reference cohorts to which they most probably belong (i.e., in order to classify said patient into said first reference cohort or into said second reference cohort).

For example, a model can be created by a mathematical function, a non-parametric technique, a procedure of heuristic classification, or else an approach of probabilistic prediction. A typical example of classification based on the quantification of biological markers consists in the discrimination of "healthy" versus "sick" patients. The formalization of this problem consists in m independent samples, described by n random variables. Each individual i (i=1, . . . , m) is characterized by a vector $x_i$ describing the n characteristic values: $x_{ij}$, i=1, . . . , m, j=1, . . . , n. These characteristic values can for example represent values of protein concentrations and/or of clinical and/or anatomical data and/or of virological data. Each sample $x_i$ is associated to a discrete value $y_i$, representing the clinical status of individual i. By means of example, $y_i$=0 if the patient i has a score of hepatic fibrosis F1, $y_i$=1 if the patient i has a score of hepatic fibrosis F2. A model offers a discriminating rule (for example, a mathematical function, an algorithm or procedure), which uses the information available from $x_i$ for predicting $y_j$ in each sample observed. The objective is to use this model in order to predict the clinical status of patient p, namely $y_p$, from available biological and/or clinical values, namely $x_p$.

Different classification models are known to the skilled person (cf. Hastie, Tibishirani and Friedman, 2009; Falissard, 2005; Theodoridis and Koutroumbos 2009). The discriminating rules of the multivariate classification models can, for example, be based on a mathematical formula of the type $y=f(x_1, x_2, \ldots, x_n)$, where f is a linear or non-linear mathematical function (logistic regression, mROC, for example), or on an algorithm of machine learning or of artificial intelligence whose characteristics consist in a series of control parameters identified as being the most efficient for the discrimination of the patients (for example, KNN, WKNN, SVM, RF). Each classification model that the skilled person considers appropriate may be used or employed.

According to the application, said discriminating classification rule can be, for example:
  a method of statistical analysis, more particularly of multivariate statistical analysis, for example:
    an ROC (receiver operating characteristics) method;
    a linear or non-linear mathematical function, especially a linear mathematical function, such as a function generated by the mROC (multivariate ROC) method, or
    a linear or non-linear regression method, such as logistic regression, more particularly logistic regression using an affine function (LOGIT);
    a PLS-DA (partial least squares—discriminant analysis) method;
    an LDA (linear discriminant analysis) method;
  a classification method by learning or artificial intelligence, for example, a learning or artificial intelligence algorithm, a non-parametric or heuristic classification method or probabilistic prediction method, such as:
    a decision tree, such as the CART (classification and regression tree) method; or
    a method of the boosting type based on binary classificators (from Adaboost) or a method related to boosting (bagging); or
    a method of k-nearest neighbors (or KNN), or more generally the method of weighted k-nearest neighbors (or WKNN); or
    a method (for example, an algorithm) of support vector machines (or SVM); or
    a random forest (or RF); or
    a Bayesian network; or
    a neural network; or
    a Galois lattice (or formal concept analysis).

The multivariate ROC method (mROC) is a generalization of the ROC (receiver operating characteristics) method (cf. Reiser and Faraggi 1997; Su and Liu 1993, Shapiro, 1999). It calculates the area under the ROC curve (AUC) relative to a linear combination of biomarkers and/or of transformations of biomarkers (in the case of a normalization) under the assumption of a multivariate normal distribution. The mROC method was described, in particular, in Kramar et al. 1999 and Kramar et al. 2001. The software mROC version 1.0, commercially available from the developers (A. Kramar, A. Fortune, D. Farragi and B. Reiser), for example, can be used to create an mROC model. Andrew Kramar and Antoine Fortune can be contacted via the Unité de Biostatistique du Centre Regional de Lutte contre le Cancer (CRLC) Val d'Aurelle—Paul Lamarque (208, rue des Apothicaires; Parc Euromédecine; 34298 Montpellier Cedex 5; France). David Faraggi and Benjamin Reiser can be contacted via the Department of Statistics of the University of Haifa (Mount Carmel; Haifa 31905; Israel). An mROC model can take the form of a linear function of the type $Z=a(BMQ_1)+b(BMQ_2)+ \ldots +w(BMQ_n)$, with BMQ=biomarker, n being the number of biomarkers BMQ, $BMQ_i$ being the value of quantification of one of the selected biomarkers (i going from 1 to n) or the value of the Box-Cox transformed form of this value of quantification [Box and Cox 1964: for a biomarker BMQ, the Box-Cox transformed form of the value of quantification of BMQ is $BMQ^t$, which is equal to $(BMQ^{\lambda}-1)/\lambda$], and with a, b, ... and w being the parameters of the mROC function.

The logistic regression (LR) using an affine function or LOGIT function is a model of binomial regression (Berkson 1944; Berkson 1951). A model of logistic regression can take the form of an affine function of the type $LOGIT=Intercept+k(BMQ_1)+l(BMQ_2)+ \ldots +w(BMQ_n)$, with BMQ=biomarker, n being the number of biomarkers BMQ, $BMQ_i$ being the value of quantification of one of the selected biomarkers (i going from 1 to n), and Intercept, k, l, ... and z are the parameters of the LOGIT function.

The family of artificial intelligence or machine learning methods is a family of algorithms that, instead of proceeding to an explicit generalization, compare the examples of a new problem with the examples considered while learning that have been stored in the memory. These algorithms directly create hypotheses from learnt examples themselves.

An example of this type of algorithm is the algorithm CART, an acronym meaning "classification and regression trees" (Breiman 1984). A CART model is a decision tree. An example thereof is presented in FIG. 12. The value of quantification of each of the biomarkers ($BMQ_i$) is compared to a series of threshold values (parameters h, i and j in FIG. 12), which allows to classify the tested sample by following the decision tree (in FIG. 12: score <F2, or score F2).

Another example of this type of algorithm is the algorithm of k-nearest neighbors (KNN), and one of its possible extensions is known under the name algorithm of weighted k-nearest neighbors (WKNN) (Hechenbichler and Schliep, 2004). In the context of classification of a new observation x, the simple basic idea is to let the nearest neighbors of this observation vote. The class (or clinical status) of x is determined as a function of the majority class among the k nearest neighbors of the observation x. Libraries of specific KKNN functions are available, for example, in the software R (http://www.R-project.org/). The software R was initially developed by John Chambers and the Bell laboratories (cf. Chambers 2008). The current version of this software suite is the version 2.11.1. The source code is freely available under the regulations of the General Public License "Free Software Foundation's GNU" on the website http://www.R-project.org/. This software can be used to create a WKNN model.

A random forest (RF) is constituted of a set of simple forecast trees, each being capable of producing a response when presented a subset of predictors (Breiman 2001; Liaw and Wiener 2002). The calculations are realized with the software R. This software can be used to create RF models.

A neural network is constituted of a directed weighted graph whose nodes symbolize the neurons. The network is built from examples of each class (for example, F2 versus F1) and is then used to determine to which class a new element belongs; cf. Intrator and Intrator 1993, Riedmiller and Braun 1993, Riedmiller 1994, Anastasiadis et. al. 2005; cf. http://cran.r-project.org/web/packages/neuralnet/index-.html. The software R freely available on http://www.r-project.org/(version 1.3 of Neuralnet, written by Stefan Fritsch and Frauke Guenther, following the work by Marc Suling), for example, can be used to build a network of neurons.

In accordance with the application, the comparison of values of quantification of the selected biomarkers to their values, or to the distribution of their values, in reference cohorts predefined according to the stage of hepatic fibrosis for classifying said patient into the one of these reference cohorts to which they most probably belong can thus be realized, in particular, by following a method and/or by using an algorithm or a software:
which is based on a mathematical function, such as, for example:
a linear function (for example, an mROC function), or
a non-linear function, such as, for example, an affine function (for example, a logistic regression LOGIT), or
which is not based on a mathematical function, such as, for example, a method, a software or an algorithm of learning or artificial intelligence (for example, a decision tree CART).

More particularly, said comparison can thus be realized, in particular, by following a method and/or by using an algorithm or a software:
mROC
of logistic regression (more particularly of logistic regression using a LOGIT affine function);
KNN, WKNN (more particularly WKNN),
RF, or
NN, or
CART,
more particularly mROC, logistic regression (more particularly logistic regression using a LOGIT affine function) or CART.

Each of these algorithms, software or methods allows to build a classification model from values of quantification of each of said reference cohorts, and to combine the values of quantification obtained on said patient in this model to induce therefrom the classification or score of hepatic fibrosis of said patient.

The inventors demonstrate that the synergistic effect observed with the combination CXCL10 and HA does not depend on the fact that an mROC function is employed for the classification of the patient; cf. the following Examples, especially:
Example 7, more particularly Tables 20, 21 and 23,
Example 8, more particularly Table 24.

According to one embodiment, the classification model employed is a multivariate classification model using a mathematical function, such as mROC, or logistic regression (more particularly logistic regression using a LOGIT affine function).

According to an alternative or complementary embodiment, the classification model employs a machine learning or artificial intelligence model, such as CART.

Performances (Sensitivity, NPV, Specificity, NPV, Correct Classification Rate, AUC)

The means of the application, more particularly the selection of the biological markers of the application, allow to achieve very good performances of classification of said patient.

Thus, due to the means of the application, said comparison of the values of quantification of said patient to their values, or to the distribution of their values, in said reference cohorts is performed by classifying said patient into the one of these reference cohorts to which they most probably belong, with a particularly high sensitivity (Se) and/or negative predictive value (NPV) and/or specificity (Spe) and/or positive predictive value (PPV) and/or area under the ROC curve (AUC) and/or correct classification rate (CCR).

The terms sensitivity (Se), specificity (Spe), positive predictive value (PPV), negative predictive value (NPV), area under the ROC curve (AUC) and correct classification rate (CCR) have the meanings according to their usual meanings in the field. For the record:

$Se=TP/(TP+FN)$, with $TP$=number of true positives and $FN$=number of false negatives;

$Sp=TN/(TN+FP)$, with $TN$=number of true negatives and $FP$=number of false positives;

$PPV=TP/(TP+FP)$ with $TP$=true positives and $FP$=false positives;

$NPV=TN/(TN+FN)$, with $TN$=true negatives and $FN$=false negatives; with positive test=said stage of mild fibrosis has been passed negative test=said stage of mild fibrosis has not been passed.

PPV thus represents the probability that the tested subject has actually passed beyond said stage of mild fibrosis (Metavir hepatic fibrosis score of at least F2), knowing that the means of the application indicate that they have passed beyond said stage of mild fibrosis (Metavir hepatic fibrosis score of at least F2) [positive result of the test].

NPV thus represents the probability that the tested subject actually has not passed beyond said stage of mild fibrosis (Metavir hepatic fibrosis score of at most F1), knowing that the means of the application indicate that they have not passed beyond said stage of mild fibrosis (Metavir hepatic fibrosis score of at least F2) [negative result of the test].

The correct classification rate is the percentage of correctly classified patients.

The area under the ROC curve (AUC) is the area under the ROC curve (AUC) relative to a linear combination of biomarkers and/or of transformations of biomarkers (in the case of a normalization) under the assumption of a multivariate normal distribution.

Said comparison of values of quantification of said patient to their values, or to the distribution of their values, in said reference cohorts can be done by following a classification model as described above.

More particularly, said comparison can be done according to an mROC function, a LOGIT function or a CART tree, especially a $Z_1$ to $Z_{13}$ mROC function, a $LOGIT_1$ to $LOGIT_4$ function, a $CART_1$ to $CART_4$ tree, as described below.

In accordance with the application, said comparison is done (for example by mROC, logistic regression or CART tree) by classifying said patient with a sensitivity (Se) of at least 70%, at least 75%, at least 76%, at least 77%, at least 78%, at least 80%, at least 82% or at least 83%.

More particularly, said comparison can be done (for example by mROC, logistic regression or CART tree) by classifying said patient with a sensitivity (Se) of at least 76%, at least 77%, at least 78%, at least 80%, at least 82% or at least 83%.

According to an alternative or complementary embodiment, said comparison is done (for example by mROC, logistic regression or CART tree) by classifying said patient with a negative predictive value (NPV) of at least 70%, at least 75%, at least 76%, at least 77%, at least 78%, at least 80%, at least 81%, at least 82% or at least 83%.

More particularly, said comparison is done (for example by mROC, logistic regression or CART tree) by classifying said patient with a negative predictive value (NPV) of at least 75%, at least 76%, at least 77%, at least 78%, at least 80%, at least 81%, at least 82% or at least 83%.

According to an alternative or complementary embodiment, said comparison is done (for example by mROC, logistic regression or CART tree) by classifying said patient with a specificity of at least 59%, at least 70%, at least 71%, at least 80%, at least 85%, at least 86%, at least 87%, at least 89%, at least 90% or at least 91%.

More particularly, said comparison is done (for example by mROC, logistic regression or CART tree) by classifying said patient with a specificity of at least 85%, at least 86%, at least 87%, at least 89%, at least 90% or at least 91%.

According to an alternative or complementary embodiment, said comparison is done (for example by mROC, logistic regression or CART tree) by classifying said patient with a positive predictive value (PPV) of at least 54%, at least 61%, at least 62%, at least 85%, at least 86%, at least 87%, at least 88%, at least 90% or at least 91%.

More particularly, said comparison is done (for example by mROC, logistic regression or CART tree) by classifying said patient with a positive predictive value (PPV) of at least 85%, at least 86%, at least 87%, at least 88%, at least 90% or at least 91%.

All combinations of minimum value of sensitivity and/or of NPV and/or of specificity and/or of PPV are explicitly included in the description of the application.

Thus, according to an alternative or complementary embodiment, said comparison is done (for example by mROC, logistic regression or CART tree) by classifying said patient with a sensitivity (Se) of at least 76% (as described above) and/or with a negative predictive value (NPV) of at least 75% (as described above).

According to an alternative or complementary embodiment, said comparison is done (for example by mROC, logistic regression or CART tree) by classifying said patient with a sensitivity (Se) of at least 76% (as described above) and/or with a specificity (Spe) of at least 59% (as described above).

According to an alternative or complementary embodiment, said comparison is done (for example by mROC, logistic regression or CART tree) by classifying said patient with a sensitivity (Se) of at least 76% (as described above) and/or with a specificity (Spe) of at least 85% (as described above).

According to an alternative or complementary embodiment, said comparison is done (for example by mROC, logistic regression or CART tree) by classifying said patient with a sensitivity (Se) of at least 76% (as described above) and/or with a PPV of at least 54% (as described above).

According to an alternative or complementary embodiment, said comparison is done (for example by mROC, logistic regression or CART tree) by classifying said patient with a sensitivity (Se) of at least 76% (as described above) and/or with a PPV of at least 85% (as described above).

According to an alternative or complementary embodiment, said comparison is done (for example by mROC, logistic regression or CART tree) by classifying said patient with a specificity (Spe) of at least 54% (as described above) and/or with a PPV of at least 54% (as described above).

According to an alternative or complementary embodiment, said comparison is done (for example by mROC, logistic regression or CART tree) by classifying said patient with a specificity (Spe) of at least 54% (as described above) and/or with a PPV of at least 85% (as described above).

According to an alternative or complementary embodiment, said comparison is done (for example by mROC, logistic regression or CART tree) by classifying said patient with a specificity (Spe) of at least 85% (as described above) and/or with a PPV of at least 54% (as described above).

According to an alternative or complementary embodiment, said comparison is done (for example by mROC, logistic regression or CART tree) by classifying said patient with a specificity (Spe) of at least 85% (as described above) and/or with a PPV of at least 85% (as described above).

According to an alternative or complementary embodiment, said comparison is done (for example by mROC, logistic regression or CART tree) by classifying said patient with a specificity (Spe) of at least 54% (as described above) and/or with an NPV of at least 75% (as described above).

According to an alternative or complementary embodiment, said comparison is done (for example by mROC, logistic regression or CART tree) by classifying said patient with a specificity (Spe) of at least 85% (as described above) and/or with an NPV of at least 75% (as described above).

According to an alternative or complementary embodiment, said comparison is done (for example by mROC, logistic regression or CART tree) by classifying said patient with an NPV of at least 75% (as described above) and/or with a PPV of at least 54% (as described above).

According to an alternative or complementary embodiment, said comparison is done (for example by mROC, logistic regression or CART tree) by classifying said patient with an NPV of at least 75% (as described above) and/or with a PPV of at least 85% (as described above).

Thus, according to an alternative or complementary embodiment, said comparison is done (for example by mROC, logistic regression or CART tree) by classifying said patient with a sensitivity (Se) of at least 76% (as described above) and with an NPV of at least 75% (as described above), as well as with:

a specificity (Spe) of at least 85%, and/or
a PPV of at least 85%.

Due to the means of the application, said comparison can be done (for example by mROC or logistic regression) by classifying said patient with an area under the ROC curve (AUC) of at least 0.700, at least 0.704, at least 0.720, at least 0.729, at least 0.730, at least 0.731, at least 0.840, at least 0.844, at least 0.860, at least 0.865, at least 0.868, at least 0.880, at least 0.882, at least 0.890, at least 0.895, at least 0.898, at least 0.899, at least 0.0900, at least 0.910, at least 0.920, at least 0.921, at least 0.930, at least 0.931, or at least 0.933.

In fact, the combination of the two only markers HA and CXCL10 is sufficient to achieve an AUC of at least 0.700, more particularly at least 0.704, more particularly at least 0.865 (cf. the Examples below).

More particularly, said comparison can be done, for example by mROC or logistic regression, by classifying said patient with an AUC of at least 0.800, more particularly at least 0.865, at least 0.868, at least 0.880, at least 0.882, at least 0.890, at least 0.895 or at least 0.898.

Due to the means of the application, said comparison can be done (for example by mROC, logistic regression or CART tree) by classifying said patient with a correct classification rate (CCR) of at least 60%, at least 66%, at least 70%, at least 72%, at least 73%, at least 75%, at least 77%, at least 80%, at least 81%, at least 82%, at least 83%, at least 85%, at least 86%, at least 88% or at least 89%.

More particularly, said comparison can be done (for example by mROC, logistic regression or CART tree) by classifying said patient with a correct classification rate (CCR) of at least 80%, at least 81%, at least 82%, at least 83%, at least 85%, at least 86%, at least 88% or at least 89%.

All combinations of minimum value of sensitivity and/or of NPV and/or of specificity and/or of PPV are explicitly included in the description of the application.

Thus, according to an alternative or complementary embodiment, said comparison is done (for example by mROC, logistic regression or CART tree) by classifying said patient with a correct classification rate of at least 80% and/or with an AUC of at least 0.704.

According to an alternative or complementary embodiment, said comparison is done (for example by mROC, logistic regression or CART tree) by classifying said patient with a correct classification rate of at least 70% and/or with an AUC of at least 0.800, more particularly with a correct classification rate of at least 80% and/or with an AUC of at least 0.800.

All combinations of minimum value of
sensitivity and specificity, or of
sensitivity and PPV, or of
sensitivity and NPV, or of
sensitivity and AUC, or of
sensitivity and correct classification rate, or of
specificity and PPV, or of
specificity and NPV, or of
specificity and AUC, or of
specificity and correct classification rate, or of
PPV and NPV, or of
PPV and AUC, or of
PPV and correct classification rate, or of
NPV and AUC, or of
NPV and correct classification rate, or of
AUC and correct classification rate, or of
sensitivity, specificity and PPV, or of
sensitivity, specificity and NPV, or of
sensitivity, specificity and AUC, or of
sensitivity, specificity and correct classification rate, or of
sensitivity, PPV and NPV, or of
sensitivity, PPV and AUC, or of
sensitivity, PPV and correct classification rate, or of
sensitivity, NPV and AUC, or of
sensitivity, NPV and correct classification rate, or of
sensitivity, AUC and correct classification rate, or of
sensitivity, specificity, PPV and NPV, or of
sensitivity, specificity, PPV and AUC, or of
sensitivity, specificity, PPV and correct classification rate, or of
sensitivity, specificity, NPV and AUC, or of
sensitivity, specificity, NPV and correct classification rate, or of
sensitivity, PPV, NPV and correct classification rate, or of
specificity, PPV, NPV and AUC, or of
specificity, PPV, NPV and correct classification rate, or of
sensitivity, specificity, PPV, NPV and AUC, or of
sensitivity, specificity, PPV, NPV and correct classification rate, or of specificity, PPV, NPV, AUC and correct classification rate, or of sensitivity, specificity, PPV, NPV, AUC and correct classification rate, are explicitly included in the description of the application.

For example, said comparison can be done (for example by mROC, logistic regression or CART tree) with at least one of the two performances 1/ and 2/ below:

1/ a specificity of at least 59% and/or a positive predictive value of at least 54%, and/or 2/ a correct classification rate of at least 66% and/or an area under the ROC curve of at least 0.704.

More particularly, said comparison can be done (for example by mROC, logistic regression or CART tree) with at least one of the two performances 1/ and 2/ below:

1/ a specificity of at least 85% and/or a positive predictive value of at least 85%, and/or 2/ a correct classification rate of at least 80% and/or an area under the ROC curve of at least 0.800.

A discriminating rule of the application (whether mROC, CART, LR or other, cf. below), more particularly an mROC function responding to the formula of the function $Z_{10}$, $Z_{11}$, $Z_{12}$ or $Z_{13}$ (cf. below), has a rate of unclassified patients of 0%.

In addition, a discriminating rule of the application (whether mROC, CART, LR or other), more particularly an mROC function responding to the formula of the function $Z_{10}$, $Z_{11}$, $Z_{12}$ or $Z_{13}$, has at least one of its performances of AUC, correct classification rate, sensitivity, NPV, specificity and PPV that is superior:

to that obtained under the same conditions but without the marker HA, to that obtained under the same conditions but without the marker CXCL10.

The inventors demonstrate in fact that the combination of the marker CXCL10 with the marker HA leads to a synergistic effect, i.e., performances that go beyond a simple juxtaposition of their respective individual performances (AUC performances and/or correct classification rate and/or sensitivity and/or NPV and/or specificity and/or PPV). Experimental demonstrations are presented in the Examples below, in particular:

in Example 1 (cf. Table 3), in Example 3 (cf. Tables 8 and 10), and in Example 7 (cf. Tables 20 and 21).

In order to realize said step of comparison of the values of quantification of the biological markers of said patient to their values, or to the distribution of their values, in reference cohorts predefined according to the stage (or degree) of hepatic fibrosis for classifying said patient into the one of these reference cohorts to which they most probably belong, different classification means, such as mROC (linear function), logistic regression (affine function) or decision tree (CART tree, for example), can be employed (cf. above).

More particularly, the inventors demonstrate that the synergistic effect observed with the combination of CXCL10 and HA does not depend on the fact that an mROC function is employed for the classification of the patient; cf. the Examples below, especially:

Example 7, more particularly Tables 20, 21 and 23,

Example 8, more particularly Table 24.

Mathematical Function (for Example, mROC, Logistic Regression)

A mathematical function can be employed to perform said step of comparison of the values of quantification of the biological markers of said patient to their values, or to the distribution of their values, in reference cohorts predefined according to the stage (or degree) of hepatic fibrosis for classifying said patient into the one of these reference cohorts to which they most probably belong. The comparison is then effected by combining the values of quantification of each of the selected biological markers in this mathematical function. This mathematical function can assign a score (Z) to said patient, which is then compared to a threshold value (δ or cut-off) predetermined by multivariate classification, for classifying said patient into the one of these reference cohorts to which they most probably belong (more particularly, for classifying said patient into said first reference cohort or into said second reference cohort).

Said mathematical function can be, for example, a linear function, such as an mROC function, or a non-linear function, for example, an affine function, such as a function of logistic regression using a LOGIT affine function.

An mROC function of the application can have the following form: $Z=a(BMQ_1^t)+b(BMQ_2^t)+c(BMQ_3^t)+d(BMQ_4^t)+e(BMQ_5^t)$, in which $BMQ_1$, $BMQ_2$, $BMQ_3$, $BMQ_4$ and $BMQ_5$ are five different biomarkers (for example, CXCL10, HA, BMI, age and viral load), in which a, b, c, d and e are numerical values of the constants of the mROC function, and in which the exponent t indicates that the value to be applied in the linear function is the Box-Cox transformed form (Box and Cox 1964) of the value of quantification measured for the biomarker (BMQ) in order to normalize this measured value according to the following formula:

$$BMQ^t=(BMQ^\lambda-1)/\lambda.$$

In accordance with the application, an mROC function can be formulated as follows:

$$Z=a(CXCL10^t)+b(HA^t)+c(BMI^t)+d(age^t)+e(VL^t)+f(FS^t) \quad \text{[function } Z_{13}\text{]}$$

with:

a and b each being independently a positive real number going from +0.1 to +6.0;

c, d, e and f each being independently a real number going from −10.0 to +10.0; $\lambda_{CXCL10}$, $\lambda_{HA}$, $\lambda_{BMI}$, $\lambda_{age}$, $\lambda_{VL}$ and $\lambda_{FS}$ each being independently a real number going from −6.0 to 1.2, but excluding zero;

cf. Example 8.

In the function $Z_{13}$ above, like in all the mROC functions mentioned here, the exponent t indicates, according to the usage in the field, that the value to be applied in the linear function is the Box-Cox transformed form (Box and Cox 1964) of the value of quantification measured for the biomarker (BMQ) in order to normalize this measured value according to the following formula: $BMQ^t=(BMQ^\lambda-1)/\lambda$.

The mROC functions of the application, like the function $Z_{13}$ above as well as the functions $Z_{12}$ to $Z_1$ described below, exhibit the performances described above (performances of AUC and/or correct classification rate and/or sensitivity and/or NPV and/or specificity and/or PPV).

The inventors further demonstrate that the performances of the combination of CXCL10 with HA are particularly robust (performances of AUC and/or correct classification rate and/or sensitivity and/or NPV and/or specificity and/or PPV), because the parameters of the mROC function are selected in the indicated ranges of values: cf. Example 9 below.

An example of function $Z_{13}$ is as follows:

$$Z=a(CXCL10^t)+b(HA^t)+c(BMI^t)+d(age^t)+e(VL^t)+f(FS^t) \quad \text{[function } Z_{12}\text{]}$$

with:

a and b each being independently a positive real number going from +0.1 to +6.0, more particularly from +0.3 to +5.5;

c being a real number going from −10.0 to +4.0;

d being a real number going from −0.8 to +0.2;

e being a real number going from −0.003 to +0.002;

f being a real number going from +0.0 to +10.0;

$\lambda_{CXCL10}$, $\lambda_{HA}$, $\lambda_{BMI}$, $\lambda_{age}$, $\lambda_{VL}$ and $\lambda_{FS}$ each being independently a real number going from −6.0 to 1.2, but excluding zero;

cf. Example 8 below.

The threshold value of each of the mROC functions of the application, more particularly $Z_{13}$ and $Z_{12}$, may for example be from −7 to 25, more particularly from 3 to 25, more particularly from 10 to 25.

An mROC function of the application, more particularly $Z_{13}$ and $Z_{12}$, may for example have a correct classification rate of at least 66% and/or a value of area under the ROC curve (AUC) of at least 0.704, more particularly a correct classification rate of at least 72% and/or a value of area under the ROC curve (AUC) of at least 0.729, more particularly a correct classification rate of at least 80% and a value of AUC of at least 0.865, more particularly a correct classification rate of at least 80% and/or a value of area under the ROC curve (AUC) of at least 0.898.

An mROC function of the application, more particularly $Z_{13}$ and $Z_{12}$, may for example have a sensitivity of at least 70% and/or an NPV of at least 70%, more particularly a sensitivity of at least 75% and/or an NPV of at least 75%, more particularly a sensitivity of at least 76% and/or an NPV of at least 75%.

An mROC function of the application, more particularly $Z_{13}$ and $Z_{12}$, may for example have a specificity of at least 59% and/or a PPV of at least 54%, more particularly a specificity of at least 70% and/or a PPV of at least 61%, more particularly a specificity of at least 85% and/or a PPV of at least 85%, more particularly a specificity of at least 86% and/or a PPV of at least 86%.

An example of function $Z_{13}$, which is also an example of function $Z_{12}$, is the following:

$$Z=a(CXCL10^r)+b(HA^r) \quad \text{[function } Z_{10}\text{]}$$

with:

$0.812 \leq a \leq 5.089$
$2.033 \leq b \leq 4.462$
$-0.262 \leq \lambda_{CXCL10} \leq 0.030$
$-0.382 \leq \lambda_{HA} \leq -0.219$;

a, b, $\lambda_{CXCL10}$ and $\lambda_{HA}$ being different from zero.

The threshold value of $Z_{10}$ may be, for example, from −7 to 25, more particularly from 3 to 25, more particularly from 10 to 25, more particularly from 11.68 to 23.71.

Illustrations of functions $Z_{10}$ are shown in Examples 3, 5 and 8 below (functions $Z_{10}$ and $Z_4$).

A function $Z_{10}$ may for example have a correct classification rate of at least 66% and/or a value of AUC of at least 0.704, more particularly a correct classification rate of at least 72% and a value of AUC of at least 0.729, more particularly a correct classification rate of at least 80% and a value of AUC of at least 0.865, more particularly a correct classification rate of at least 80% and a value of AUC of at least 0.898, more particularly a correct classification rate of at least 83% and a value of AUC of at least 0.868 (cf. Examples 3, 5 and 8 below).

A function $Z_{10}$ may for example have a sensitivity of at least 70% and/or an NPV of at least 70%, particularly a sensitivity of at least 75% and/or an NPV of at least 75%, more particularly a sensitivity of at least 76% and/or an NPV of at least 75%, more particularly a sensitivity of at least 78% and/or an NPV of at least 77% (cf. Examples 1, 3, 5 and 6 below).

A function $Z_{10}$ may for example have a specificity of at least 59% and/or a PPV of at least 54%, more particularly a specificity of at least 70% and/or a PPV of at least 61%, more particularly a specificity of at least 85% and/or a PPV of at least 85%, more particularly a specificity of at least 86% and/or a PPV of at least 86%, more particularly a specificity of at least 90% and/or a PPV of at least 90% (cf. Examples 1, 3, 5 and 6 below).

An example of function $Z_{10}$ is the function:

$$Z=(1.999) \times CXCL10^r+(2.852) \times HA^r \quad \text{[function } Z_4\text{]}$$

with $\lambda_{CXCL10}=-0.116$ and $\lambda_{HA}=-0.288$.

The threshold value of $Z_4$ may be, for example, from −7 to 25, more particularly from 3 to 25, more particularly from 10 to 25, more particularly 15.170.

A function $Z_4$ may for example have a correct classification rate of at least 66% and/or a value of AUC of at least 0.704, more particularly a correct classification rate of at least 72% and a value of AUC of at least 0.729, more particularly a correct classification rate of at least 80% and a value of AUC of at least 0.865, more particularly a correct classification rate of at least 80% and a value of AUC of at least 0.882, more particularly a correct classification rate of at least 83% and a value of AUC of at least 0.898 (cf. Examples 3, 5 and 8 below).

A function $Z_4$ may for example have a sensitivity of at least 70% and/or an NPV of at least 70%, particularly a sensitivity of at least 75% and/or an NPV of at least 75%, more particularly a sensitivity of at least 76% and/or an NPV of at least 75%, more particularly a sensitivity of at least 78% and/or an NPV of at least 77% (cf. Examples 3 and 5 below).

A function $Z_4$ may for example have a specificity of at least 59% and/or a PPV of at least 54%, more particularly a specificity of at least 70% and/or a PPV of at least 61%, more particularly a specificity of at least 85% and/or a PPV of at least 85%, more particularly a specificity of at least 86% and/or a PPV of at least 86%, more particularly a specificity of at least 90% and/or a PPV of at least 90% (cf. Examples 3 and 5 below).

Another example of function $Z_{13}$ is the function:

$$Z=0.386 \times CXCL10^r+0.3064 \times HA^r \quad \text{[function } Z_1\text{]}$$

with $\lambda_{CXCL10}=-0.013$ and $\lambda_{HA}=0.099$.

The threshold value of $Z_1$ may be, for example, from −7 to 25, more particularly from 3 to 25, more particularly from 3 to 5, more particularly 3.382.

The function $Z_1$ may for example have a correct classification rate of at least 66% and/or an AUC of at least 0.704 (cf. Example 1 below).

The function $Z_1$ may for example have a sensitivity of at least 78% and/or an NPV of at least 81% (cf. Example 1 below).

The function $Z_1$ may for example have a specificity of at least 59% and/or a PPV of at least 54% (cf. Example 1 below).

Another example of function $Z_{13}$ is the function:

$$Z=(1.849) \times CXCL10^r+(2.368) \times HA^r \quad \text{[function } Z_7\text{]}$$

with $\lambda_{CXCL10}=-0.116$ and $\lambda_{HA}=-0.27$.

The threshold value of $Z_7$ may be, for example, from −7 to 25, more particularly from 3 to 25, more particularly from 10 to 25, more particularly 13.5.

A function $Z_7$ may for example have a correct classification rate of at least 66% and/or a value of AUC of at least 0.704, more particularly a correct classification rate of at least 72% and a value of AUC of at least 0.729, more particularly a correct classification rate of at least 80% and a value of AUC of at least 0.865, more particularly a correct classification rate of at least 82% and a value of AUC of at least 0.865 (cf. Example 6 below).

A function $Z_7$ may for example have a sensitivity of at least 70% and/or an NPV of at least 70%, particularly a sensitivity of at least 75% and/or an NPV of at least 75%, more particularly a sensitivity of at least 76% and/or an NPV of at least 75%, more particularly a sensitivity of at least 78% and/or an NPV of at least 77%.

A function $Z_7$ may for example have a specificity of at least 59% and/or a PPV of at least 54%, more particularly a specificity of at least 70% and/or a PPV of at least 61%, more particularly a specificity of at least 85% and/or a PPV of at least 85%, more particularly a specificity of at least 86% and/or a PPV of at least 86%, more particularly a specificity of at least 90% and/or a PPV of at least 90%.

Another example of function $Z_{13}$, which is also an example of function $Z_{12}$, is as follows:

$$Z=a(CXCL10^r)+b(HA^r)+c(BMI^r)+d(age^r)+e(VL^r) \quad \text{[function } Z_{11}\text{]}$$

with:
$0.748 \leq a \leq 5.357$
$2.075 \leq b \leq 4.690$
$-0.848 \leq c \leq 3.697$
$-0.746 \leq d \leq 0.147$
$-0.003 \leq e \leq 0.002$
$-0.262 \leq \lambda_{CXCL10} \leq 0.047$
$-0.882 \leq \lambda_{HA} \leq -0.219$
$-5.545 \leq \lambda_{BMI} \leq 0.485$
$-0.116 \leq \lambda_{age} \leq 0.828$
$0.236 \leq \lambda_{VL} \leq 0.305$
a, b, c, d, e, $\lambda_{CXCL10}$, $\lambda_{HA}$, $\lambda_{BMI}$, $\lambda_{VL}$ being different from zero.

The threshold value of $Z_{11}$ may be, for example, from −7 to 25, more particularly from −7 to 17.

Illustrations of functions $Z_{11}$ are shown in Examples 1, 3, 6, 7 and 8 below (functions $Z_3$, $Z_5$ and $Z_8$).

A function $Z_{11}$ may for example have a correct classification rate of at least 66% and/or a value of AUC of at least 0.704, more particularly a correct classification rate of at least 72% and a value of AUC of at least 0.729, more particularly a correct classification rate of at least 80% and a value of AUC of at least 0.865, more particularly a correct classification rate of at least 80% and a value of AUC of at least 0.882, more particularly a correct classification rate of at least 83% and a value of AUC of at least 0.899 (cf. Examples 1, 3, 6, 7 and 8 below).

A function $Z_{11}$ may for example have a sensitivity of at least 70% and/or an NPV of at least 70%, particularly a sensitivity of at least 75% and/or an NPV of at least 75%, more particularly a sensitivity of at least 76% and/or an NPV of at least 75%, more particularly a sensitivity of at least 80% and/or an NPV of at least 78% (cf. Examples 1, 3, 6 and 7 below).

A function $Z_{11}$ may for example have a specificity of at least 59% and/or a PPV of at least 54%, more particularly a specificity of at least 70% and/or a PPV of at least 61%, more particularly a specificity of at least 85% and/or a PPV of at least 85%, more particularly a specificity of at least 86% and/or a PPV of at least 86%, more particularly a specificity of at least 87% and/or a PPV of at least 88% (cf. Examples 1, 3, 6 and 7 below).

An example of function $Z_{11}$ is the function:

$$Z=(0.2914) \times CXCL10^r+(0.2569) \times HA^r+(-9.3855) \times BMI^r+(0.01419) \times age^r+(0.0140) \times VL^r \quad \text{[function } Z_3\text{]}$$

with
$\lambda_{CXCL10}=-0.013$
$\lambda_{HA}=0.099$
$\lambda_{age}=1.086$
$\lambda_{BMI}=-0.923$
$\lambda_{VL}=0.159$.

The threshold value of $Z_3$ may be, for example, from −7 to 25, more particularly from −7 to 17, more particularly −5.730.

The function $Z_3$ may for example have a correct classification rate of at least 66% and/or an AUC of at least 0.704, more particularly a correct classification rate of at least 72% and a value of AUC of at least 0.729, more particularly a correct classification rate of at least 73% and an AUC of at least 0.731, more particularly a correct classification rate of at least 80% and a value of AUC of at least 0.868 (cf. Examples 1 and 8 below).

The function $Z_3$ may for example have a sensitivity of at least 70% and/or an NPV of at least 70%, particularly a sensitivity of at least 75% and/or an NPV of at least 75%, more particularly a sensitivity of at least 76% and/or an NPV of at least 75%, more particularly a sensitivity of at least 76% and/or an NPV of at least 83% (cf. Example 1 below).

The function $Z_3$ may for example have a specificity of at least 59% and/or a PPV of at least 54%, more particularly a specificity of at least 70% and/or a PPV of at least 61%, more particularly a specificity of at least 71% and/or a PPV of at least 62% (cf. Example 1 below).

An example of function $Z_{11}$ is the function:

$$Z=(1.999) \times CXCL10^r+(2.958) \times HA^r+(0.616) \times BMI^r+(-0.053) \times age^r+(-0.00024) \times VL^r \quad \text{[function } Z_5\text{]}$$

with
$\lambda_{CXCL10}=-0.116$
$\lambda_{HA}=-0.288$
$\lambda_{age}=0.433$
$\lambda_{BMI}=-0.039$
$\lambda_{VL}=0.279$.

The threshold value of $Z_5$ may be, for example, from −7 to 25, more particularly from −7 to 17, more particularly 16.543.

A function $Z_5$ may for example have a correct classification rate of at least 66% and/or a value of AUC of at least 0.704, more particularly a correct classification rate of at least 72% and a value of AUC of at least 0.729, more particularly a correct classification rate of at least 80% and a value of AUC of at least 0.865, more particularly a correct classification rate of at least 80% and a value of AUC of at least 0.868, more particularly a correct classification rate of at least 80% and a value of AUC of at least 0.882, more particularly a correct classification rate of at least 83% and a value of AUC of at least 0.899 (cf. Examples 1, 3, 7 and 8 below).

A function $Z_5$ may for example have a sensitivity of at least 70% and/or an NPV of at least 70%, particularly a sensitivity of at least 75% and/or an NPV of at least 75%, more particularly a sensitivity of at least 76% and/or an NPV of at least 75%, more particularly a sensitivity of at least 80% and/or an NPV of at least 78% (cf. Examples 1, 3 and 7 below).

A function $Z_5$ may for example have a specificity of at least 59% and/or a PPV of at least 54%, more particularly a specificity of at least 70% and/or a PPV of at least 61%, more particularly a specificity of at least 85% and/or a PPV of at least 85%, more particularly a specificity of at least 86% and/or a PPV of at least 86%, more particularly a specificity of at least 87% and/or a PPV of at least 88% (cf. Examples 1, 3 and 7 below).

An example of function $Z_{11}$ is the function:

$$Z=(1.853) \times CXCL10^r+(2.511) \times HA^r+(0.4246) \times BMI^r+(-0.0343) \times age^r+(-0.00027) \times VL^r \quad \text{[function } Z_8\text{]}$$

with
$\lambda_{CXCL10}=-0.116$
$\lambda_{HA}=-0.27$
$\lambda_{age}=0.536$
$\lambda_{BMI}=-0.0056$
$\lambda_{VL}=0.288$.

The threshold value of $Z_8$ may be, for example, from −7 to 25, more particularly from −7 to 17, more particularly 14.7.

A function $Z_8$ may for example have a correct classification rate of at least 66% and/or a value of AUC of at least 0.704, more particularly a correct classification rate of at least 72% and a value of AUC of at least 0.729, more particularly a correct classification rate of at least 80% and a value of AUC of at least 0.865, more particularly a correct classification rate of at least 80% and a value of AUC of at least 0.868, more particularly a correct classification rate of at least 82% and a value of AUC of at least 0.868 (cf. Examples 6 and 8 below).

A function $Z_8$ may for example have a sensitivity of at least 70% and/or an NPV of at least 70%, particularly a sensitivity of at least 75% and/or an NPV of at least 75%, more particularly a sensitivity of at least 76% and/or an NPV of at least 75%, more particularly a sensitivity of at least 80% and/or an NPV of at least 78%.

A function $Z_8$ may for example have a specificity of at least 59% and/or a PPV of at least 54%, more particularly a specificity of at least 70% and/or a PPV of at least 61%, more particularly a specificity of at least 85% and/or a PPV of at least 85%, more particularly a specificity of at least 86% and/or a PPV of at least 86%, more particularly a specificity of at least 87% and/or a PPV of at least 88%.

Another example of function $Z_{13}$, which is also an example of function $Z_{12}$, is the following:

$$Z=(0.3313) \times CXCL10'+(0.25154) \times HA'+(-9.8818) \times BMI'+(0.0143) \times age'$$ [function $Z_2$]

with
$\lambda_{CXCL10}=-0.013$
$\lambda_{HA}=0.099$
$\lambda_{age}=1.086$
$\lambda_{BMI}=-0.923$.

The threshold value of $Z_2$ may be, for example, from −7 to 25, more particularly from −7 to 17, more particularly 14.7.

A function $Z_2$ may for example have a correct classification rate of at least 66% and/or a value of AUC of at least 0.704, more particularly a correct classification rate of at least 72% and a value of AUC of at least 0.729 (cf. Example 1 below).

A function $Z_2$ may for example have a sensitivity of at least 70% and/or an NPV of at least 70%, particularly a sensitivity of at least 75% and/or an NPV of at least 75%, more particularly a sensitivity of at least 76% and/or an NPV of at least 75%, more particularly a sensitivity of at least 76% and/or an NPV of at least 82% (cf. Example 1 below).

A function $Z_2$ may for example have a specificity of at least 59% and/or a PPV of at least 54%, more particularly a specificity of at least 70% and/or a PPV of at least 61% (cf. Example 1 below).

Another example of function $Z_{13}$, which is also an example of function $Z_{12}$, is the following:

$$Z=(1.686) \times CXCL10'+(2.216) \times HA'+(6.947) \times FS$$ [function $Z_6$]

FS being the value of quantification of the stiffness of the liver, for example, in kDa, with
$\lambda_{CXCL10}=-0.016$
$\lambda_{HA}=0.2888$
$\lambda_{FS}=-0.888$.

The threshold value of $Z_6$ may be, for example, from −7 to 25, more particularly from −7 to 17, more particularly 14.7.

A function $Z_6$ may for example have a correct classification rate of at least 66% and/or a value of AUC of at least 0.704, more particularly a correct classification rate of at least 72% and a value of AUC of at least 0.729, more particularly a correct classification rate of at least 80% and a value of AUC of at least 0.865, more particularly a correct classification rate of at least 80% and a value of AUC of at least 0.868, more particularly a correct classification rate of at least 86% and a value of AUC of at least 0.931 (cf. Example 5 below).

A function $Z_6$ may for example have a sensitivity of at least 70% and/or an NPV of at least 70%, particularly a sensitivity of at least 75% and/or an NPV of at least 75%, more particularly a sensitivity of at least 76% and/or an NPV of at least 75%, more particularly a sensitivity of at least 83% and/or an NPV of at least 81% (cf. Example 5 below).

A function $Z_6$ may for example have a specificity of at least 59% and/or a PPV of at least 54%, more particularly a specificity of at least 70% and/or a PPV of at least 61%, more particularly a specificity of at least 85% and/or a PPV of at least 85%, more particularly a specificity of at least 86% and/or a PPV of at least 86%, more particularly a specificity of at least 89% and/or a PPV of at least 90% (cf. Example 5 below).

Another example of function $Z_{13}$, which is also an example of function $Z_{12}$, is the following:

$$Z_7=(1.585) \times CXCL10'+(2.181) \times HA'+(2.910) \times FS$$ [function $Z_9$]

FS being the value of quantification of the stiffness of the liver, for example, in kDa, with
$\lambda_{CXCL10}=-0.016$
$\lambda_{HA}=-0.27$
$\lambda_{FS}=-0.27$.

The threshold value of $Z_9$ may be, for example, from −7 to 25, more particularly from −7 to 17, more particularly 14.7.

A function $Z_9$ may for example have a correct classification rate of at least 66% and/or a value of AUC of at least 0.704, more particularly a correct classification rate of at least 72% and a value of AUC of at least 0.729, more particularly a correct classification rate of at least 80% and a value of AUC of at least 0.865, more particularly a correct classification rate of at least 85% and a value of AUC of at least 0.868 (cf. Example 6 below).

A function $Z_9$ may for example have a sensitivity of at least 70% and/or an NPV of at least 70%, particularly a sensitivity of at least 75% and/or an NPV of at least 75%, more particularly a sensitivity of at least 76% and/or an NPV of at least 75% (cf. Example 6 below).

A function $Z_9$ may for example have a specificity of at least 59% and/or a PPV of at least 54%, more particularly a specificity of at least 70% and/or a PPV of at least 61%, more particularly a specificity of at least 85% and/or a PPV of at least 85%, more particularly a specificity of at least 86% and/or a PPV of at least 86% (cf. Example 6 below).

A function of logistic regression may have the following form:

$$LOGIT=Intercept+k(BMQ_1)+l(BMQ_2),$$

in which $BMQ_1$ and $BMQ_2$ are two different biomarkers (for example, CXCL10 and HA), and in which Intercept, k and l are numerical values of the constants of the function of logistic regression.

For example:

$$LOGIT=Intercept+k(CXCL10)+l(AH),$$ [function $LOGIT_1$]

with
$-5 \leq Intercept \leq -1$
$0.001 \leq k \leq 0.010$
$0.010 \leq l \leq 0.050$.

More particularly, a function of logistic regression may be:

LOGIT=Intercept+k(CXCL10)+l(HA),   [function LOGIT$_2$]

with
−4.481≤Intercept≤−2.398
0.003≤k≤0.008
0.013≤l≤0.045;
(cf. Example 8, Table 24).

Illustrations of functions of logistic regression LOGIT$_1$ and LOGIT$_2$ are shown in Example 7 below, namely:

LOGIT$_3$=Intercept+k(CXCL10)+l(HA),   [function LOGIT$_3$]

with
−3.57≤Intercept≤−2.67
0.003≤k≤0.007; and
0.02≤l≤0.04 (cf. Example 7, Table 19);

LOGIT=Intercept+k(CXCL10)+l(HA),   [function LOGIT$_4$]

with
Intercept=−3.164
k=0.005; and
l=0.024 (cf. Example 7, Table 22).

The threshold value of each of the LOGIT functions of the application, more particularly of LOGIT$_1$, LOGIT$_2$, LOGIT$_3$, LOGIT$_4$, may be, for example, 0.5.

A function of logistic regression of the application (using a LOGIT affine function), more particularly LOGIT$_1$, LOGIT$_2$, LOGIT$_3$ and LOGIT$_4$, may for example have a correct classification rate of at least 66% and/or a value of area under the ROC curve (AUC) of at least 0.704, more particularly a correct classification rate of at least 72% and/or a value of area under the ROC curve (AUC) of at least 0.729, more particularly a correct classification rate of at least 80% and a value of AUC of at least 0.865, more particularly a correct classification rate of at least 80% and/or a value of area under the ROC curve (AUC) of at least 0.882.

A function of logistic regression of the application, more particularly LOGIT$_1$, LOGIT$_2$, LOGIT$_3$ and LOGIT$_4$, may for example further have a sensitivity of at least 70% and/or an NPV of at least 70%, particularly a sensitivity of at least 75% and/or an NPV of at least 75%, more particularly a sensitivity of at least 76% and/or an NPV of at least 75%.

A function of logistic regression of the application, more particularly LOGIT$_1$, LOGIT$_2$, LOGIT$_3$ and LOGIT$_4$, may for example have a specificity of at least 59% and/or a PPV of at least 54%, more particularly a specificity of at least 70% and/or a PPV of at least 61%, more particularly a specificity of at least 85% and/or a PPV of at least 85%, more particularly a specificity of at least 86% and/or a PPV of at least 86%.

Machine Learning (for Example, CART)

Alternatively or complementarily, machine learning can be employed to compare the values of quantification of the biomarkers to their values, or to the distribution of their values, in the predefined reference cohorts according to the stage of hepatic fibrosis, in order to classify said patient into the one of these reference cohorts to which they most probably belong. Said machine learning can be learning by a decision tree, more particularly by a CART decision tree.

For example, the values of quantification obtained for said patient are each compared to a threshold value belonging to, or characteristic of, the marker of that value, by following a decision tree, more particularly a CART decision tree. This decision tree (more particularly this CART decision tree), more particularly said threshold values of this tree, can be determined [in advance] by machine learning, more particularly by establishing a decision tree (more particularly by establishing a CART tree), from the values of quantification, or from the distribution of the values of quantification, of said reference cohorts, more particularly of said first and second reference cohorts. A decision tree, more particularly a CART decision tree, can thus be defined by a series of threshold values ordered according to a decision tree.

For example, a decision tree using the markers HA and CXCL10 can be defined by three threshold values:
a first threshold value (for example, h) assigned to the value of quantification of one of the two biomarkers (for example, the value of quantification of HA) and creating a branching point with two branches according to whether the value of quantification is lower or higher than the threshold value, then
two more threshold values (for example, i and j) each assigned to the value of quantification of the other one of the two biomarkers (for example, the value of quantification of CXCL10), one of these two more threshold values being assigned to one of the two branches, and the other one of these two more threshold values being assigned to the other one of the two branches.

Such a CART tree is shown in FIG. 12.

In accordance with FIG. 12, said machine learning can be a CART decision tree that includes a threshold of decision h for the marker HA and thresholds of decision i and j for the marker CXCL10, said thresholds h, i and j being as follows:
if the value of quantification of HA for said patient is lower than h, the threshold of the marker CXCL10 is j, and:
said patient is classified into said first cohort (Metavir fibrosis score <F2) if the value of quantification of CXCL10 is lower than j;
said patient is classified into said second cohort (Metavir fibrosis score ≥F2) if the value of quantification of CXCL10 is higher than or equal to j; and
if the value of quantification of HA for said patient is higher than or equal to h, the threshold of the marker CXCL10 is i, and:
said patient is classified into said first cohort (Metavir fibrosis score <F2) if the value of quantification of CXCL10 is lower than i;
said patient is classified into said second cohort (Metavir fibrosis score ≥F2) if the value of quantification of CXCL10 is higher than or equal to i.

For example, the CART tree is that of FIG. 12 with:
40≤h≤80
150≤i≤300
400≤j≤620
[CART$_1$ tree].

For example, the CART tree is that of FIG. 12 with:
41.96≤h≤77.43
159.09≤i≤266.7
410.75≤j≤613.49
[CART$_2$ tree]; cf. Example 8.

For example, the CART tree is that of FIG. 12 with:
42.18≤h≤77.4
209.3≤i≤266.7
454.7≤j≤553.1
[CART$_3$ tree]; cf. Examples 7 and 8.

For example, the CART tree is that of FIG. 12 with:
h=47.29
i=209.3
j=503.4
[CART$_4$ tree]; cf. Examples 7 and 8.

A CART tree of the application, more particularly CART$_1$, CART$_2$, CART$_3$ and CART$_4$, may for example have a correct classification rate of at least 66%, more particularly at least 72%, more particularly at least 80%, more particularly at least 83%, more particularly at least 84%, more particularly at least 85%.

A CART tree of the application, more particularly $CART_1$, $CART_2$, $CART_3$ and $CART_4$, may for example have a sensitivity of at least 70% and/or an NPV of at least 70%, particularly a sensitivity of at least 75% and/or an NPV of at least 75%, more particularly a sensitivity of at least 76% and/or an NPV of at least 75%, more particularly a sensitivity of at least 77% and/or an NPV of at least 77%, more particularly a sensitivity of at least 78% and/or an NPV of at least 78%, more particularly a sensitivity of at least 82% and/or an NPV of at least 80%.

A CART tree of the application, more particularly $CART_1$, $CART_2$, $CART_3$ and $CART_4$, may for example have a specificity of at least 59% and/or a PPV of at least 54%, more particularly a specificity of at least 70% and/or a PPV of at least 61%, more particularly a specificity of at least 85% and/or a PPV of at least 85%, more particularly a specificity of at least 86% and/or a PPV of at least 86%, more particularly a specificity of at least 89% and/or a PPV of at least 90%, more particularly a specificity of at least 91% and/or a PPV of at least 91%.

Combination of Machine Learning and Mathematical Function

Alternatively or complementarily, said comparison can be done by combining machine learning and mathematical function, for example, by combining a decision tree and a linear or non-linear function.

For example, this comparison can be done:
 by a decision tree, more particularly by a CART tree, for one or at least one marker selected from the viral load, age, BMI and the stiffness of the liver, more particularly for (at least) the marker stiffness of the liver, then
 by a linear or affine function, more particularly by mROC or logistic regression, for markers selected as described above, more particularly for at least the markers CXCL10 and HA.

Illustrations are shown in Example 6 below and in FIGS. 9, 10, 11: comparison to a threshold value for one of the values (in this case the value of stiffness of the liver), followed by a comparison by means of a linear function for the markers CXCL10 and HA (FIG. 9), or for the markers CXCL10, HA, age, BMI and VL (FIG. 10), or for the markers CXCL10, HA and FS (FIG. 11).

Thus, according to one embodiment, the process starts with a step of measuring the stiffness of the liver of said patient, for example, using FIBROSCAN™. This step allows, for example, to determine whether or not the liver of said patient is affected by cirrhosis (Metavir stage F4). If it is not affected by cirrhosis, i.e., if the stage of the hepatic fibrosis of said patient is lower than a Metavir score F4, a sample of biological fluid can be analyzed to quantify the biological markers selected as described above, more particularly for at least CXCL10 and HA, to determine further the stage of hepatic fibrosis (Metavir score F0 or F1, or else Metavir score F2 or F3). If the liver of said subject is affected by cirrhosis (detected by measuring the stiffness of the liver), the performance of an analysis of a sample of biological fluid seems superfluous and is thus not necessary.

Other Objects of the Application

According to a complementary aspect, the application relates to products, reagents or ligands for the detection and/or quantification of the selected biomarkers, more particularly to reagents or ligands that bind specifically to circulating molecules selected as biomarkers as described above, as well as to articles of manufacture, compositions, pharmaceutical compositions, kits, tubes, solid supports comprising such reagents or ligands, as well as to computing systems (especially computer program and computing device product), which are especially suitable for the application of the methods or products of the application.

In particular, the application relates to a ligand that binds specifically to a biomarker that is a circulating molecule as described above, for example, a ligand that binds specifically to HA, or a ligand that binds specifically to CXCL10 (more particularly to the human protein CXCL10). More particularly, this ligand binds specifically to the circulating form of this molecule, or if there are several thereof, to at least one, to several, or to all circulating forms of this molecule.

Preferably, this ligand allows not only to specifically detect the selected biomarker, but also to quantify it.

In particular, this ligand may be a protein, polypeptide, peptide, for example an antibody (monoclonal or polyclonal), an antibody fragment, a recombinant protein, an aptamer, a polysaccharide, a lipid, or a combination of such products, more particularly a protein, an antibody (monoclonal or polyclonal), an antibody fragment or a recombinant protein.

For example, antibodies can be produced by immunization of a non-human mammal (such as a rabbit) by a protein encoded by said selected gene, or by an antigenic fragment of such a protein, optionally associated or coupled to an immunization adjuvant (such as Freund's adjuvant or KLH=keyhole limpet hemocyanin), for example, by intraperitoneal or subcutaneous injection, and by collecting the antibodies thus obtained in the serum of said mammal.

Monoclonal antibodies can be produced by a lymphocyte hybridization method (hybridomas), such as the method of Köhler and Milstein 1975 (cf. also U.S. Pat. No. 4,376,110), the human B cell hybridoma method (Kosbor et al. 1983; Cole et al. 1983), or the method of immortalization of lymphocytes by means of Epstein-Barr virus=EBV (Cole et al. 1985). Such antibodies can be, for example, IgG, IgM, IgE, IgA, IgD, or any other subclass of these immunoglobins. Antibodies modified by genetic engineering can be produced, such as recombinant, chimeric antibodies or antibodies humanized by implanting one or more CDR=complementary determining regions.

The antibodies employed in the invention can be fragments of antibodies or artificial derivatives of such fragments, as long as such fragments or derivatives show said property of specific binding. Such fragments can be, for example, the fragments Fab, F(ab')2, Fv, Fab/c, scFv (single chain Fragment variable).

Examples of ligands include antibodies that bind specifically to CXCL10, such as:
 mouse monoclonal anti-human CXCL10 antibody commercially available from R&D SYSTEMS, Inc. (614 McKinley Place NE; Minneapolis, Minn. 55413; USA), under the catalogue reference MAB266 (clone 33036, class IgG1);
 goat polyclonal anti-human CXCL10 antibody available from R&D SYSTEMS, Inc. (614 McKinley Place NE; Minneapolis, Minn. 55413; USA), under the catalogue reference AF-266-NA for a form not coupled to biotin);
 mouse monoclonal anti-human CXCL10 antibody available from R&D SYSTEMS, Inc. (614 McKinley Place NE; Minneapolis, Minn. 55413; USA; catalogue reference MAB266).

When using a "sandwich" configuration, each of these antibodies can be employed as a capture ligand and/or as a detection ligand.

Examples of ligands include proteins that bind specifically to HA, such as the recombinant human protein aggrecan G1-IGD-G2 commercially available from the company R&D SYSTEMS, Inc. (614 McKinley Place NE; Minneapolis, Minn. 55413; USA), under the catalogue reference 1220-PG-025, or the protein HABP (HA binding protein; a protein derived from bovine cartilage) commercially available from UNITED STATES BIOLOGICAL (4 Technology Way, Salem, Mass. 01970, USA) under the catalogue reference H7980-30.

When using a "sandwich" configuration, this recombinant protein can be employed as a capture ligand and/or as a detection ligand.

Each of said ligands can further include at least one marker for their detection, more particularly at least one marker for detection that is not naturally present in the structure of the ligand, for example, at least one moiety selected from fluorophores (for example ATTO™ 550, ATTO™ 663; ATTO-TEC GmbH, Siegen, Germany), chromophores, enzymes (for example, horseradish peroxydase, alkaline phosphatase), radioactive elements, isotopes of chemical elements.

The application also relates to a set or association of at least two ligands, namely a first ligand that binds specifically to one of the selected circulating molecules, and a second ligand that binds specifically to another one of the selected circulating molecules, for example, the set or association of a ligand specific for HA and a ligand specific for CXCL10.

Each of said first and second ligands may or may not bear a marker for its detection. Said first and second ligands may each bear a marker for its detection. They may each bear the same marker, or else bear different markers.

Said ligands may be in admixture, or else in distinct forms or in forms physically separated from one another, for example, in a combined preparation for simultaneous use, separately or at different times.

According to one embodiment, the set or association contains no ligand that would bind to a circulating protein not included in the circulating molecules selected as biomarkers as described above. More particularly, according to this embodiment, the set or association contains no ligand that would bind to a circulating protein other than HA or CXCL10. More particularly, according to this embodiment, the set or association contains no ligand that would bind to A2M, GMCSF, IL-12, IL-2, MMP13, ALT, GGT, ICAM1, IL-4, CXCL9, VCAM1, RBP4, TIMP1, VIM, SPP1, AST, ApoA1, IL6ST, p14ARF, MMP9, ANGPT2, CXCL11, MMP2, MMP1, S100A4, TIMP1, CHI3L1, COL1A1, CXCL1, CXCL6, IHH, IRF9 or MMP1.

This set or association may further comprise means for the detection and/or measurement of the viral load in hepatitis virus (for example, HCV and/or HBV and/or HDV).

The application also relates to an article of manufacture, composition, pharmaceutical composition, kit that each comprise at least one ligand or at least one set or association of ligands of the application.

More particularly, the application relates to an article of manufacture, composition, pharmaceutical composition, kit that are each suitable for the multiplex detection of circulating molecules, i.e., molecules contained in acellular form in a (sample of) biological fluid, such as CXCL10 and HA (cf. "Circulating molecules" above).

More particularly, the application relates to an article of manufacture, composition, pharmaceutical composition, kit that each comprise:
- a first ligand (for example, a first protein) that binds specifically to one of the selected circulating molecules, for example, a first ligand (more particularly a first protein, more particularly an antibody) that binds specifically to CXCL10; and
- a second ligand (for example, a second protein) that binds specifically to another one of the selected circulating molecules, for example, a second ligand (more particularly a second protein) that binds specifically to HA.

More particularly, the application relates to an article of manufacture, composition, pharmaceutical composition, kit that each comprise these first and second ligands as a combination product (or in a combined form, or as a combined preparation), especially for simultaneous, separated or temporally distributed use, more particularly for simultaneous use in time.

According to one embodiment, the article of manufacture, composition, pharmaceutical composition or kit contains no ligand that would bind to a circulating protein not included in the circulating molecules selected as biomarkers as described above. More particularly, according to this embodiment, the article of manufacture, composition, pharmaceutical composition or kit contains no ligand that would bind to a circulating protein other than HA or CXCL10. More particularly, according to this embodiment, the article of manufacture, composition, pharmaceutical composition or kit contains no ligand that would bind to A2M, GMCSF, IL-12, IL-2, MMP13, ALT, GGT, ICAM1, IL-4, CXCL9, VCAM1, RBP4, TIMP1, VIM, SPP1, AST, ApoA1, IL6ST, p14 ARF, MMP9, ANGPT2, CXCL11, MMP2, MMP7, S100A4, TIMP1, CHI3L1, COL1A1, CXCL1, CXCL6, IHH, IRF9 or MMP1.

Thus, the application relates to an article of manufacture suitable for the multiplex detection of molecules contained in acellular form in a (sample of) biological fluid, and comprising a solid support to which the ligands of said molecules are attached.

Said article of manufacture may be, for example:
- one or more tubes;
- a kit, especially a kit comprising one or more tubes;
- a solid or semi-solid support, for example, made of plastic, polystyrene, polypropylene, glass, silicon, nitrocellulose, poly(vinylidene fluoride) [PVDF] or polymer, or comprising a magnetic material, such as iron oxide, for example:
    - a plate or microplate with wells, for example, made of microplate with wells suitable for titration and/or high throughput screening (high throughput screening microplates);
    - a chip or microarray (with integrated circuit) made of a conducting or semiconducting material, more particularly a silicon wafer chip (or microarray), more particularly a chip (or microarray) made of silicon;
    - a capillary, more particularly a glass capillary;
    - a magnetic bead having a mean diameter lower than a micrometer;
    - a glass slide;
    - a membrane (for example, a membrane made of nitrocellulose or PVDF).

More particularly, microplates for high throughput screening can be used (cf. Example 10). The wells of these microplates have the capability of adsorbing biomolecules, more particularly proteins. They generally have an excellent thermal and chemical stability as well as excellent optical properties. They are generally made of polystyrene and/or polypropylene. Each microplate contains a plurality of wells, generally 96 wells. These microplates are devised to receive rows of droplets of said first and second ligands whose volume is lower than 100 nL per droplet (generally 50 nL per droplet). A spotter robot can be used to deposit these rows of droplets.

Said first and second ligands can be attached, immobilized or grafted on the article of manufacture, or covalently bonded thereto.

The article of manufacture may be, for example, in the form of an article of manufacture suitable for the multiplex detection of molecules contained in acellular form in a (sample of) biological fluid having a volume lower than or equal to 500 µL (more particularly lower than or equal to 400 µL, more particularly lower than or equal to 100 µL), wherein said solid support comprises a plurality of liquid sample reception zones, said zones being fluidly independent of each other, each being suitable for the reception of a single liquid sample per zone, wherein the maximum volume of liquid sample that each zone can receive does not exceed 500 µL (more particularly lower than or equal to 400 µL, more particularly lower than or equal to 100 µL), and wherein at least one of said liquid sample reception zones comprises both said first ligand and said second ligand (more particularly, said first protein and said second protein). Said liquid sample reception zones can, for example, be wells of a plate or microplate for titration and/or high throughput screening, the reception wells of spots on a silicon chip, cylindrical portions of a glass capillary, a membrane, a glass slide, a tube.

In the article of manufacture, said first ligand and said second ligand (more particularly, said first protein and said second protein) can be attached (or immobilized, or grafted, or covalently bonded) to said solid support in a configuration according to which only one liquid sample with a volume lower than or equal to 500 µL (more particularly lower than or equal to 400 µL, more particularly lower than or equal to 100 µL) can contact both said first protein and said second protein.

In the article of manufacture, said first ligand (more particularly, said first protein) can be attached (or immobilized, or grafted, or covalently bonded) to said solid support in a first attachment site, and said second ligand (more particularly, said second protein) can be attached (or immobilized, or grafted, or covalently bonded) to said solid support in a second attachment site, wherein said first attachment site is in fluid communication with said second attachment site.

Each of these first and second ligands can be used as a capture ligand (for example, in the case of detection in sandwich configuration additionally using detection ligands that bear at least one detection marker; cf. composition below, cf. Example 10).

According to one embodiment, the ligands of circulating molecules that are contained in an article of manufacture comprise no ligand that would bind to A2M, GMCSF, IL-12, IL-2, MMP13, ALT, GGT, ICAM1, IL-4, CXCL9, VCAM1, RBP4, TIMP1, VIM, SPP1, AST, ApoA1, IL6ST, p14ARF, MMP9, ANGPT2, CXCL11, MMP2, MMP1, S100A4, TIMP1, CHI3L1, COL1A1, CXCL1, CXCL6, IHH, IRF9 or MMP1.

According to one embodiment, the ligands of circulating molecules that are contained in an article of manufacture consist of:
 a first ligand (for example, a first protein) that binds specifically to HA;
 a second ligand (for example, a second protein, more particularly an antibody) that binds specifically to CXCL10.

Optionally, an article of manufacture further comprises instructions (for example, a sheet of instructions) for quantifying the molecules to which the ligands specifically bind, for example, for quantifying CXCL10 and HA, more particularly instructions (for example, a sheet of instructions) for quantifying these molecules and determine a stage or score of hepatic fibrosis from the values of quantification obtained.

Said article of manufacture may further comprise one or more of the following elements:
 an instrument for collecting said sample, especially:
  a needle and/or syringe, more particularly a needle and/or syringe for collecting an intracorporeal fluid, such as blood; and/or
  a needle suitable for hepatic cytopuncture, for example, a needle having a diameter of 18 to 22G); and/or
  a needle and/or catheter and/or biopsy gun suitable for PBH;
 a computer program or software product, especially a computer program or software product for statistical analysis, for example, a computer program product of the invention as described below.

The application also relates to a composition suitable for the multiplex detection of molecules, more particularly for the multiplex detection of molecules contained in acellular form in a fluid (such as the molecules CXCL10 and HA), comprising in admixture:
 a first ligand that bears a first detection marker, and
 a second ligand that bears a second detection marker.

Said first detection marker can be the same or different from said second detection marker.

The first ligand and the second ligand are each specific for a different circulating molecule (circulating molecule selected as a biomarker as described above).

More particularly, said first ligand is a ligand (for example, a protein) that binds specifically to HA, and said second ligand is a ligand (for example, a protein, more particularly an antibody) that binds specifically to (human) CXCL10, more particularly a ligand (for example, a protein, more particularly an antibody) that binds specifically to one, at least one, several or all circulating forms of the (human) protein CXCL10.

These first and second ligands may, for example, be used as detection ligands (for example, in the case of detection in sandwich configuration with capture ligands; cf. Article of manufacture above; cf. Example 10).

The application also relates to a kit comprising:
 nucleic acids that bind specifically to one or more hepatitis viruses, and further comprising
 ligands that bind to molecules contained in acellular form in a biological fluid, said ligands being contained in the kit in a combined preparation for separate, distributed or simultaneous use in time, more particularly for simultaneous use in time, more particularly for use in admixture.

Said ligands that bind to molecules contained in acellular form in a biological fluid consist of:
 a first ligand that bears a first detection marker, and
 a second ligand that bears a second detection marker.

Said first detection marker can be the same or different from said second detection marker.

The first ligand and the second ligand are each specific for a different circulating molecule (circulating molecule selected as a biomarker as described above).

More particularly, said first ligand is a ligand (for example, a protein) that binds specifically to HA, and said second ligand is a ligand (for example, a protein, more particularly an antibody) that binds specifically to (human) CXCL10, more particularly a ligand (for example, a protein, more particularly an antibody) that binds specifically to one, at least one, several or all circulating forms of the (human) protein CXCL10.

These first and second ligands may, for example, be used as detection ligands (for example, in the case of detection in sandwich configuration with capture ligands; cf. Article of manufacture above; cf. Example 10).

The kit may further comprise an article of manufacture as described above.

The application also relates to said ligand, set or association of ligands, article of manufacture, composition, pharmaceutical composition, kit for use in a process for detecting or diagnosing a liver disease involving tissue lesions of the liver, more particularly hepatic fibrosis, more particularly for determining the score of hepatic fibrosis of a patient, more particularly hepatic fibrosis, more particularly for determining whether or not the score of hepatic fibrosis of a patient has passed beyond that of a mild fibrosis, more particularly for determining whether the hepatic fibrosis of a patient has a Metavir fibrosis score of at most F1, or else of at least F2.

The application also relates to said ligand, set or association of ligands, article of manufacture, composition, pharmaceutical composition, kit for use in a process for the treatment of a liver disease involving tissue lesions of the liver, more particularly hepatic fibrosis.

Such use may comprise, in particular:
the use of said ligand(s) in a process of the invention for determining whether or not the score of hepatic fibrosis of a patient has passed beyond that of a mild fibrosis, more particularly for determining whether the hepatic fibrosis of a patient has a Metavir fibrosis score of at most F1, or else of at least F2; and
administering to said patient a treatment aiming at blocking the progression of hepatic fibrosis (such as a treatment comprising standard or pegylated interferon in a monotherapy, or in a pluritherapy involving ribavirin), if the patient has a score of hepatic fibrosis that has passed beyond that of a mild fibrosis (Metavir fibrosis score of at least F2).

This process may further comprise that the treatment is not administered if, or as long as, this score does not pass beyond that of a mild fibrosis.

This treatment may be, for example:
pegylated interferon alpha-2b (such as PEG-INTRON®, Schering Plough Corporation, Kenilworth, N.J.) at a dose of approximately 1.5 g/kg/week, and ribavirin (REBETOL®; Schering Plough Corporation, Kenilworth, N.J.) at a dose of 800 to 1200 mg/kg/day (if the liver disease implies an HCV of genotype 2 or 3, a dose of approximately 800 mg/kg/day is generally
pegylated interferon alpha-2a (such as PEGASYS®; Roche Corp., F. Hoffmann-La Roche Ltd.; Basel, Switzerland) at a concentration of 180 g/kg/week and ribavirin (COPEGUS®, Roche Corp.; F. Hoffmann-La Roche Ltd.; Basel, Switzerland) at a dose of 1000 to 1200 mg/kg/day.

The duration of the treatment may be, for example, at least 24 weeks, for example, 24 weeks for a liver disease of HCV of genotype 2 or 3, or 48 week for a liver disease of HCV of genotype 1, 4 or 5, or for a patient who has not responded to the treatment by the end of 24 weeks.

The application also relates to a medicament or medicamental association for the treatment of a liver disease involving damage of the liver tissue, more particularly hepatic fibrosis (such as standard interferon or pegylated interferon in a monotherapy, or in a pluritherapy involving one or more other active ingredients, especially ribavirin), for being used in the treatment process of the invention.

In the application, the term "liver disease" has its normal meaning, i.e., a damaged liver, more particularly a damage of the liver tissue, more particularly lesions of the liver, especially hepatic fibrosis.

The application relates more particularly to chronic liver diseases (chronic aggressions of the liver of 6 months or more).

Different diseases cause and/or lead to lesions of the liver, such as hepatic fibrosis. In particular, there may be mentioned:
viral chronic hepatitis (especially chronic hepatitis B, chronic hepatitis C, chronic hepatitis D);
steatoses and steatohepatitis (associated with the metabolic syndrome, obesity, diabetes);
alcoholic hepatitis;
genetic hemochromatosis and secondary iron overload;
autoimmune diseases;
biliary diseases (primitive biliary cirrhosis and primitive sclerosing cholangitis);
poisoning by medicament or toxic substance;
metabolic diseases;
non-alcoholic steatohepatitis (NASH).

The application is more particularly suitable for viral hepatitis, especially viral hepatitis C (HCV) and/or virus B (HBV) and/or virus D (HDV), especially viral hepatitis of at least HCV (and optionally HBV and/or HDV).

The application also relates to a computer program product intended for being stored in a memory of a processing unit, or on an immobile data carrier intended for cooperating with a reader of said processing unit. The computer program product comprises instructions for performing a process or using a product of the application, especially for performing a statistical analysis suitable for performing a process of the invention [especially suitable for the (multivariate) statistical analysis of the selected biomarkers], and/or for the constriction of a (multivariate) classification model suitable for performing a process or using a product of the invention.

The application also relates to a computer installation, computer device, computer, comprising a processing unit in the memory of which there are stored or registered:
a computer program product of the application, and optionally
values of quantification of the selected biomarkers.

The term "comprising", with which "including" or "containing" are interchangeable, is an open term that does not exclude the presence of one or more additional elements, ingredients or process steps that are not explicitly mentioned, while the term "consisting of" or "constituted of" is a closed term that excludes the presence of any other additional element, step or ingredient that is not explicitly stated. The term "essentially consisting of" or "essentially constituted of" is a partially open term that does not exclude the presence of one or more additional elements, ingredients or steps as long as these additional elements, ingredients or steps do not essentially affect the basic properties of the invention.

Consequently, the term "comprising" (or "comprises/comprise") includes the terms "consisting of", "constituted of" as well as the terms "essentially consisting of" and "essentially constituted of".

In order to facilitate the reading of the application, the description has been separated into various paragraphs, sections and embodiments. It is not to be understood that these separations disconnect the substance of a paragraph, section or embodiment from that of another paragraph, section or embodiment. On the contrary, the description encompasses all the possible combinations of different paragraphs, sections, sentences and embodiments it contains.

The content of bibliographic references quoted in the application is specifically included by reference in the content of the application.

The following Examples are given merely for illustrative purposes. They do not by any means limit the invention.

EXAMPLES

Example 1: Determination and Application of HA+CXCL10 Combinations to a Population of Patients Whose Degree of Fibrosis is Determined by Hepatic Biopsy Puncture (PBH)

The population of patients consisted of patients of the hospital Beaujon (100, boulevard du Général Leclerc; 92110 Clichy; France), who showed a chronic hepatitis as a result of infection by hepatitis C virus (HCV), covering all, or the majority, of the HCV genotypes.

The hepatic fibrosis score of these patients was determined by hepatic biopsy puncture (PBH). This population consisted of 118 patients, among whom 73 showed a fibrosis score F1, and 45 showed a fibrosis score F2 (score determined by PBH according to the Metavir F scores system, two independent readings by an approved pathologist). The studies performed were approved by the local ethics committee in accordance with the Helsinki declaration. All the patients gave their written informed consent.

The characteristics of these 118 patients are presented in Table 1 below.

The serum concentrations of the protein CXCL10 and of hyaluronic acid (HA) were measured in the serum of these patients using commercially available ELISA kits (sandwich in solid phase).

For the serum concentration of human CXCL10, the kit employed was the kit QUANTIKINE® HUMAN CXCL10/IP-10 ELISA, commercially available from R&D Systems, Inc. (614 McKinley Place NE, Minneapolis, Minn. 55413, USA), under the catalogue reference DIP100.

For the serum concentration of hyaluronic acid (HA), the kit employed was the kit HYALURONAN QUANTIKINE® ELISA, commercially available from R&D Systems, Inc. (614 McKinley Place NE, Minneapolis, Minn. 55413, USA), under the catalogue reference DHYALO.

Figure 1:
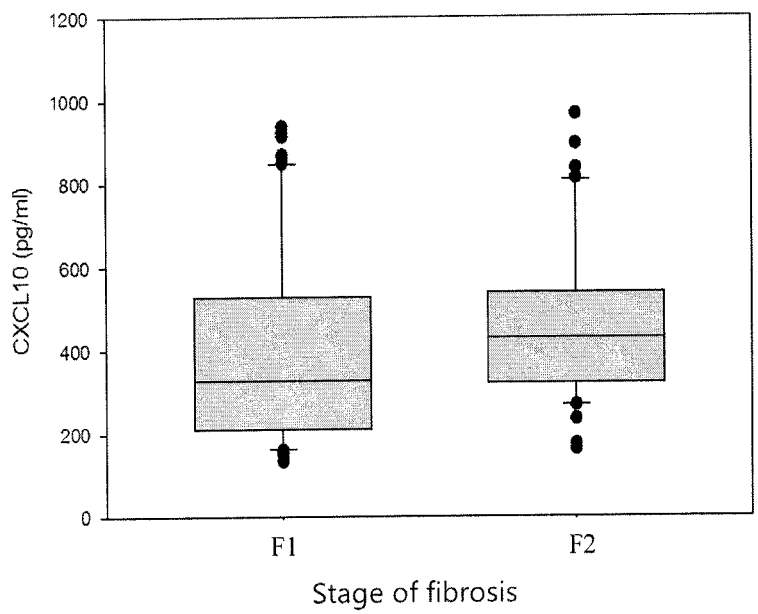
FIG. 1 presents the distribution of the protein CXCL10 serum concentration according to the hepatic fibrosis score determined by hepatic biopsy (PBH) (Metavir score F1 or F2) for a population of 118 patients (cf. Example 1 below).
Figure 2:
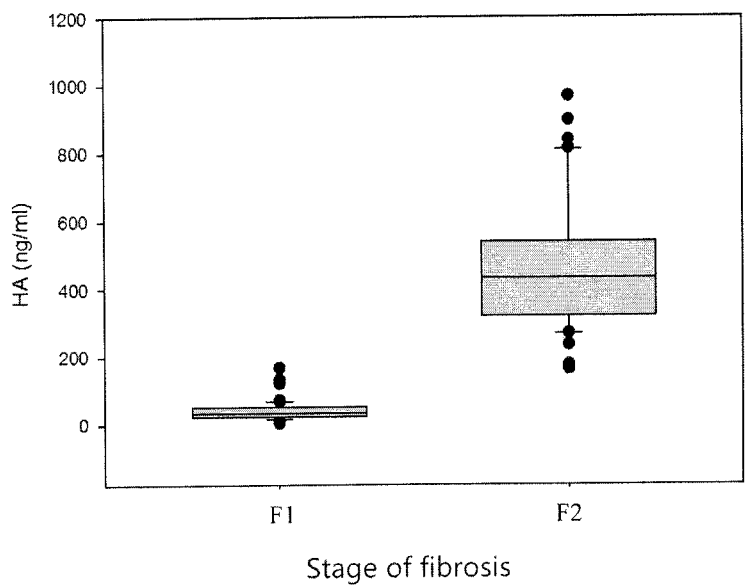
FIG. 2 presents the distribution of the hyaluronic acid (HA) serum concentration according to the hepatic fibrosis score determined by PBH (score F1 or F2) for a population of 118 patients (cf. Example 1 below).

The distribution of the concentrations of molecules CXCL10 and HA according to the hepatic fibrosis score is presented in FIG. 1 and FIG. 2, respectively.

The values of serum concentrations of CXCL10 and HA were combined by the mROC method, in order to establish a discriminating rule allowing to discriminate the patients showing a significant fibrosis (Metavir hepatic fibrosis score ≥F2) from those showing a non-significant fibrosis (Metavir hepatic fibrosis score <F2).

The values of serum concentrations of CXCL10 and HA were also combined by the mROC method with clinical parameters, such as the body mass index (BMI), the age at the sampling date (Age), and the viral load of the patient at the sampling date (VL), in order to establish a discriminating rule allowing to discriminate the patients showing a significant fibrosis (Metavir hepatic fibrosis score ≥F2) from those showing a non-significant fibrosis (Metavir hepatic fibrosis score <F2).

The mROC method is the multivariate receiver operating characteristics method as described, in particular, by Kramar et al. 1999 and Kramar et al. 2001.

The mROC method generates a linear function that combines the different biomarkers (BMQ) [$Z=a(BMQ_1)+b(BMQ_2)+\ldots$], as well as the reference value (threshold maximizing the Youden index, δ) that confers the best performances to this linear function.

The thus generated linear functions and the reference values respectively assigned thereto are listed in Table 2 below.

In this Example, much like in the other Examples and everywhere else in the text of the application, the exponent t indicated in the text of the functions "Z=" indicates that the value to apply in the linear function is the Box-Cox transformed form (Box and Cox 1964) of the value measured for the biomarker (BMQ) in order to normalize this measured value according to the following formula: $BMQ^t=(BMQ^\lambda-1)/\lambda$. The values of these parameters λ are indicated in Table 2 below.

TABLE 1

| Variables | Total population | F1 patients | F2 patients |
| --- | --- | --- | --- |
| n | 118 | 73 | 45 |
| Sex [male (%)/female (%)] | 54 (46)/64 (54) | 27 (37)/46 (63) | 27 (60)/18 (40) |
| Age on the date of sampling [mean ± SD (min-max)] | 49.1 ± 11.2 (21-71) | 46.7 ± 11.0 (21-71) | 53.1 ± 10.4 (32-71) |
| Alanine aminotransferase (ALT) IU/L [mean ± SD (min-max)] | 95 ± 83 (22-647) | 77 ± 54 (22-308) | 122 ± 111 (36-647) |
| HCV genotype [n (%)] | | | |
| 1 | 61 (52) | 34 (47) | 27 (60) |
| 2 | 15 (13) | 11 (15) | 4 (9) |
| 3 | 12 (10) | 7 (10) | 5 (11) |
| 4 | 23 (19) | 16 (22) | 7 (16) |
| 5 | 4 (3) | 3 (4) | 1 (2) |
| 6 | 2 (2) | 1 (1) | 1 (2) |
| unknown | 1 (1) | 1 (1) | 0 (0) |
| Viral load on the date of sampling (VL): copies/mL [mean (min-max)] | $5.6 \times 10^6$ ($1.4 \times 10^4$-$5.9 \times 10^7$) | $4.8 \times 10^6$ ($3.7 \times 10^4$-$2.7 \times 10^7$) | $7.0 \times 10^6$ ($1.4 \times 10^4$-$5.9 \times 10^7$) |

SD = standard deviation;
IU = international units

TABLE 2

| Biomarkers | Discriminating rule | | Threshold example |
| --- | --- | --- | --- |
| | linear function (generated by mROC) | Box-Cox normalization parameters (λ) | (threshold maximizing the Youden index (δ)) |
| CXCL10 | Z = CXCL10$^t$ | CXCL10: −0.013 | 5.611 |
| HA | Z = HA$^t$ | HA: 0.099 | 4.683 |
| HA + CXCL10 | Z = (0.3686) × CXCL10$^t$ + (0.3064) × HA$^t$ [function Z1] | CXCL10: −0.013<br>HA: 0.099 | 3.382 |
| HA + CXCL10 + BMI + Age | Z = (0.3313) × CXCL10$^t$ + (0.25154) × HA$^t$ + (0.0143) × Age$^t$ + (−9.8818) × BMI$^t$ [function Z2] | CXCL10: −0.013<br>HA: 0.099<br>Age: 1.086<br>BMI: −0.923 | −6.263 |
| HA + CXCL10 + BMI + Age + VL | Z = (0.2914) × CXCL10$^t$ + (0.2569) × HA$^t$ + (0.01419) × age$^t$ + (−9.3855) × BMI$^t$ + (0.0140) × VL$^t$ [function Z3] | CXCL10: −0.013<br>HA: 0.099<br>Age: 1.086<br>BMI: −0.923<br>VL: 0.159 | −5.730 |

In Table 2 above:

HA=serum concentration of hyaluronic acid, expressed in ng/mL

CXCL10=serum concentration of protein CXCL10, expressed in pg/mL

Age=age of the patient at the sampling date

BMI=body mass index of the patient at the sampling date (mass/height$^2$)

VL=viral load of the patient at the sampling date, expressed in $10^3$ copies per mL If applied to a patient given a function Z, then:

this patient is assigned to the class of Metavir hepatic fibrosis scores greater than or equal to F2 if the value of this function Z for this patient is greater than or equal to the threshold value maximizing the Youden index (δ) that is associated with this function Z;

conversely, this patient is assigned to the class of Metavir hepatic fibrosis scores lower than F2 if the value of this function Z for this patient is lower than the threshold value δ.

For example, for the linear function combining the biomarkers HA and CXCL10 without combining them with other markers [namely the function Z=(0.3686)×CXCL10$^t$+(0.3064)×HA$^t$]:

if the value of this function Z for a given patient is greater than or equal to the threshold value 3.382, this patient is assigned to the class of Metavir hepatic fibrosis scores greater than or equal to F2;

conversely, if the value of this function Z for a given patient is lower than the threshold value 3.382, this patient is assigned to the class of Metavir hepatic fibrosis scores lower than F2.

For example, for the linear function combining the biomarkers HA and CXCL10 as well as the biomarkers BMI and Age [namely the function Z=(0.3313)×CXCL10$^t$+(0.25154)×HA$^t$+(0.0143)×Age$^t$−(9.8818)×BMI$^t$]:

if the value of this function Z for a given patient is greater than or equal to the threshold value −6.263, this patient is assigned to the class of Metavir hepatic fibrosis scores greater than or equal to F2;

conversely, if the value of this function Z for a given patient is lower than the threshold value −6.263, this patient is assigned to the class of Metavir hepatic fibrosis scores lower than F2.

Application of these classification models to the population of 118 patients in order to discriminate the patients showing a significant fibrosis (Metavir hepatic fibrosis score ≥F2) from those showing a non-significant fibrosis (Metavir hepatic fibrosis score <F2) led to results of sensitivity (Se), specificity (Spe), positive predictive value (PPV), negative predictive value (NPV), correct classification rate (percentage of correctly classified patients) and area under the ROC curve (AUC) that are listed in Table 3 below.

TABLE 3

| Biomarkers | Rate of unclassified patients | Se | Spe | PPV | NPV | correct classification rate | AUC |
| --- | --- | --- | --- | --- | --- | --- | --- |
| CXCL10 | 0% | 73% | 55% | 50% | 77% | 62% | 0.583 |
| HA | 0% | 62% | 73% | 58% | 76% | 69% | 0.681 |
| HA + CXCL10 | 0% | 78% | 59% | 54% | 81% | 66% | 0.704 |
| HA + CXCL10 + BMI + Age | 0% | 76% | 70% | 61% | 82% | 72% | 0.729 |
| HA + CXCL10 + BMI + Age + VL | 0% | 76% | 71% | 62% | 83% | 73% | 0.731 |

Certain performances are found to be improved by the combination of biomarkers HA and CXCL10 over the same biomarkers used individually.

This is the case, in particular, with the value of AUC, which is greater than 0.7 for the combination of biomarkers HA+CXCL10, while it is lower than 0.7 for each of the biomarkers used individually:
AUC of 0.704 for the combination HA+CXCL10 without other markers [AUC of 0.729 for HA+CXCL10+BMI+Age, and AUC of 0.731 for HA+CXCL10+BMI+Age+VL], versus
AUC of 0.583 for CXCL10 used individually and of 0.681 for HA used individually.

This is also the case for the performances of sensitivity: sensitivity of 78% for the combination HA+CXCL10 without other markers [sensitivity of 76% for the combination HA+CXCL10+BMI+Age or HA+CXCL10+BMI+Age+VL], versus
sensitivity of 73% for CXCL10 used individually and of 62% for HA used individually.

This is also the case for the performances of NPV:
NPV of 81% for the combination HA+CXCL10 without other markers [sensitivity of 82% or 83% for the combination HA+CXCL10+BMI+Age or HA+CXCL10+BMI+Age+VL], versus
NPV of 77% for CXCL10 used individually and of 76% for HA used individually.

Thus, it is to note that the combination of the two biomarkers HA and CXCL10 creates a synergistic effect, going beyond the simple addition of the individual performances of these biomarkers.

This synergistic effect is unexpected because the concentration of HA and the expression of CXCL10 move in the same direction. In fact, HA induces the expression of CXCL10. Thus, if the concentration of HA increases, the expression of CXCL10 increases as well. However, it was not expected that the combination of two biomarkers that move together and in the same direction could supply additional information as compared to that supplied by each individually.

The combination of HA with CXCL10, optionally combined with one or more additional markers (clinical or anatomical marker(s) and/or virological marker(s)), showed excellent performances in determining the stage of hepatic fibrosis.

Example 2: Comparison with Non-Invasive Tests Available to the Public (Same Population of Patients as in Example 1)

The 118 patients of Example 1 were tested for comparison with tests of measuring the stage of hepatic fibrosis that are additionally available to the public (tests that are commercially available or described in scientific articles).

Five tests were performed: the test HEPASCORE™, the test FIBROTEST™, the test APRI, the test FORNS and the test SHASTA.

The test HEPASCORE™ is commercialized by QUEST DIAGNOSTICS (3 Giralda Farms, Madison, N.J. 07940, USA), and is described in Adams et al. 2005.

The test FIBROTEST™ is commercialized by BIOPREDICTIVE (40, rue du Bac, 75007 Paris, France), and is described in Imbert-Bismut et al. 2001.

The test APRI is described in Wai et al. 2003.
The test FORNS is described in Forns et al. 2002.
The test SHASTA is described in Kelleher et al. 2005.
The one of these tests that is most often used currently is the test FIBROTEST™.

Each of these tests was performed in accordance with the instructions from the manufacturer, or if applicable, in accordance with the instructions from the authors of the scientific article.

The parameters of these five tests are reported in Table 4 below.
A2M=concentration of alpha 2 macroglobulin
GGT=concentration of gamma glutamyl transpeptidase
APOA1=concentration of apolipoprotein A1
Hapto=concentration of haptoglobin
Bilirubin=concentration of total bilirubin
ASAT=concentration of aspartate aminotransferase
Platelets=concentration of platelets
Cholesterol=concentration of total cholesterol
Albumin=concentration of albumin
AST=concentration of aspartate aminotransferase
HA=concentration of hyaluronic acid
Age=age at the date of sampling
Sex=sex of the patient (female or male)

TABLE 4

| | Name of test | | | | | |
|---|---|---|---|---|---|---|
| | FIBROTEST ™ | HEPASCORE ™ | APRI | FORNS | SHASTA | |
| Number of biomarkers involved in the test | 7 including 5 biochemical biomarkers requiring determination | 6 including 4 biochemical biomarkers requiring determination | 2 | 4 including 3 biochemical biomarkers requiring determination | 3 | |
| Biochemical biomarkers | A2M GGT APOA1 Hapto Bilirubin | A2M GGT Bilirubin HA | ASAT Platelets | GGT Platelets Cholesterol | Albumin AST HA | |
| Clinical biomarkers | Age Sex | Age Sex | — | Age | — | |
| Reference thresholds recommended by the test | 0.48: ≥F2 0.28: <F2 from 0.28 to 0.47: non-determined patients who cannot be classified | ≥0.5: ≥F2 <0.5: <F2 | >1.5: ≥F2 ≤0.5: <F2 from 0.5 to 1.5: non-determined patients who cannot be classified | >6.9: ≥F2 <4.21: <F2 from 4.21 to 6.9: non-determined patients who cannot be classified | Threshold 1 ≥0.8: ≥F2 <0.8: <F2 | Threshold 2 ≥0.3: ≥F2 <0.3: <F2 |

These five non-invasive tests were applied to the population of 118 patients of Example 1 in order to discriminate the patients showing a significant fibrosis (Metavir hepatic fibrosis score ≥F2) from those showing a non-significant fibrosis (Metavir hepatic fibrosis score <F2).

The results of sensitivity (Se), specificity (Spe), positive predictive value (PPV), negative predictive value (NPV), correct classification rate and area under the ROC curve (AUC) that have been obtained are listed in Table 5 below.

Table 5 below further shows a comparison of these results with those obtained with the combination of the biomarkers HA+CXCL10 (combinations HA+CXCL10 of Example 2 above) for the same population of patients.

TABLE 5

|  | Rate of unclassified patients | Se | Spe | PPV | NPV | Rate of correct classification (*) | Global rate of correct classification ($) |
|---|---|---|---|---|---|---|---|
| HEPASCORE ™ | 0% | 67% | 75% | 63 | 79 | 72% | 72% |
| SHASTA [threshold 1] | 0% | 51% | 15% | 27 | 33 | 29% | 29% |
| SHASTA [threshold 2] | 0% | 67% | 14% | 32 | 40 | 34% | 34% |
| FIBROTEST ™ | 22% | 74% | 68% | 59 | 81 | 71% | 55% |
| APRI | 42% | 26% | 96% | 71 | 77 | 76% | 44% |
| FORNS | 50% | 35% | 93% | 67 | 78 | 76% | 38% |
| As seen before, the results of the combination HA + CXCL10 (combinations of Example 1 according to the application, cf. Table 3 above) are: | | | | | | | |
| HA + CXCL10 | 0% | 78% | 59% | 54% | 81% | 66% | 66% |
| HA + CXCL10 + BMI + Age | 0% | 76% | 70% | 61% | 82% | 72% | 72% |
| HA + CXCL10 + BMI + Age + VL | 0% | 76% | 71% | 62% | 83% | 73% | 73% |

(*): rate calculated for patients who could be classified
($): rate calculated for the total population (n = 118)

The combination of HA with CXCL10 allows to achieve diagnostic performances at least comparable with, if not better than, the tests currently available to the public, especially in terms of global rate of correct classification, rate of correct classification, sensitivity and NPV.

In particular, it is observed that the performances achieved by the combination of HA with CXCL10 (optionally combined with one or more additional markers (clinical or anatomical marker(s) and/or virological marker(s))) are clearly better than those of tests SHASTA, APRI and FORNS.

As compared to the test FIBROTEST™, the combination of HA with CXCL10 (optionally combined with one or more additional markers (clinical or anatomical marker(s) and/or virological marker(s))) has, in particular:
the advantage of allowing a classification of all the patients, while with the test FIBROTEST™, 22% of the patients do not receive a fibrosis score, and further the advantage of requiring the determination of only two biomarkers (HA and CXCL10), while for the test FIBROTEST™, five biomarkers must be determined (A2M, GGT, APOA1, Hapto and Bilirubin).

As compared to the test HEPASCORE™, the combination of HA with CXCL10 (optionally combined with one or more additional markers (clinical or anatomical marker(s) and/or virological marker(s))) has, in particular, the advantage of requiring the determination of only two biomarkers (HA and CXCL10), while for the test HEPASCORE™, four biomarkers must be determined (A2M, GGT, Bilirubin and HA). It is also observed that the combination of HA with CXCL10 (optionally combined with one or more additional markers (clinical or anatomical marker(s) and/or virological marker(s))) shows an improved sensitivity performance over the test HEPASCORE™.

Thus, the combination of HA with CXCL10 (optionally combined with one or more additional markers (clinical or anatomical marker(s) and/or virological marker(s))) shows diagnostic performances at least as satisfactory as those of the two tests that are currently most often used, namely HEPASCORE™ and FIBROTEST™, while it is much more simple to perform (and thus quicker, less expensive, and safer).

Example 3: Determination and Application of HA+CXCL10 Combinations to a Population of Patients Independent of that of Example 1

A population of patients independent of that of Example 1 was created. This independent population consisted of 310 patients of the hospital Haut-Levêque (1, avenue Magellan; 33600 Pessac; France) showing a chronic hepatitis as a result of an infection with the hepatitis C virus (HCV), and covering all, or the majority, of the HCV genotypes.

The studies performed were approved by the local ethics committee in accordance with the Helsinki declaration. All the patients gave their written informed consent.

Since hepatic biopsy puncture (PBH) is virtually no longer used currently, the stage of fibrosis has been determined by using a combination of non-invasive tests based on different principles (blood tests and imaging), as recommended by the scientific community (cf. Castera 2012).

For this purpose, a modification of the algorithm of multivariate classification of Castera et al. was performed.

The algorithm of multivariate classification of Castera et al. is the one described in Castera et al. 2010 and Castera et al. 2014. It is based on the agreement between the results of FIBROTEST™ (blood test), and of FIBROSCAN™ (imaging).

This algorithm allows the classification of the patients into two classes (absence or presence of significant fibrosis) when the non-invasive tests (FIBROTEST™ and FIBROSCAN™) are in agreement.

When the results of the tests FIBROTEST™ and FIBROSCAN™ are incongruent, the algorithm of Castera et al. recommends that a BPH be performed.

In order to determine the stage of fibrosis without having or performing a PBH, the algorithm of Castera et al. has been modified by adding a second level of analysis. This second level of analysis aims at samples that provide incongruent results by the tests FIBROTEST™ and FIBROSCAN™. This second level of analysis performs several non-invasive tests, in this case FIBROTEST™ (FT), FIBROSCAN™ (FS), HEPASCORE™ (HS), APRI and FORNS.

The tests FIBROTEST™, HEPASCORE™, APRI and FORNS have been described in Example 2 above.

The test FIBROSCAN™ is an imaging method using transient elastography, which allows to determine the stiffness of the liver (expressed in kPa equivalent of fibrosis); cf. Castera et al. 2005. The device FIBROSCAN™ is commercialized by the company ECHOSENS (30 place d'Italie, 75013 Paris, France).

During the second level of analysis, at least three of these tests (at least three among FIBROTEST™ (FT), FIBROSCAN™ (FS), HEPASCORE™ (HS), APRI and FORNS) are applied to the samples that provided incongruent results on the first level of analysis. The stage of fibrosis obtained with each of these tests has thus been determined. The stage identified by the majority of these tests was assigned to the analyzed sample. If there is no majority, the modified algorithm envisages the assignment of the label "stage of fibrosis not determined" to the sample.

Figure 3:
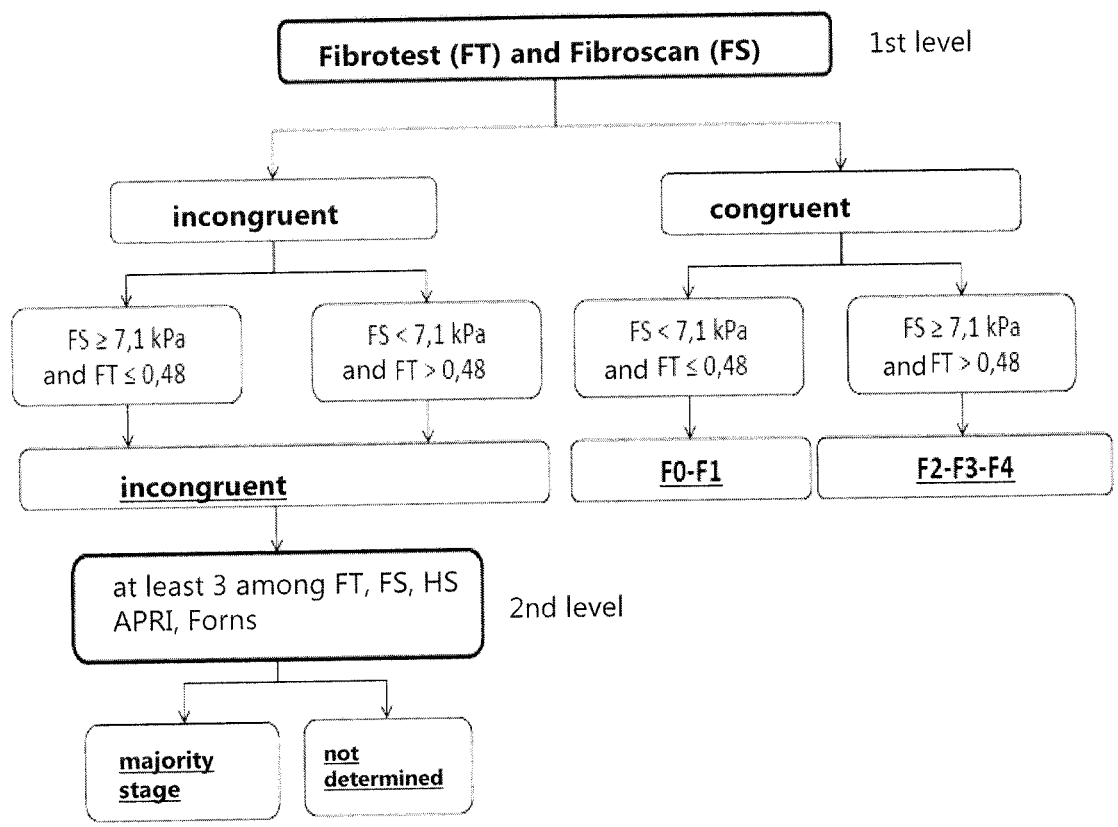
FIG. 3 presents a classification model or algorithm allowing to determine the stage of hepatic fibrosis without recurring to PBH (Metavir hepatic fibrosis score <F2 or ≥F2). This model or algorithm has been developed by modification of the algorithm described by Castera et al. (Castera et al. 2010 and Castera et al. 2014). In addition to the first analysis level (FIBROTEST™ and FIBROSCAN™), this modified model or algorithm comprises a second analysis level for the treatment (without PBH) of those samples that give incongruent results on the first analysis level (cf. Example 3 below).

The thus modified classification algorithm (or model) is shown in FIG. 3. It allows the patients to be classified into two classes according to their stage of fibrosis: significant fibrosis (Metavir hepatic fibrosis score ≥F2) and non-significant fibrosis (Metavir hepatic fibrosis score <F2), without recurring to a PBH.

The application of this modified algorithm to the created population of 310 patients allowed to identify 141 patients showing a non-significant fibrosis (Metavir hepatic fibrosis score <F2) and 169 patients showing a significant fibrosis (Metavir hepatic fibrosis score ≥F2).

The characteristics of the 310 patients are listed in Table 6 below.

TABLE 6

| Variables | Total population | Patients whose Metavir hepatic fibrosis score is < F2 | Patients whose Metavir hepatic fibrosis score is ≥ F2 |
| --- | --- | --- | --- |
| n | 310 | 141 | 169 |
| Sex [male (%)/female (%)] | 140 (45)/170 (55) | 55 (39)/86 (61) | 85 (50)/84 (50) |
| Age on the date of sampling [mean ± SD (min-max)] | 57.9 ± 11.0 (27-88) | 55.2 ± 10.0 (27-88) | 60.2 ± 11.2 (35-88) |
| Alanine aminotransferase (ALT) IU/L [mean ± SD (min-max)] | 87 ± 83 (16-795) | 54 ± 34 (16-271) | 113 ± 101 (21-795) |
| HCV genotype [n (%)] | | | |
| 1 | 213 (69) | 95 (67) | 118 (70) |
| 2 | 32 (10) | 19 (13) | 13 (8) |
| 3 | 26 (8) | 10 (7) | 16 (9) |
| 4 | 33 (11) | 13 (9) | 20 (12) |
| 5 | 3 (1) | 2 (1) | 1 (1) |
| 7 | 1 (0) | 1 (0) | 0 (0) |
| unknown | 2 (1) | 1 (0) | 1 (1) |
| Viral load on the date of sampling (VL): IU/mL [mean (min-max)] | $1.5 \times 10^6$ $(14\text{-}1.1 \times 10^7)$ | $1.5 \times 10^6$ $(14\text{-}8.9 \times 10^7)$ | $1.5 \times 10^6$ $(39\text{-}1.1 \times 10^7)$ |

SD = standard deviation;
IU = international units

Figure 4:
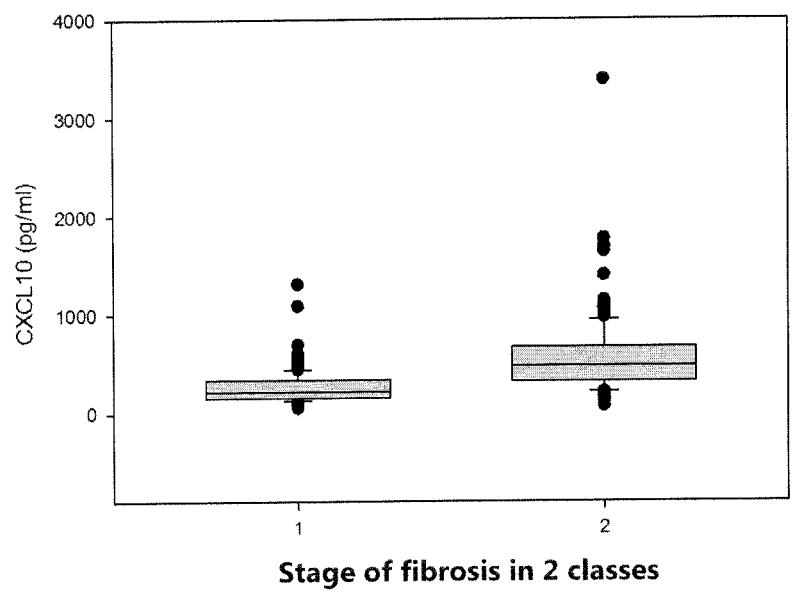
FIG. 4 presents the distribution of the protein CXCL10 serum concentration according to the degree of hepatic fibrosis (Metavir score <F2 or ≥F2) for a population of 310 patients (cf. Example 3 below).
Figure 5:
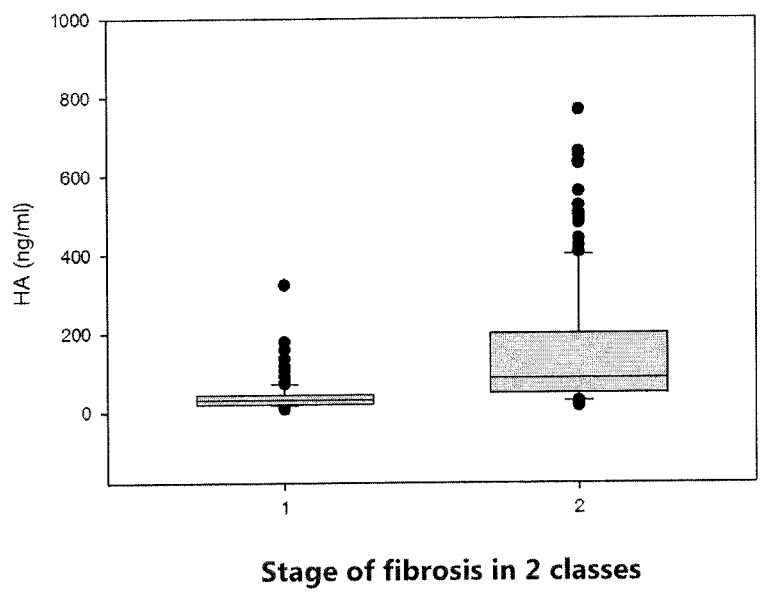
FIG. 5 presents the distribution of the hyaluronic acid (HA) serum concentration according to the degree of hepatic fibrosis (Metavir score <F2 or F2) for a population of 310 patients [cf. Example 3 below].

For each of the 310 patients of the population, the serum concentrations of HA and CXCL10 were measured as described in Example 1 above. The distribution of these concentrations according to the degree of hepatic fibrosis (Metavir score <F2 or ≥F2) is shown in FIG. 4 (CXCL10) and FIG. 5 (HA).

The values of serum concentrations of CXCL10 and HA were combined by the mROC method, in order to establish a discriminating rule allowing to discriminate the patients showing a significant fibrosis (Metavir score ≥F2) from those showing a non-significant fibrosis (Metavir score <F2).

The values of serum concentrations of CXCL10 and HA were also combined by the mROC method with clinical parameters, such as the body mass index at the sampling date (BMI), and the viral load of the patient at the sampling date (VL), in order to establish a discriminating rule allowing to discriminate the patients showing a significant fibrosis (Metavir score ≥F2) from those showing a non-significant fibrosis (Metavir score <F2).

For a description of the mROC method, cf. especially Example 1 above.

The linear function thus generated by the mROC method as well as the reference value that confers the best performances to this linear function (threshold maximizing the Youden index, δ) are shown in Table 7 below. The values of parameters λ of the Box-Cox transformed form [$BMQ^t = (BMQ^\lambda - 1)/\lambda$] are also shown in Table 7 below.

TABLE 7

| Biomarkers | Discriminating rule | | Threshold example |
| --- | --- | --- | --- |
| | linear function (generated by mROC) | Box-Cox normalization parameters (λ) | (threshold maximizing the Youden index (δ)) |
| HA | Z = HA$^t$ | HA: −0.288 | 2.330 |
| CXCL10 | Z = CXCL10$^t$ | CXCL10: −0.116 | 4.242 |
| HA + CXCL10 | Z = (1.999) × CXCL10$^t$ + (2.852) × HA$^t$ [function Z4] | CXCL10: −0.116<br>HA: −0.288 | 15.170 |
| HA + CXCL10 + BMI + Age + VL | Z = (1.999) × CXCL10$^t$ + (2.958) × HA$^t$ + (0.616) × BMI$^t$ + (−0.053) × Age$^t$ − (0.00024) × VL$^t$ [function Z5] | CXCL10: −0.116<br>HA: −0.288<br>Age: 0.433<br>BMI: −0.039<br>VL: 0.279 | 16.543 |

In Table 7 above:
HA=serum concentration of hyaluronic acid, expressed in ng/mL
CXCL10=serum concentration of protein CXCL10, expressed in pg/mL
Age=age of the patient at the sampling date
BMI=body mass index of the patient at the sampling date (mass/height$^2$)
VL=viral load of the patient at the sampling date, in IU/mL The exponent t indicated in the text of the functions "Z=" indicates that the value to apply in the linear function is the Box-Cox transformed form (Box and Cox 1964) of the value measured for the biomarker (BMQ) in order to normalize this measured value according to the following formula: BMQ$^t$=(BMQ$^\lambda$−1)/λ.

For the application of a function Z to a given patient and the comparison of the thus obtained value of Z to the threshold maximizing the Youden index, cf. Example 1 above.

Application of each of these classification models to the population of 310 patients in order to discriminate the patients showing a significant fibrosis (Metavir score ≥F2) from those showing a non-significant fibrosis (Metavir score <F2) led to results of sensitivity (Se), specificity (Spe), positive predictive value (PPV), negative predictive value (NPV), correct classification rate and area under the ROC curve (AUC) that are listed in Table 8 below.

TABLE 8

| Biomarkers | Rate of unclassified patients | Se | Spe | PPV | NPV | correct classification rate | AUC |
| --- | --- | --- | --- | --- | --- | --- | --- |
| HA | 0% | 76% | 79% | 82% | 74% | 78% | 0.840 |
| CXCL10 | 0% | 72% | 76% | 78% | 69% | 74% | 0.810 |
| HA + CXCL10 | 0% | 78% | 90% | 90% | 77% | 83% | 0.898 |
| HA + CXCL10 + BMI + Age + VL | 0% | 80% | 87% | 88% | 78% | 83% | 0.899 |

The combination of HA with CXCL10 (optionally combined with one or more additional markers (clinical or anatomical marker(s) and/or virological marker(s))) allows to obtain excellent results of classification (rate of unclassified patients, sensitivity, specificity, PPV and NPV), with only two biomarkers and without PBH.

More particularly, it is observed that the performances of Se, Spe, PPV, NPV, correct classification rate and AUC of the combination HA+CXCL10 (optionally combined with one or more additional markers (clinical or anatomical marker(s) and/or virological marker(s))) are superior to the performances of marker HA alone as well as to those of marker CXCL10 alone.

The performances of the combination HA+CXCL10 (optionally combined with one or more additional markers (clinical or anatomical marker(s) and/or virological marker(s))) thus go beyond a simple juxtaposition of the individual performances of each of the two markers of the combination.

It is thus noted that the combination of HA with CXCL10 (optionally combined with one or more clinical, anatomical, virological marker(s)) creates an unexpected synergistic effect, going beyond the simple addition of the individual performances of the biomarkers HA and CXCL10 (synergy demonstrated for a population of 310 patients).

To further demonstrate that the performances of the combination of HA with CXCL10 go beyond what could be expected from the simple addition their respective performances, a test that does not combine HA with CXCL10, but only juxtaposes them has been performed on the population of 310 patients of the Example.

This juxtaposition test is based on the fact that the simple addition of the respective performances of the biomarkers HA and CXCL10 corresponds to the addition of the information provided by HA to that provided by CXCL10: according to this juxtaposition test, the test is positive (fibrosis score greater than or equal to F2) when at least one of the two biomarkers indicates that the test is positive (fibrosis score greater than or equal to F2).

The classification obtained with the juxtaposition test is thus as follows:

TABLE 9

| Fibrosis score given by HA test alone (cf. Example 3) | Fibrosis score given by CXCL10 test alone (cf. Example 3) | Fibrosis score given by a test that juxtaposes HA to CXCL10 |
| --- | --- | --- |
| ≥F2 | ≥F2 | ≥F2 |
| ≥F2 | <F2 | ≥F2 |
| <F2 | ≥F2 | ≥F2 |
| <F2 | <F2 | <F2 |

The performances of this juxtaposition test applied to the population of 310 patients of Example 3 are as follows: rate of unclassified patients=0%; sensitivity (Se)=90%; specificity (Spe)=57%; positive predictive value (PPV)=72%; negative predictive value (NPV)=83%; correct classification rate=75%.

The presentation of these results as compared to those obtained for each of the two markers individually and as compared to those obtained with the combination of the two markers is given below.

TABLE 10

| Biomarkers | Rate of unclassified patients | Se | Spe | PPV | NPV | correct classification rate | AUC |
|---|---|---|---|---|---|---|---|
| HA alone (cf. Table 8 above) | 0% | 76% | 79% | 82% | 74% | 78% | 0.840 |
| CXCL10 alone (cf. Table 8 above) | 0% | 72% | 76% | 78% | 69% | 74% | 0.810 |
| HA/CXCL10 Test juxtaposing HA to CXCL10 | 0% | 90% | 57% | 72% | 83% | 75% | NA |
| HA + CXCL10 Test combining HA with CXCL10 (cf. Table 8 above) | 0% | 78% | 90% | 90% | 77% | 83% | 0.898 |

NA = not applicable

As compared to each marker taken individually:
the juxtaposition of HA to CXCL10 allows the sensitivity and NPV to be strongly increased as compared to each marker taken separately;
in contrast, the specificity and the PPV are reduced, which leads to a correct classification rate of 75% (intermediate between the rate obtained for HA alone and for CXCL10 alone).

In turn, when HA is combined with CXCL10, rather than a reduction of the specificity and the PPV, a very strong increase is obtained (90% versus 57% for Spe and 90% versus 72% for PPV).

This synergistic effect could not be expected either in view of the performances of specificity and PPV obtained with the juxtaposition of the two markers, or in view of those obtained with each of the two biomarkers taken individually.

In addition, the correct classification rate, which allows to evaluate the performances of the biomarkers generally, is very much better with the combination of the two biomarkers (83%) as compared to their juxtaposition (75%).

In addition, a synergistic effect was also observed in Example 1 above (population of 118 patients).

Thus, this synergistic effect does not depend on the discriminating rule employed, but more generally on the combination of HA+CXCL10.

In order to illustrate the synergistic effect of the combination of HA+CXCL10 as compared to HA alone or CXCL10 alone, the method of resampling known under the name of Bootstrap (cf. Efron 1979) was performed to evaluate the gain provided by the combination of HA+CXCL10.

Proceeding from the population of 310 patients, 1000 subpopulations of the same size were drawn randomly (draws with replacement, so that the same patient can be present several times within the same subpopulation).

The AUC values and correct classification rates were measured for each of these 1000 subpopulations:
on the one hand, when the applied mROC discriminating rule has as the coefficients those initially determined on the population of 310 patients ("fix coefficients" or "coef fix"); and
on the other hand, when the applied mROC discriminating rule has those coefficients determined for each of the 1000 subpopulations ("optimized coefficients" or "coef optim").

The AUC value is the value of the area under the ROC curve.

The value of the correct classification rate is the value of the percentage of correctly classified patients.

The results are shown in FIGS. 13A, 13B, 14A and 14B.

FIGS. 13A and 13B present the values of the differences of AUC and precision that have been measured between, on the one hand, the mROC discriminating rule with "fix coefficients" (or "coef fix") and, on the other hand, the mROC discriminating rule with "optimized coefficients" (or "coef optim") in the form of histograms.

In FIGS. 13A and 13B, the mROC discriminating rule employed the combination of HA+CXCL10.

FIG. 13A presents the histogram of the AUC differences with the fix or optimized coefficients for the combination of HA+CXCL10 in Bootstrap (B=1000) [abscissa: 0.000; 0.005; 0.010].

FIG. 13B presents the histogram of the differences of correct classification rate (percentage of correctly classified patients) with the fix or optimized coefficients for the combination of HA+CXCL10 in Bootstrap (B=1000).

As shown in FIGS. 13A and 13B, it has been noted:
that in terms of AUC, the mean of the difference is 0.001 (with a 95% confidence interval of [−0.002; 0.008]); and
that in terms of correct classification rate, the mean of the difference is 1.04 (with a 95% confidence interval of [−0.33; 3.55]).

FIGS. 13A and 13B show that there is little difference between the performances when either fix coefficients of coefficients optimized for the studied population are applied.

Thus, FIGS. 13A and 13B demonstrate that the performances are not due to the coefficients, but due to the markers themselves, since irrespective of the coefficients employed (optimized coefficients or fix coefficients), the performances obtained are comparable.

FIGS. 14A and 14B present the values of the differences of AUC and correct classification rate that have been measured for the mROC discriminating rule between, on the one hand, the combination of HA+CXCL10 and, on the other hand, the HA marker alone in the form of histograms.

FIG. 14A presents the histogram of the AUC differences between, on the one hand, the combination of HA+CXCL10 and, on the other hand, the HA marker alone in Bootstrap (B=1000) with fix coefficients ("coef fix") [abscissa: 0.02; 0.04; 0.06; 0.08; 0.10; 0.12].

FIG. 14B presents the histogram of the differences of correct classification rate (percentage of correctly classified patients) between, on the one hand, the combination of HA+CXCL10 and, on the other hand, the HA marker alone in Bootstrap (B=1000) with fix coefficients ("coef fix").

As shown in FIGS. 14A and 14B, it has been noted:
that in terms of AUC, the gain of the combination of HA+CXCL10 as compared to the marker HA alone is always greater than zero, the mean of this difference is 0.06 (with a 95% confidence interval of [0.027; 0.092]); and
that in terms of correct classification rate, gain of the combination of HA+CXCL10 as compared to the marker HA alone is greater than zero in 99% of the cases, the mean of the difference is 5.5% (with a 95% confidence interval of [1.29; 10]).

These gains confirm that the combination of HA+CXCL10 (optionally combined with one or more clinical, anatomical, virological markers) creates an unexpected synergistic effect, going beyond the simple addition of the individual performances of the biomarkers HA and CXCL10, and that this synergistic effect is independent of the classification model employed.

Example 4: Comparison with Non-Invasive Tests Available to the Public (Same Population of Patients as in Example 3)

The 310 patients of Example 3 were tested for comparison with tests of measuring the stage of hepatic fibrosis that are additionally available to the public (tests that are commercially available or described in scientific articles).

Five tests were performed: the test HEPASCORE™, the test FIBROTEST™, the test APRI, the test FORNS and the test FIBROSCAN™.

The test HEPASCORE™ is commercialized by QUEST DIAGNOSTICS (3 Giralda Farms, Madison, N.J. 07940, USA), and is described in Adams et al. 2005.

The test FIBROTEST™ is commercialized by BIOPREDICTIVE (40, rue du Bac, 75007 Paris, France), and is described in Imbert-Bismut et al. 2001.

The test APRI is described in Wai et al. 2003.

The test FORNS is described in Forns et al. 2002.

The test FIBROSCAN™ is an imaging method using transient elastography, which allows to determine the stiffness of the liver (expressed in kPa equivalent of fibrosis); cf. Castera et al. 2005. The device FIBROSCAN™ is commercialized by the company ECHOSENS (30 place d'Italie, 75013 Paris, France).

Each of these tests was performed in accordance with the instructions from the manufacturer, or if applicable, in accordance with the instructions from the authors of the scientific article.

The parameters of these five tests are reported in Table 11 below.
A2M=concentration of alpha 2 macroglobulin
GGT=concentration of gamma glutamyl transpeptidase
APOA1=concentration of apolipoprotein A1
Hapto=concentration of haptoglobin
Bilirubin=concentration of total bilirubin
ASAT=concentration of aspartate aminotransferase
Platelets=concentration of platelets
Cholesterol=concentration of total cholesterol
HA=concentration of hyaluronic acid
Age=age at the date of sampling
Sex=sex of the patient (female or male)

TABLE 11

| | Name of test | | | | |
|---|---|---|---|---|---|
| | FIBROTEST ™ | HEPASCORE ™ | APRI | FORNS | FIBROSCAN ™ |
| Number of biomarkers involved in the test | 7 including 5 biochemical biomarkers requiring determination | 6 including 4 biochemical biomarkers requiring determination | 2 | 4 including 3 biochemical biomarkers requiring determination | 0 (measurement of elastometry in kPa) |
| Biochemical biomarkers | A2M GGT APOA1 Hapto Bilirubin | A2M GGT Bilirubin HA | ASAT Platelets | GGT Platelets Cholesterol | — |
| Clinical biomarkers | Age Sex | Age Sex | — | Age | — |
| Reference thresholds recommended by the test | 0.48: ≥F2 0.28: <F2 from 0.28 to 0.47: non-determined patients who cannot be classified | ≥0.5: ≥F2 <0.5: <F2 | >1.5: ≥F2 ≤0.5: <F2 from 0.5 to 1.5: non-determined patients who cannot be classified | >6.9: ≥F2 <4.21: <F2 from 4.21 to 6.9: non-determined patients who cannot be classified | <7.1: <F2 ≥7.1: ≥F2 ≥9.5: ≥F3 ≥12.5: F4 |

These five non-invasive tests were applied to the population of 310 patients of Example 3 in order to discriminate the patients showing a significant fibrosis (Metavir hepatic fibrosis score ≥F2) from those showing a non-significant fibrosis (Metavir hepatic fibrosis score <F2).

The results of sensitivity (Se), specificity (Spe), positive predictive value (PPV), negative predictive value (NPV), correct classification rate and area under the ROC curve (AUC) that have been obtained are listed in Table 12 below.

Table 12 below further shows a comparison of these results with those obtained with the combination of the biomarkers HA+CXCL10 (combinations HA+CXCL10 of Example 3 above) for the same population of patients.

TABLE 12

| Measurements done and treated in accordance with instructions from manufacturer or from authors | Rate of unclassified patients | Se | Spe | PPV | NPV | Rate of correct classification (*) | Global rate of correct classification ($) |
|---|---|---|---|---|---|---|---|
| HEPASCORE ™ | 0% | 95% | 90% | 94% | 90% | 93% | 93% |
| FIBROSCAN ™ | 0% | 62% | 94% | 95% | 58% | 74% | 74% |
| FIBROTEST ™ | 15% | 100% | 58% | 81% | 100% | 85% | 72% |
| FORNS | 54% | 49% | 44% | 100% | 100% | 47% | 45% |
| APRI | 45% | 36% | 64% | 98% | 81% | 46% | 50% |
| As seen before, the results of the combination HA + CXCL10 (combinations of Example 3 according to the application, cf. Table 8 above) are: | | | | | | | |
| HA + CXCL10 | 0% | 78% | 90% | 90% | 77% | 83% | 83% |
| HA + CXCL10 + BMI + Age + VL | 0% | 80% | 87% | 88% | 78% | 83% | 83% |

(*): rate calculated for patients who could be classified
($): rate calculated for the total population (n = 310)

It is observed that the performances achieved by the combination of HA with CXCL10 (optionally combined with one or more additional markers (clinical or anatomical marker(s) and/or virological marker(s))) are very much better than those of tests APRI and FORNS.

As compared to the test FIBROTEST™, the combination of HA with CXCL10 (optionally combined with one or more additional markers (clinical or anatomical marker(s) and/or virological marker(s))) has, in particular:
- the advantage of allowing a classification of all the patients, while with the test FIBROTEST™, 15% of the patients of the population do not receive a fibrosis score;
- the advantage of showing better performances of specificity and PPV (in addition to the better correct classification rate); and further
- the advantage of requiring the determination of only two biomarkers (HA and CXCL10), while for the test FIBROTEST™, five biomarkers must be determined (A2M, GGT, APOA1, Hapto and Bilirubin).

As compared to the test HEPASCORE™, the combination of HA with CXCL10 (optionally combined with one or more additional markers (clinical or anatomical marker(s) and/or virological marker(s))) has, in particular, the advantage of requiring the determination of only two biomarkers (HA and CXCL10), while for the test HEPASCORE™, four biomarkers must be determined (A2M, GGT, Bilirubin and HA).

It is to be noted that the performances of the different non-invasive tests measured here with the tests HEPASCORE™, FIBROTEST™, FIBROSCAN™, APRI and FORNS (Example 4) are probably favored, given that these tests are part of the references used for determining the stage of fibrosis of the patients (cf. Example 3 above; cf. FIG. 3). This was not the case for the comparative measurements of Example 2 above (stage of fibrosis determined by PBH).

Thus, the combination of HA with CXCL10 (optionally combined with one or more additional markers (clinical or anatomical marker(s) and/or virological marker(s))) shows very satisfactory diagnostic performances, while it is much more simple to perform (and thus quicker, less expensive, and safer) as compared to the non-invasive tests that are currently available.

Example 5: Combination of the Biomarkers Ha and Cxcl10 and of Fibroscan™

The results of the test FIBROSCAN™ with the 310 patients of Example 4 were treated and analyzed by the mROC method, alone or in combination with the results of the test HA+CXCL10 of the same patients (results of HA+CXCL10 are described in Example 3 above).

For a description of the mROC method, cf. especially Example 1 above.

The linear function thus generated by the mROC method as well as the reference value (threshold maximizing the Youden index, $\delta$) that confers the best performances to this discriminating rule are shown in Table 13 below. The values of parameters $\lambda$ of the Box-Cox transformed form $[BMQ^t = (BMQ^\lambda - 1)/\lambda]$ are also shown in Table 13 below.

TABLE 13

| | Discriminating rule | | Threshold example |
|---|---|---|---|
| Biomarkers | linear function (generated by mROC) | Box-Cox normalization parameters ($\lambda$) | (threshold maximizing the Youden index ($\delta$)) |
| FS | $Z = FS^t$ | HA: −0.888 | 0.893 |
| HA + CXCL10 | $Z = (1.999) \times CXCL10^t + (2.852) \times HA^t$ [function Z4] | CXCL10: −0.116<br>HA: −0.288 | 15.170 |
| HA + CXCL10 + FS | $Z = (1.686) \times CXCL10^t + (2.216) \times HA^t + (6.947) \times FS^t$ [function Z6] | CXCL10: −0.116<br>HA: −0.288<br>FS: −0.888 | 18.375 |

In Table 13 above:
HA=serum concentration of hyaluronic acid, expressed in ng/mL
CXCL10=serum concentration of protein CXCL10, expressed in pg/mL
FS=measurement of stiffness of liver expressed in kPa equivalent fibrosis (FIBROSCAN™)

For the application of a function Z to a given patient and the comparison of the thus obtained value of Z to the threshold maximizing the Youden index, cf. Example 1 above.

Application of the above functions to the 310 patients of the population allowed their classification into stage of fibrosis <F2 and ≥F2 (Metavir score). The results of sensitivity (Se), specificity (Spe), negative predictive value (NPV), positive predictive value (PPV), correct classification rate and area under the ROC curve (AUC) are listed in Table 14 below.

TABLE 14

|   | Se | Spe | PPV | NPV | correct classification rate | AUC |
|---|----|-----|-----|-----|-----------------------------|-----|
| FS | 76% | 82% | 83% | 74% | 78% | 0.858 |
| HA + CXCL10 | 78% | 90% | 90% | 77% | 83% | 0.898 |
| HA + CXCL10 + FS | 83% | 89% | 90% | 81% | 86% | 0.931 |
| As seen before: | | | | | | |
| HA (cf. Example 3, Table 8 above) | 76% | 79% | 82% | 74% | 78% | 0.840 |
| CXCL10 (cf. Example 3, Table 8 above) | 72% | 76% | 78% | 69% | 74% | 0.810 |

The combination of HA with CXCL10 provides better diagnostic performances as compared to the test FIBROSCAN™ alone.

The combination of HA with CXCL10 and further with FS provides even better performances.

Example 6: Determination and Application of HA+CXCL10 Combinations for a Fine Classification of Fibrosis Stages (F0-F1/F2-F3/F4) (Same Population of Patients as in Example 3)

For each of the 310 patients of the population of Example 3, a fine determination of the stage of fibrosis was performed by means of an algorithm of multivariate classification.

This algorithm was developed by modification of the algorithm of Boursier et al. 2012 (cf. FIG. 2C of Boursier et al. 2012).

The algorithm of Boursier et al. 2012 was modified to allow the classification of patients that give incongruent results in FIBROSCAN™ and in FIBROTEST™ without having to recur to PBH, while allowing a fine classification of fibrosis stages (F0-F1/F2-F3/F4).

Figure 6:
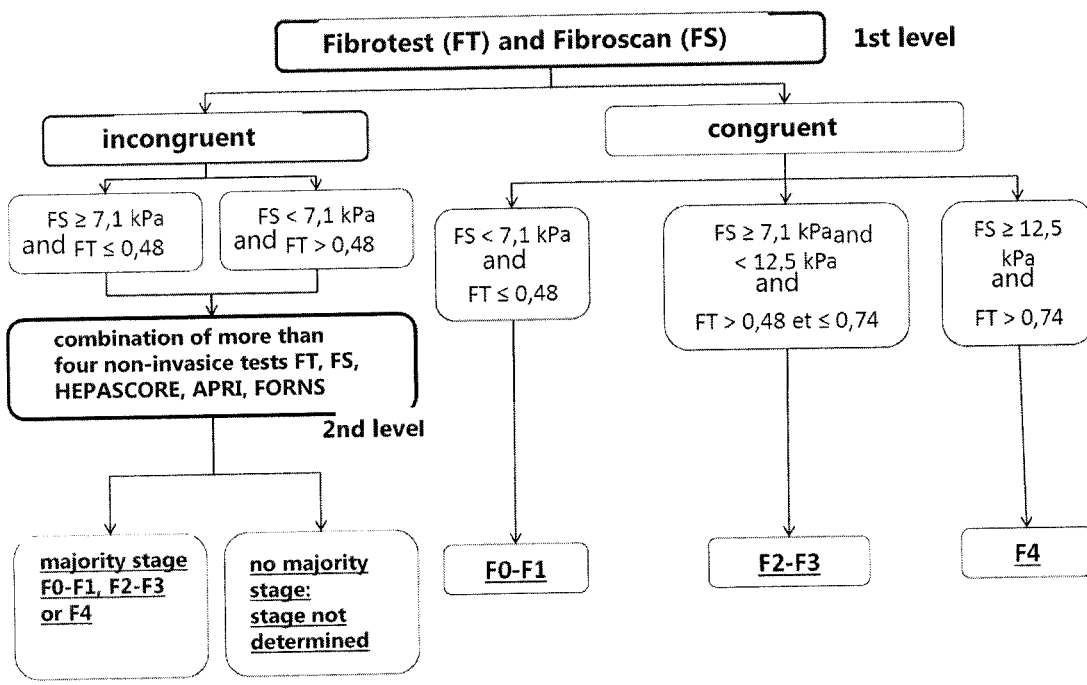
FIG. 6 presents a classification model or algorithm allowing to accurately determine the stage of hepatic fibrosis without recurring to PBH (Metavir hepatic fibrosis score F0-F1 or F2-F3 or F4). This model or algorithm has been developed by modification of the algorithm described by Boursier et al. In addition to the first analysis level (FIBROTEST™ and FIBROSCAN™), this modified model or algorithm comprises a second analysis level for the treatment (without PBH) of those samples that give incongruent results on the first analysis level (cf. Example 6 below).

The thus modified algorithm is shown in FIG. 6.

The modified algorithm comprises a second analysis level (cf. FIG. 6) using the combination of several non-invasive tests, in this case FIBROSCAN™ (FS), HEPASCORE™ (HS), APRI and FORNS.

The test FIBROSCAN™ was described in Example 3 above.

The tests HEPASCORE™, APRI and FORNS were described in Example 2 above.

During the second level of analysis, at least three of these tests are applied to the samples that provided incongruent results on the first level of analysis. The stage of fibrosis obtained with each of these tests has thus been determined.

The stage identified by the majority of these tests was assigned to the analyzed sample. If there is no majority, the modified algorithm envisages the assignment of the label "stage of fibrosis not determined" to the sample.

The characteristics of the 310 patients are listed in Table 15 below.

TABLE 15

| Variables | Total population | Patients F0-F1 | Patients F2-F3 | Patients F4 |
|-----------|------------------|----------------|----------------|-------------|
| n | 310 | 141 | 128 | 41 |
| Sex [male (%)/female (%)] | 140 (45)/170 (55) | 55 (39)/86 (61) | 57 (45)/71 (55) | 28 (68)/13 (32) |
| Age on the date of sampling [mean ± SD (min-max)] | 57.9 ± 11.0 (27-88) | 55.2 ± 10.0 (27-88) | 60.7 ± 11.3 (35-88) | 58.9 ± 11.0 (41-85) |
| Alanine aminotransferase (ALT) IU/L [mean ± SD (min-max)] | 87 ± 83 (16-795) | 54 ± 34 (16-271) | 103 ± 91 (21-795) | 149 ± 121 (23-741) |
| HCV genotype [n (%)] | | | | |
| 1 | 213 (69) | 95 (67) | 90 (70) | 28 (68) |
| 2 | 32 (10) | 19 (13) | 9 (7) | 4 (10) |
| 3 | 26 (8) | 10 (7) | 12 (9) | 4 (10) |
| 4 | 33 (11) | 13 (9) | 15 (12) | 5 (12) |
| 5 | 3 (1) | 2 (1) | 1 (0) | 0 (0) |
| 7 | 1 (0) | 1 (0) | 0 (0) | 0 (0) |
| unknown | 2 (1) | 1 (0) | 1 (0) | 0 (0) |
| Viral load on the date of sampling (VL): IU/mL [mean (min-max)] | $1.5 \times 10^6$ (14-$1.1 \times 10^7$) | $1.5 \times 10^6$ (14-$8.9 \times 10^7$) | $1.7 \times 10^6$ (39-$1.1 \times 10^7$) | $1.0 \times 10^6$ ($1.3 \times 10^3$-$4.2 \times 10^6$) |

SD = standard deviation;
IU = international units

Figure 7:
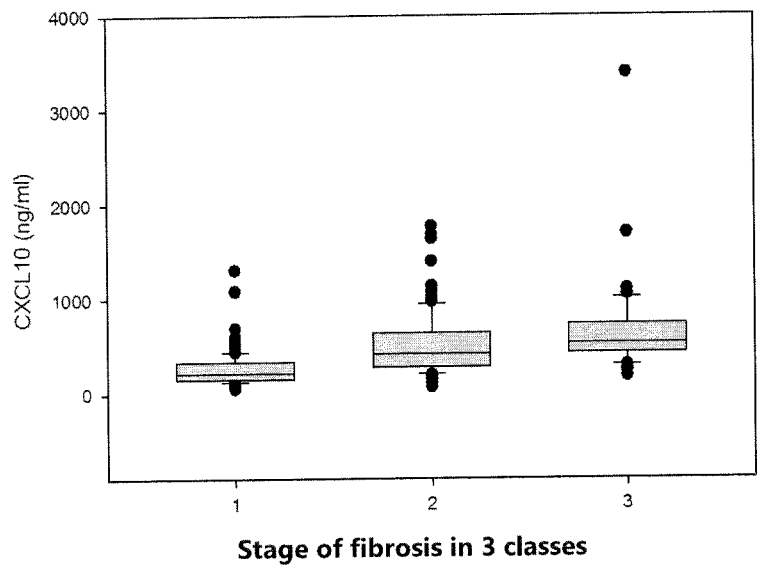
FIG. 7 presents the distribution of the protein CXCL10 serum concentration according to the degree of hepatic fibrosis (Metavir score F0-F1 or F2-F3 or F4) for a population of 310 patients (cf. Example 6 below).
Figure 8:
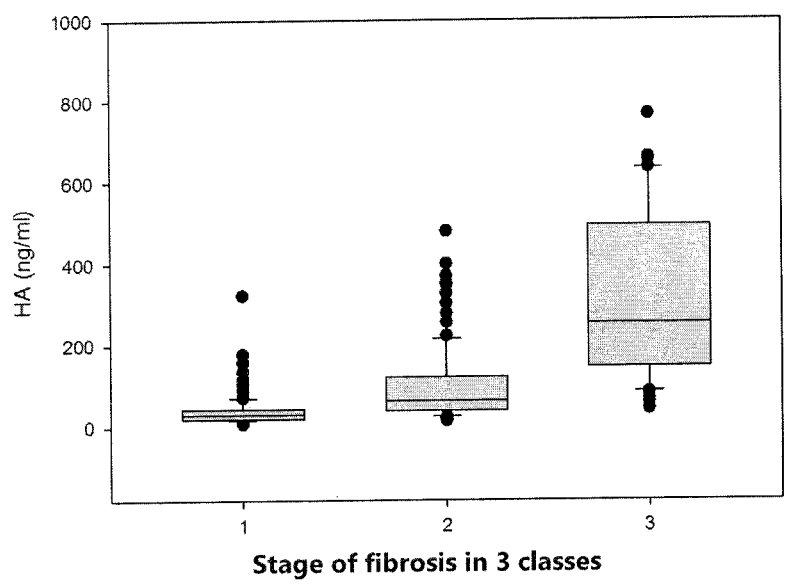
FIG. 8 presents the distribution of the hyaluronic acid (HA) serum concentration according to the degree of hepatic fibrosis (Metavir score F0-F1 or F2-F3 or F4) for a population of 310 patients (cf. Example 6 below).

For each of the 310 patients of the population, the serum concentrations of HA and CXCL10 were measured as described in Example 1 above. The distribution of these concentrations according to the degree of hepatic fibrosis (Metavir score F0-F1 or F2-F3 or F4) is shown in FIG. 7 (CXCL10) and FIG. 8 (HA). The measurements of FIBROSCAN™ (stiffness of the liver expressed in kPa equivalent fibrosis) were compared to the threshold value recommended by this test to classify the stage of hepatic fibrosis with respect to the Metavir score F4, namely a threshold of 12.5 kPa. In accordance with the instructions from the manufacturer:

- those patients whose value of measurement by FIBROSCAN™ (FS) was lower than 12.5 kPa were assigned to the class "Metavir hepatic fibrosis score lower than F4"; and
- those patients whose value of measurement by FIBROSCAN™ (FS) was higher than or equal to 12.5 kPa were assigned to the class "Metavir hepatic fibrosis score=F4".

The patients whose Metavir hepatic fibrosis score was thus determined to be lower than F4 were previously classified by means of the combination of markers HA+CXCL10 (2nd level of analysis). For this purpose, the values of serum concentrations of CXCL10 and HA were combined by the mROC method in order to establish a discriminating rule allowing the stage of fibrosis to be determined (Metavir score F0-F1 or F2-F3). The values of serum concentrations of CXCL10 and HA were also combined:

- with clinical parameters, such as the body mass index (BMI), the age and the viral load of the patient (VL);
- with the values measured by FIBROSCAN™;

in accordance with the mROC method in order to establish a discriminating rule allowing the stage of fibrosis to be determined (Metavir score F0-F1 or F2-F3).

For a description of the mROC method, cf. especially Example 1 above. The linear function thus generated by the mROC method and the reference value (threshold maximizing the Youden index, $\delta$) that confers the best performances to this discriminating rule are shown in Table 16 below. The values of parameters $\lambda$ of the Box-Cox transformed form $[BMQ^t=(BMQ^\lambda-1)/\lambda]$ are also shown in Table 16 below.

FIGS. 9, 10 and 11 show an illustration of the algorithm of multivariate classification thus developed and applied.

TABLE 16

| Biomarkers | Discriminating rule linear function (generated by mROC) | Box-Cox normalization parameters ($\lambda$) | Threshold example (threshold maximizing the Youden index ($\delta$)) | Algorithm of multivariate classification |
|---|---|---|---|---|
| HA + CXCL10 | $Z = (1.849) \times CXCL10^t + (2.368) \times HA^t$ [function $Z_7$] | HA: −0.27<br>CXCL10: −0.116 | 13.5 | FIG. 11 |
| HA + CXCL10 + BMI + Age + VL | $Z = (1.853) \times CXCL10^t + (2.511) \times HA^t + (-0.00027) \times VL^t + (-0.0343) \times age^t + (0.4246) \times BMI^t$ [function $Z_8$] | HA: −0.27<br>CXCL10: −0.116<br>VL: 0.288<br>Age: 0.536<br>BMI: 0.056 | 14.7 | FIG. 12 |
| HA + CXCL10 + FS | $Z = (1.585) \times CXCL10^t + (2.181) \times HA^t + (2.910) \times FS^t$ [function $Z_9$] | HA: −0.27<br>CXCL10: −0.116<br>FS: −0.27 | 15.7 | FIG. 13 |

FS = measurement of stiffness of liver expressed in kPa equivalent fibrosis (FIBROSCAN ™)

In Table 16 above:

HA=serum concentration of hyaluronic acid, expressed in ng/mL

CXCL10=serum concentration of protein CXCL10, expressed in pg/mL

FS=FIBROSCAN™=measurement of stiffness of liver expressed in kPa equivalent fibrosis Age=age of the patient at the sampling date BMI=body mass index at the sampling date (mass/height$^2$)

VL=viral load of the patient at the sampling date, in IU/mL

The exponent t indicated in the text of the functions "Z=" indicates that the value to apply in the linear function is the Box-Cox transformed form (Box and Cox 1964) of the value measured for the biomarker (BMQ) in order to normalize this measured value according to the following formula: $BMQ^t=(BMQ^\lambda-1)/\lambda$.

For the application of a function Z to a given patient and the comparison of the thus obtained value of Z to the threshold maximizing the Youden index, cf. Example 1 above.

Each of the functions Z shown in Table 16 above can be directly assigned to a patient whose Metavir hepatic fibrosis score is lower than F4.

If the patient's hepatic fibrosis score is known, and if this score is lower than the Metavir score F4, an examination by FIBROSCAN™ (or any other examination) in advance is not necessary: a formula Z of Table 16 can be directly applied to the data from this patient.

In contrast, if the patient's hepatic fibrosis score is not known, an examination must be performed in order to determine if this score is lower than F4, for example, by FIBROSCAN™, and then proceed as shown in FIG. 9, 10 or 11 according to the selected Z formula.

The application of this classification to the 310 patients of the population allowed the patients to be classified into 3 fibrosis states (Metavir hepatic fibrosis score F0-F1 or F2-F3 or F4) with the correct classification rates as shown in Table 17 below.

TABLE 17

(correct classification rates):

| Combination applied to those patients whose Metavir hepatic fibrosis score is lower than F4 | Correct classification rate | | | |
|---|---|---|---|---|
| | Metavir hepatic fibrosis score | | | |
| | F0-F1 | F2-F3 | F4 (score known or determined by FIBROSCAN ™) | Total population |
| Combination HA + CXCL10 | 89% | 69% | 100% | 82% |
| Combination HA + CXCL10 + VL + Age + BMI | 84% | 73% | 100% | 82% |
| Combination HA + CXCL10 + FS | 82% | 84% | 100% | 85% |

The combination of HA with CXCL10, optionally combined with one or more additional markers (clinical or anatomical marker(s) and/or virological marker(s)), allows excellent correct classification rates to be achieved among the population of patients whose Metavir hepatic fibrosis score is lower than F4.

Example 7 methods not based on a linear function can be used; and experimental demonstration of a general mROC formulation The mROC method is a method of multivariate classification based on a linear function. For a description of the mROC method, cf. Example 1. For examples of mROC linear functions, cf. Examples 1 to 6 above.

The methods of multivariate classification that, like the mROC method, are based on a linear function are not the only methods that can be performed to establish a model of classification of patients using the combination of biomarkers CXCL10 and HA.

In fact, methods of multivariate classification that are not based on a linear function can be used. For example, there can be used:
methods of multivariate classification based on a function that is not a linear function, for example, methods of multivariate classification based on an affine function, such as the method of logistic regression (LR); or
methods of multivariate classification that are not based on a (mathematical) function, such as methods based on a decision tree, for example, the CART (Classification And Regression Tree) method.

The model of logistic regression was described by Berkson 1944.

The CART model was described by Breiman et al. 1984.

The population of patients is identical with that presented in Example 3 above. This population consisted of 310 patients whose state of fibrosis was determined according to the classification algorithm shown in FIG. 3. The characteristics of these patients are shown in Table 6 above.

A learning group and a validation group were drawn randomly with 10 replacements among the population of 310 patients.

The learning group consisted of ⅔ of the patients, i.e., 207 patients, and the validation group consisted of ⅓ of the patients, i.e., 103 patients.

Three methods are compared:
the mROC method (with linear function);
the LR method (with affine function);
the CART method (no mathematical function; classification by decision tree).

The mROC functions employed are those of Example 3 above (cf. Table 7 above). For the record:

TABLE 18

| | Discriminating rule | | Threshold example |
|---|---|---|---|
| Biomarkers | linear function (generated by mROC) | Box-Cox normalization parameters ($\lambda$) | (threshold maximizing the Youden index ($\delta$)) |
| HA | Z = HA$^t$ | HA: −0.288 | 2.330 |
| CXCL10 | Z = CXCL10$^t$ | CXCL10: −0.116 | 4.242 |
| HA + CXCL10 | Z = (1.999) × CXCL10$^t$ + (2.852) × HA$^t$ [function Z4] | CXCL10: −0.116 HA: −0.288 | 15.170 |

The exponent t indicated in the text of the functions "Z=" indicates that the value to apply in the linear function is the Box-Cox transformed form (Box and Cox 1964) of the value measured for the biomarker (BMQ) in order to normalize this measured value according to the following formula: $BMQ^t = (BMQ^\lambda - 1)/\lambda$.

The classification models CART and LR were established on learning groups (cf. Table 19 below).

TABLE 19

| | | Discriminating rule | | |
|---|---|---|---|---|
| Method | Marker(s) | Function or decision tree | Parameters | Example of threshold(s) |
| CART | HA + CXCL10 | cf. FIG. 12 | NA | h ∈ [42.18; 77.4] i ∈ [209.3; 266.7] j ∈ [454.7; 553.1] [CART$_3$ tree] |
| | HA | if HA < threshold, the score is < F2 if HA ≥ threshold, the score is ≥ F2 | NA | threshold ∈ [42.18; 77.4] |
| | CXCL10 | if CXCL10 < threshold, the score is < F2 if CXCL10 ≥ threshold, the score is ≥ F2 | NA | threshold ∈ [220.8; 440.3] |
| LR | HA + CXCL10 | LOGIT = Intercept + k(CXCL10) + I(HA) [function LOGIT$_3$] | Intercept ∈ [−3.57; −2.67] k ∈ [0.003; 0.007] I ∈ [0.02; 0.04] | Logit = 0.5 |
| | HA | LOGIT = Intercept + I(HA) | Intercept ∈ [−2.13; −1.36] I ∈ [0.02; 0.04] | |
| | CXCL10 | LOGIT = Intercept + k(CXCL10) | Intercept ∈ [−2.41; −1.55] k ∈ [0.005; 0.007] | |

The values of the parameters shown in Table 19 above (LR method) correspond to the lower and upper limits of the values of the parameters of the 10 randomly drawn populations.

The performances were validated on the validation group (Metavir hepatic fibrosis score lower than F2, or Metavir hepatic fibrosis score higher than or equal to F2).

The mean values of the results of sensitivity (Se), specificity (Spe), negative predictive value (NPV), positive predictive value (PPV), area under the ROC curve (AUC) and correct classification rate, which were obtained from the set of 10 replicates for the learning group and for the validation group, are shown in Table 20 and Table 21 below, respectively.

TABLE 20

| | | Learning group n = 207 | | | | | |
|---|---|---|---|---|---|---|---|
| Combination | Method | Se | Spe | PPV | NPV | Correct classification rate | AUC |
| HA + CXCL10 | mROC | 76 | 92 | 92 | 76 | 83 | 0.898 |
| HA | mROC | 78 | 79 | 82 | 75 | 78 | 0.845 |
| CXCL10 | mROC | 72 | 75 | 78 | 70 | 74 | 0.802 |
| HA + CXCL10 | CART | 77 | 91 | 91 | 77 | 83 | NA |
| HA | CART | 78 | 79 | 82 | 75 | 78 | NA |
| CXCL10 | CART | 72 | 75 | 78 | 70 | 74 | NA |
| HA + CXCL10 | LR | 76 | 86 | 86 | 75 | 80 | 0.878 |
| HA | LR | 68 | 84 | 84 | 68 | 75 | 0.845 |
| CXCL10 | LR | 72 | 73 | 76 | 68 | 72 | 0.802 |

TABLE 21

| | | Validation group n = 103 | | | | | |
|---|---|---|---|---|---|---|---|
| Markers | Method | Se | Spe | PPV | NPV | Correct classification rate | AUC |
| HA + CXCL10 | mROC | 76 | 88 | 88 | 76 | 81 | 0.898 |
| HA | mROC | 76 | 73 | 78 | 73 | 75 | 0.831 |
| CXCL10 | mROC | 73 | 71 | 77 | 70 | 72 | 0.832 |
| HA + CXCL10 | CART | 78 | 91 | 91 | 78 | 84 | NA |
| HA | CART | 76 | 73 | 78 | 73 | 75 | NA |
| CXCL10 | CART | 73 | 71 | 77 | 70 | 72 | NA |
| HA + CXCL10 | LR | 78 | 86 | 87 | 77 | 82 | 0.888 |
| HA | LR | 68 | 83 | 83 | 68 | 75 | 0.831 |
| CXCL10 | LR | 77 | 72 | 77 | 72 | 75 | 0.832 |

HA = serum concentration of hyaluronic acid (HA), in ng/mL
CXCL10 = serum concentration of protein CXCL10 (CXCL10), in pg/mL
NA = not applicable Thus, it could be ascertained that the performances of the combination HA+CXCL10 are superior to those of HA alone or those of CXCL10 alone. In particular, this applies to the performances specificity, PPV, NPV, correct classification rate and AUC.

The fact that the combination of HA with CXCL10 reaches better performances than those of marker HA alone and then those of marker CXCL10 alone indicates that the combination HA+CXCL10 has a synergistic effect that goes beyond that of a simple juxtaposition of the two markers (on the topic of synergy, cf. also Examples 1 and 3 above).

It is also noted that the performances are similar irrespective of the method of multivariate classification employed.

The performances, more particularly the synergistic effect, of the combination of HA and CXCL10 do not depend on the nature of the method of multivariate classification employed.

This proves that a method of multivariate classification other than mROC can be used.

More particularly, alternatively to the methods of multivariate classification based on a linear function, such as mROC, there can be employed:
- methods of multivariate classification based on a function that is not a linear function, for example, methods of multivariate classification based on an affine function, such as the LR method;
- as well as classification methods that are not based on a (mathematical) function, such as methods based on a decision tree, for example, the CART method.

The methods mROC, CART and LR were also applied to the total population of 310 patients of Example 3. Examples of discriminating rules obtained on the population of 310 patients for the methods CART and LR are presented in Table 22 below (Metavir hepatic fibrosis score lower than F2, or Metavir hepatic fibrosis score higher than or equal to F2). The mROC functions employed are those of Example 3 above (cf. Table 7 above).

TABLE 22

| | Discriminating rule | | |
|---|---|---|---|
| Method | Function or decision tree | Parameters | Example of threshold(s) |
| mROC | $Z = a \times (CXCL10^r) + b \times (HA^r)$ [function $Z_4$] | $a = 1.999$<br>$b = 2.852$<br>$\lambda_{CXCL10} = -0.116$<br>$\lambda_{HA} = -0.288$ | $\delta_1 = 15.170$ |
| mROC | $Z = a \times (CXCL10^r) + b \times (HA^r) + c \times (BMI^r) + d \times (age^r) + e \times (VL^r)$ [function $Z_5$] | $a = 1.999$<br>$b = 2.958$<br>$c = 0.616$<br>$d = -0.053$<br>$e = -0.00024$<br>$\lambda_{CXCL10} = -0.116$<br>$\lambda_{HA} = -0.288$<br>$\lambda_{BMI} = -0.039$<br>$\lambda_{Age} = 0.433$<br>$\lambda_{VL} = 0.279$ | $\delta_2 = 16.543$ |
| CART | cf. FIG. 12 | NA | $h = 47.29$<br>$i = 209.3$<br>$j = 503.4$<br>[$CART_4$ tree] |
| LR | LOGIT = Intercept + k(CXCL10) + l(HA), [function $LOGIT_4$] | Intercept = $-3.164$<br>$k = 0.005$<br>$l = 0.024$ | Logit = 0.5 |

HA = serum concentration of hyaluronic acid, in ng/mL
CXCL10 = serum concentration of protein CXCL10, in pg/mL In accordance with the mROC method, if the value of the function $Z_4$ for a given patient was greater than or equal to 15.170 (combination HA+CXCL10), this patient was assigned to a Metavir hepatic fibrosis score greater than or equal to F2. In contrast, if the value of the function $Z_4$ for a given patient was lower than 15.170, this patient was assigned to a Metavir hepatic fibrosis score lower than F2.

Similarly, if the value of the function $Z_5$ for a given patient was greater than or equal to 16.543 (combination HA+CXCL10+BMI+Age+VL), this patient was assigned to a Metavir hepatic fibrosis score greater than or equal to F2. In contrast, if the value $Z_5$ for a given patient was lower than 16.543, this patient was assigned to a Metavir hepatic fibrosis score lower than F2.

In accordance with the CART method (cf. FIG. 12), if the serum concentration of hyaluronic acid (HA) in ng/mL of a patient was lower than the value of the parameter h (47.29), they were assigned:

a Metavir hepatic fibrosis score lower than F2 if their serum concentration of protein CXCL10 in pg/mL was lower than the value of the parameter j (503.4); and a Metavir hepatic fibrosis score greater than or equal to F2 if their serum concentration of protein CXCL10 in pg/mL was greater than or equal to the value of parameter j (503.4).

Similarly, in accordance with the CART method (cf. FIG. 12), if the serum concentration of hyaluronic acid (HA) in ng/mL of a patient was higher than the value of the parameter h (47.29), they were assigned:

a Metavir hepatic fibrosis score lower than F2 if their serum concentration of protein CXCL10 in pg/mL was lower than the value of the parameter i (209.3); and a Metavir hepatic fibrosis score greater than or equal to F2 if their serum concentration of protein CXCL10 in pg/mL was greater than or equal to the value of parameter i (209.3).

In accordance with the LR method, if the value of the LOGIT function for a given patient was greater than or equal to the value of the LOGIT threshold (0.5), this patient was assigned to a Metavir hepatic fibrosis score greater than or equal to F2. In contrast, if the value of the LOGIT function for a given patient was lower than the value of the LOGIT threshold (0.5), this patient was assigned to a Metavir hepatic fibrosis score lower than F2.

The results of sensitivity (Se), specificity (Spe), negative predictive value (NPV), positive predictive value (PPV), area under the ROC curve (AUC) and the correct classification rate that have been obtained for these discriminating rules on the population of 310 patients are presented in Table 23 below.

TABLE 23

| | | Total population n = 310 | | | | | |
|---|---|---|---|---|---|---|---|
| Combination | Method | Se | Spe | PPV | NPV | Correct classification rate | AUC |
| HA + CXCL10 | mROC | 78 | 90 | 90 | 77 | 83 | 0.898 |
| HA + CXCL10 + BMI + Age + VL | mROC | 80 | 87 | 88 | 78 | 83 | 0.899 |
| HA + CXCL10 | CART | 82 | 89 | 90 | 80 | 85 | NA |
| HA + CXCL10 | LR | 77 | 87 | 87 | 76 | 81 | 0.882 |

HA = serum concentration of hyaluronic acid (HA), in ng/mL
CXCL10 = serum concentration of protein CXCL10 (CXCL10), in pg/mL
Age = age of the patient at the sampling date
BMI = body mass index of the patient at the sampling date (mass/height$^2$)
VL = viral load of the patient at the sampling date, in IU/mL
NA = not applicable Thus, it could be ascertained that the performances of the combination of the biomarker HA with the biomarker CXCL10 are totally independent of the nature of the method of multivariate classification employed.

Example 8: General Formulation

The ranges of values of the parameters and thresholds employed by the classification methods can be calculated by using the Bootstrap method (cf. Efron 1979). In accordance with this method, a random population of 310 patients was drawn randomly 1000 times in succession.

The results of these calculations for the methods mROC, CART and LR are presented in Table 24 below.

TABLE 24

| Multivariate classification method | Discriminating rule | Parameters | Example of threshold(s) | Performance |
|---|---|---|---|---|
| | mROC $Z = a(CXCL10^r) + b(HA^r)$ [function $Z_{10}$] | $0.812 \leq a \leq 5.089$ $2.033 \leq b \leq 4.462$ $-0.262 \leq \lambda_{CXCL10} \leq 0.030$ $-0.382 \leq \lambda_{HA} \leq -0.219$ | $11.68 \leq \delta \leq 23.71$ | AUC $\geq 0.865$ [$0.865 \leq$ AUC $\leq 0.931$] CCR $\geq 80\%$ [$80\% \leq$ CCR $\leq 88\%$] |
| | mROC $Z = a(CXCL10^r) + b(HA^r) + c(BMI^r) + d(age^r) + e(VL^r)$ [function $Z_{11}$] | $0.748 \leq a \leq 5.357$ $2.075 \leq b \leq 4.690$ $-0.848 \leq c \leq 3.697$ $-0.746 \leq d \leq 0.147$ $-0.003 \leq e \leq 0.002$ $-0.262 \leq \lambda_{CXCL10} \leq 0.047$ $-0.882 \leq \lambda_{HA} \leq -0.219$ $-5.545 \leq \lambda_{BMI} \leq 0.485$ $-0.116 \leq \lambda_{age} \leq 0.828$ $0.236 \leq \lambda_{VL} \leq 0.305$ | $11 \leq \delta \leq 25.87$ | AUC $\geq 0.868$ [$0.868 \leq$ AUC $\leq 0.933$] CCR $\geq 80\%$ [$80\% \leq$ CCR $\leq 88\%$] |
| Multivariate classification method not based on a linear function | CART (Classification And Regression Tree) cf. FIG. 12 (markers HA and CXCL10) | NA | $41.96 \leq h \leq 77.43$ $159.0 \leq i \leq 266.7$ $410.7 < j < 613.5$ [CART$_2$ tree] | CCR $\geq 81\%$ [$81\% \leq$ CCR $\leq 89\%$] |
| | LR (logistic regression) LOGIT = Intercept + k(CXCL10) + l(HA) [function LOGIT$_2$] | $-4.481 \leq$ Intercept $\leq -2.398$ $0.003 \leq k \leq 0.008$ $0.013 \leq l \leq 0.045$ | Logit = 0.5, for example | AUC $\geq 0.844$ [$0.844 \leq$ AUC $\leq 0.921$] CCR $\geq 77\%$ [$77\% \leq$ CCR $\leq 86\%$] |

CCR = correct classification rate;
NA = not applicable

In Table 24, a, b, c, d, e, $\lambda_{CXCL10}$, $\lambda_{HA}$, $\lambda_{BMI}$, $X_{VL}$, Intercept, k and l are each different from zero.

The set of different mROC functions can thus be formulated as follows:

$$Z=a(CXCL10^r)+b(HA^r)+c(BMI^r)+d(age^r)+e(VL^r)+f(FS^r) \quad \text{[function } Z_{12}\text{]}$$

with:
a and b each being independently a positive real number going from +0.1 to +6.0, more particularly from +0.3 to +5.5;
c being a real number going from −10.0 to +4.0;
d being a real number going from −0.8 to +0.2;
e being a real number going from −0.003 to +0.002;
f being a real number going from +0.0 to +10.0;
$\lambda_{CXCL10}$, $\lambda_{HA}$, $\lambda_{BMI}$, $\lambda_{age}$, $\lambda_{VL}$ and $\lambda_{FS}$ each being independently a real number going from −6.0 to 1.2, but excluding zero.

The set of different mROC functions can thus be formulated as follows:

$$Z=a(CXCL10^r)+b(HA^r)+c(BMI^r)+d(age^r)+e(VL^r)+f(FS^r) \quad \text{[function } Z_{13}\text{]}$$

with:
a and b each being independently a positive real number going from +0.1 to +6.0;
c, d, e and f each being independently a real number going from −10.0 to +10.0;
$\lambda_{CXCL10}$, $\lambda_{HA}$, $\lambda_{BMI}$, $\lambda_{age}$, $\lambda_{VL}$ and $\lambda_{FS}$ each being independently a real number going from −6.0 to 1.2, but excluding zero.

The set of LOGIT functions can thus be formulated as follows:

$$\text{LOGIT}=\text{Intercept}+k(CXCL10)+l(AH), \quad \text{[function } \text{LOGIT}_1\text{]}$$

with
$-5 \leq \text{Intercept} \leq -1$
$0.001 \leq k \leq 0.010$
$0.010 \leq l \leq 0.050$.

The set of different CART trees can be formulated as follows:
Decision tree of FIG. 12 with:
$40 \leq h \leq 80$
$150 \leq i \leq 300$
$400 \leq j \leq 620$
[$CART_1$ tree].

For each mROC function or LR function or CART tree, the values of the parameters can be selected in accordance with the indicated ranges of values.

Once the value of each of the parameters has been chosen, the mROC function or LR function or CART tree resulting therefrom can be tested on a reference population, for example, on a population of 310 patients as described in Example 3. Thus, it can be tested, for example, that with the chosen parameters, the mROC function or LR function or CART tree actually leads to the expected or desired performances, especially to the expected or desired value of AUC and/or value of correct classification rate.

The performances can be measured on a population of HCV-positive patients having a stage of hepatic fibrosis covering at least stages F1 to F3 (Metavir score), such as the population of 118 patients of Example 1 or the population of 310 patients of Example 3.

The associated threshold can, for example, be the threshold maximizing the Youden index, δ, whose value is a real number going from −7 to 25.

Example 9: Robustness of the Combination HA+CXCL10

To illustrate the robustness of the combination HA+CXCL10, the resampling method known by the name of Bootstrap (cf. Efron 1979) was performed on the population of 310 patients of Example 3 above.

From this population of 310 patients, 1000 subpopulations of the same size were drawn randomly (draws with replacement, so that the same patient can be present several times within the same subpopulation).

The values of AUC and of correct classification rate were measured on each of these 1000 subpopulations:
on the one hand, when the applied mROC discriminating rule has the coefficients and threshold initially established on the population of 310 patients ("fix coefficients" or "coef fix"); and
on the other hand, when the applied mROC discriminating rule has those coefficients and threshold determined for each of the 1000 subpopulations ("optimized coefficients" or "coef optim");
cf. Example 3 above.

The value of the correct classification rate is the value of the percentage of correctly classified patients.

The AUC value is the value of the area under the ROC curve.

The variability between the AUC obtained with the mROC rule of "fix coefficients" ("coef fix") and the AUC obtained with the mROC rule of "optimized coefficients" ("coef optim") was determined (FIG. 15).

FIG. 15 presents the histogram of AUC for the combination of HA+CXCL10 in Bootstrap (B=1000) with fix coefficients ("coef fix") [abscissa: 0.84; 0.86; 0.88; 0.90; 0.92; 0.94; 0.96]. FIG. 17 demonstrates that for 1000 different populations, the performances of the combination HA+CXCL10 are robust (values of AUC within a range of 0.84 to 0.96, which are high performances).

In addition, it has been noted that the performances in terms of AUC are similar irrespective of whether the mROC rule with "fix coefficients" ("coef fix") [coefficients fixed from the initial population of 310 patients and applied to each of the bootstrap subpopulations] is used, or whether the mROC rule with "optimized coefficients" ("coef optim") [coefficients of the mROC rule optimized for each of the 1000 bootstrap subpopulations] is used.

The performances of the mROC function obtained on the population of 118 patients of Example 1 (markers HA+CXCL10; function $Z_1$; cf. Table 2 above) were compared to those of the mROC function obtained on the population of 310 patients of Example 3 (markers HA+CXCL10; function $Z_4$; cf. Table 7 above) when they are both applied to the population of 118 patients.

The results of this comparison are shown in FIGS. 16A and 16B.

FIG. 16A: ordinate, function Z1 of Example 1 [Z=(0.3686)×CXCL10′+(0.3064)×HA′, with $\lambda_{CXCL10}$=−0.013 and λHA=0.099]; abscissa, function Z4 of Example 3 [Z=(1.999)×CXCL10′+(2.852)×HA′, with $\lambda_{CXCL10}$=−0.116 and λHA=−0.288].

FIG. 16B. ordinate, sensitivity; abscissa, specificity; curves of Z1 and Z4.

The transfer of the rule obtained from the population of 310 patients (function $Z_4$) onto the population of 118 patients allows to obtain AUCs similar to those obtained with the coefficients optimized on this population (function $Z_1$). Thus, it could be noted that in spite of a large difference of coefficients, the two scores are much correlated, and the ROC curves are close to one another. The differences of sensitivity and specificity are essentially explained by the threshold that also originates from the population of 310 patients. It would be perfectly possible to determine a threshold allowing similar performances to be obtained.

Example 10: Combination of HA with CXCL10 in Multiplex Mode

High throughput screening microplates are used. These are 96-well microplates of polystyrene LUMITRAC™ 600 (F bottom, "high binding", chimney wells, maximum theoretical volume of a well=392 µL), available from GREINER BIO-ONE GmbH; Maybachstrasse 2; DE 72636 Frickenhausen; Germany (catalogue reference 655 097).

By means of a spotter robot, rows of spots are deposited on the bottom of each well (spot=droplet of about 50 nL). Each spot contains a capture ligand, namely either an anti-human CXCL10 capture ligand or an anti-human HA capture ligand. The capture ligand bonds to the surface of the well.

The anti-human CXCL10 capture ligand is a mouse monoclonal anti-human CXCL10 antibody commercially available from R&D SYSTEMS, Inc. (614 McKinley Place NE; Minneapolis, Minn. 55413; USA) under the catalogue reference MAB266 (clone 33036, class IgG1).

The anti-human HA capture ligand is a recombinant human protein aggrecan protein G1-IGD-G2 commercially available from the company R&D SYSTEMS, Inc. (614 McKinley Place NE; Minneapolis, Minn. 55413; USA) under the catalogue reference 1220-PG-025.

The samples are serum or plasma samples from patients infected by HCV. They originate from the hospital Haut-Levêque (1, avenue Magellan; 33600 Pessac; France) or from the hospital Beaujon (100, boulevard du Général Leclerc; 92110 Clichy; France). The patients include, for example, patients of Example 3 or Example 1.

A standard range of CXCL10 was prepared by diluting a recombinant CXCL10 protein (PEPROTECH; Princeton Business Park; 5 Crescent Avenue; P.O. Box 275; Rocky Hill, N.J. 08553; USA; reference catalogue 300–12) in a PBS buffer solution (phosphate buffered saline) at pH 7.4 containing bovine serum albumin at 5%, glycerol at 20%, and a preservative at 0.1% (PROCLIN® 300; product SUPELCO commercially available from SIGMA-ALDRICH CHIMIE; 38297 Saint-Quentin-Fallavier CEDEX; France).

A standard range of HA was prepared by diluting a recombinant human hyaluronic acid (R&D SYSTEMS; Minneapolis; USA) in a PBS buffer solution at pH 7.4 containing bovine serum albumin at 5%, glycerol at 20%, and the preservative PROCLIN® 300 at 0.1%.

In each well of the microplate, there are successively distributed (on each spot): 40 µL of the PBS buffer solution at pH 7.4 containing bovine serum albumin at 5%, glycerol at 20%, and the preservative PROCLIN® 300 at 0.1%; and 40 µL of sample to be analyzed, or of a solution of the CXCL10 standard range, or of a solution of the HA standard range.

The mixture is incubated at 37° C. with stirring for 40 min.

Three successive washes are realized, each with at least 400 µL of a washing solution (buffer solution TRIS 10 mM at pH 7.4 containing NaCl 218 mM, TWEEN® 20 (SIGMA-ALDRICH CHIMIE; 38297 Saint-Quentin-Fallavier CEDEX; France; catalogue reference 2287) at 0.1%, and the preservative PROCLIN® 300 at 0.002%.

Into each reaction well, there are subsequently distributed (onto each spot) 50 µL of a PBS buffer solution 10 mM at pH 7.4 containing NaCl at 150 mM, glycerol at 10%, mouse IgG (MERIDIAN LIFE SCIENCE, Inc.; 5171 Wilfong Road; Memphis Tenn. 38134; USA; catalogue reference A66185M) at 50 g/L, the preservative PROCLIN® 300 at 0.1%, as well as a ligand for the detection of human CXCL10 at a concentration of 0.2 µg/mL, and a ligand of human HA at a concentration of 0.2 to 0.5 µg/mL.

The ligand for the detection of CXCL10 is a biotin-coupled goat polyclonal anti-human CXCL10 antibody available from R&D SYSTEMS, Inc. (614 McKinley Place NE; Minneapolis, Minn. 55413; USA; catalogue reference BAF266).

The ligand for the detection of human HA is the biotin-coupled recombinant protein aggrecan G1-IGD-G2 available from R&D SYSTEMS, Inc. (614 McKinley Place NE; Minneapolis, Minn. 55413; USA, under the catalogue reference 1220-PG-025.

The mixture is incubated at 37° C. with stirring for 15 min.

Three successive washes are realized, each with at least 400 µL of a washing solution (buffer solution TRIS 10 mM at pH 7.4 containing NaCl 218 mM, TWEEN® 20 (SIGMA-ALDRICH CHIMIE; 38297 Saint-Quentin-Fallavier CEDEX; France; catalogue reference 2287) at 0.1%, and the preservative PROCLIN® 300 at 0.002%.

Into each reaction well, there is subsequently distributed the reporter, namely (onto each spot) 50 µL of a citrate buffer solution 50 mM, pH 6.7, containing NaCl 150 mM, EDTA 5.6 mM, TRITON® 2%, sheep serum 10%, mouse IgG 500 µg/mL, the preservative PROCLIN® 300 0.5%, cow's milk (100% skimmed) 15%, glycerol 10%, $NaN_3$ 0.095%) and further containing streptavidin coupled to horseradish peroxydase (streptavidin-POD, available from ROCHE DIAGNOSTICS GmbH; Roche Applied Science; 68298 Mannheim; Germany; catalogue reference 11089153001) (cf. Nakane and Kawaoi 1974) at 3 µg/mL.

The mixture is incubated at 37° C. with stirring for 15 min.

Into each reaction well, there are subsequently distributed the substrate for the development of the chemiluminescence reactions, namely (onto each spot) 25 µL of enhancer solution/luminol XLSE024L and 25 µM solution of the peroxide XLSE024P [25 µL of solution (A) and 25 µL of solution (B) of ELISTAR ETA C Ultra ELISA, commercially available from CYANAGEN; Via degli Stradelli Guelfi 40/C; 40138 Bologna; Italy; catalogue reference XLSE024.0020].

The mixture is incubated at 37° C. with stirring for 1 min.

The acquisition of the luminescence signal is realized during 180 seconds.

The results of the readings are directly treated by an image analyzing system and registered in relative luminescence units or relative light units (RLU).

For the interpretation of the results, the concentration of biomarkers CXCL10 and HA is recalculated for each sample by means of the recombinant CXCL10 standard range for CXCL10 in pg/mL and of the recombinant HA standard range for HA in ng/mL.

Alternatively, the ligand for the detection of human CXCL10 and the ligand for human HA cannot be placed each in different spots, but on the contrary both in the same spot. In this case, the detection is realized by differentiating the bonded CXCL10 molecules from the bonded HA molecules, for example, not in chemiluminescence, but in fluorescence (by means of two different fluorophores, one borne by the CXCL10 detection ligand, the other one borne by the HA detection ligand).

BIBLIOGRAPHICAL REFERENCES

Adam et al. 2005. Clinical. Chemistry 51(10): 1867-1873.
Anastasiadis et al. 2005; *New globally convergent training scheme based on the resilient propagation algorithm.* Neurocomputing 64; 253-270.
Berkson 1944. *Application of the Logistic Function to Bio-Easy*, Journal of the American Statistical Association, volume 39, pages 357-365.
Berkson 1951. *Why I Prefer Logits to Probits*. Biometrics, vol., 7, 1951, p. 327-329.
Booth et al. 2002. Biochemistry 41 (33): 10418-10425.
Boursier et al. 2012. Hepatology 55(1): 58-67.
Box et Cox 1964. *An analysis of transformations*. Journal of the Royal Statistical Society, Series B 26; 211-243,
Breiman Friedman, Stone et Olshen 1984. *Classification and regression trees*. Monterey, Calif.: Wadsworth & Brooks/Cole Advanced Books & Software. ISBN 978-0-412-04841-8.
Breiman 2001; *Random Forests*. Machine Learning 45:5-32.
Castera et al. 2005. Gastroenterology 128: 343-350.
Castera et al. 2010. Journal of Hepatology 52: 191-198.
Castera et al. 2014. Comparison of transient elastography (*Fibroscan*), Fibrotest, APRI and two algorithms combining these non-invasive tests for liver fibrosis staging in HIV/HCV coninfected patients: ANRS CO13 HEPAVIH and FIBROSTIC collaboration. HIV Medicine 15(1):30-39.
Castera 2012. Gastroenterology 142; 1293-1302.
Chambers 2008; *Software for data analysis: programming with R*. Springer, New York, ISBN 978-0-387-75935-7.
Efron 1979. *Bootstrap Methods: Another Look at the Jacknife*. Annals of Statistics, volume no. 7, no. 1, pages 1-26.
Falissard 2005; *Comprendre et utiliser les statistiques dans les sciences de la vie*, Masson.
Forms et al. 2002. Hepatology 36: 986-992.
Goodman 2007. Journal of Hepatology 47: 598-607.
Hastle, Tibishirani et Friedman, 2009; "*The Elements of Statistical Learning: Data Mining, Inference and Predication*", $2^{nd}$ Edition, Springer.
Imbert-Bismut et al. 2001. The Lancet 357: 1069-1075.
Intrator et Intrator 1993; *Using Neural Nets for Interpretation of Nonlinear Models*. Proceedings of the Statistical Computing Section, San Francisco: American Statistical Society (eds), pages 244-249.
Kelleher et al. 2005. Journal of Hepatology 43; 78-84.
Kramar et al. 1999; *Critéres ROC généralisés pour l'évaluation de plusieurs marqueurs tumoraux*. Revue d'Epidémiologie et Santé Publique 47: 376-383.
Kramar et al. 2001. *mROC: a computer program for combining tumour markers in predicting disease states*. Computer methods and programs in biomedicine 66: 199-207.
Liaw et Wiener 2002; *Classification and regression by Random Forest*. R. News 23: 18-22.
Nakane et Kawaol 1974. J. Histochem. Cytochem. 22(12): 1084-1091.
Reiser et Faraggi 1997; *Confidence intervals for the generalized ROC criterion*. Biometrics 53: 644-652.
Riedmiller 1994; *Rprop—Description and Implementation Details*. Technical Report. University of Karlsruhe.
Riedmiller et Braun 1993; *A direct adaptive method for faster backpropagation learning: the RPROP algorithm*. Proceedings of the IEEE International Conference on Neural Networks (ICNN), San Francisco, pages 586-591.
Shapiro 1999; *The interpretation of diagnostic tests*. Statistical Methods in Medical Research, 8: 113-134.
Su et Liu 1993; *Linear combinations of multiple diagnostic markers*. Journal of the American Statistical Association 88: 1350-1355.
Swaminathan et al. 2003. Structure 11(5):521-532.
Theodoridis et Koutroumbos 2009; Pattern Recognition. Academic Press, Elsevier.
Wai et al. 2003. Hepatology 38: 518-526.
Zerenski et al. 2009. The Journal of Infectious Diseases 200: 1774-1780.
U.S. Pat. No. 7,141,380 B2
US 2007/0225919 A1
U.S. Pat. No. 6,986,995 B2
U.S. Pat. No. 8,489,335 B2

---

The invention claimed is:

1. An article of manufacture for the multiplex detection of molecules contained in acellular form in a biological fluid comprising a solid support to which the ligands of said molecules are attached, in which the ligands of said molecules comprise:
   a first protein that specifically binds to hyaluronic acid (HA); and
   a second protein that specifically binds to C-X-C motif chemokine ligand 10 (CXCL10).

2. The article of manufacture according to claim 1, in which said solid support is a plate or microplate with wells, a chip made of silicon, a glass capillary, a glass slide, magnetic beads, or a membrane.

3. The article of manufacture according to claim 1, wherein the first protein is an antibody that binds to HA and the second protein is an antibody that binds to CXCL10.

4. A composition for the multiplex detection of molecules contained in acellular form in a biological fluid, comprising a mixture of the ligands of said molecules, in which the ligands of said molecules comprise:
   a first protein that specifically binds to HA and bears a first detection marker; and
   a second protein that specifically binds to CXCL10 and bears a second detection marker;
   in which said first detection marker is different from said second detection marker.

5. The composition according to claim 4, wherein the first protein is an antibody that binds to HA and the second protein is an antibody that binds to CXCL10.

6. A kit comprising nucleic acids that bind specifically to one or more hepatitis viruses, the kit further comprising ligands that bind to molecules contained in acellular form in a biological fluid, said ligands contained in the kit in a combined preparation for simultaneous use, said ligands comprise:
   a first protein that specifically binds to HA and bears a first detection marker; and
   a second protein that specifically binds to CXCL10 and bears a second detection marker;
   in which said second detection marker is different from said first detection marker.

7. The kit according to claim 6, further comprising an article of manufacture for the multiplex detection of molecules contained in acellular form in a biological fluid, the article of manufacture comprising a solid support to which the ligands of said molecules are attached.

8. The kit according to claim 6, further comprising an article of manufacture for multiplex detection of molecules contained in acellular form in a biological fluid, the article of manufacture comprising a solid support to which the ligands of said molecules are attached, wherein the solid support is a plate or microplate with wells, a chip made of silicon, a glass capillary, a glass slide, magnetic beads, or a membrane.

9. The kit according to claim 6, wherein the first protein is an antibody that binds to HA and the second protein is an antibody that binds to CXCL10.

* * * * *

SEQUENCE LISTING

```
<160> NUMBER OF SEQ ID NOS: 9

<210> SEQ ID NO 1
<211> LENGTH: 98
<212> TYPE: PRT
<213> ORGANISM: Homo sapiens

<400> SEQUENCE: 1

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80
```

Ala Ile Lys Asn Leu Leu Lys Ala Val Ser Lys Glu Arg Ser Lys Arg
                85                  90                  95

Ser Pro

<210> SEQ ID NO 2
<211> LENGTH: 98
<212> TYPE: PRT
<213> ORGANISM: Homo sapiens

<400> SEQUENCE: 2

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
                20                  25                  30

Ile Ser Ile Ser Asn Gln Pro Val Asn Pro Arg Ser Leu Glu Lys Leu
            35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Met Ser Lys Arg
                85                  90                  95

Ser Pro

<210> SEQ ID NO 3
<211> LENGTH: 21
<212> TYPE: PRT
<213> ORGANISM: Homo sapiens

<400> SEQUENCE: 3

Met Asn Gln Thr Ala Ile Leu Ile Cys Cys Leu Ile Phe Leu Thr Leu
1               5                   10                  15

Ser Gly Ile Gln Gly
                20

<210> SEQ ID NO 4
<211> LENGTH: 77
<212> TYPE: PRT
<213> ORGANISM: Homo sapiens

<400> SEQUENCE: 4

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
                20                  25                  30

Ser Gln Phe Cys Pro Arg Val Glu Ile Ile Ala Thr Met Lys Lys Lys
            35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro
65                  70                  75

<210> SEQ ID NO 5
<211> LENGTH: 77
<212> TYPE: PRT
<213> ORGANISM: Homo sapiens

-continued

<400> SEQUENCE: 5

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Met Ser Lys Arg Ser Pro
65                  70                  75

<210> SEQ ID NO 6
<211> LENGTH: 75
<212> TYPE: PRT
<213> ORGANISM: Homo sapiens

<400> SEQUENCE: 6

Leu Ser Arg Thr Val Arg Cys Thr Cys Ile Ser Ile Ser Asn Gln Pro
1               5                   10                  15

Val Asn Pro Arg Ser Leu Glu Lys Leu Glu Ile Ile Pro Ala Ser Gln
            20                  25                  30

Phe Cys Pro Arg Val Glu Ile Ile Ala Thr Met Lys Lys Lys Gly Glu
        35                  40                  45

Lys Arg Cys Leu Asn Pro Glu Ser Lys Ala Ile Lys Asn Leu Leu Lys
    50                  55                  60

Ala Val Ser Lys Glu Arg Ser Lys Arg Ser Pro
65                  70                  75

<210> SEQ ID NO 7
<211> LENGTH: 75
<212> TYPE: PRT
<213> ORGANISM: Homo sapiens

<400> SEQUENCE: 7

Leu Ser Arg Thr Val Arg Cys Thr Cys Ile Ser Ile Ser Asn Gln Pro
1               5                   10                  15

Val Asn Pro Arg Ser Leu Glu Lys Leu Glu Ile Ile Pro Ala Ser Gln
            20                  25                  30

Phe Cys Pro Arg Val Glu Ile Ile Ala Thr Met Lys Lys Lys Gly Glu
        35                  40                  45

Lys Arg Cys Leu Asn Pro Glu Ser Lys Ala Ile Lys Asn Leu Leu Lys
    50                  55                  60

Ala Val Ser Lys Glu Met Ser Lys Arg Ser Pro
65                  70                  75

<210> SEQ ID NO 8
<211> LENGTH: 73
<212> TYPE: PRT
<213> ORGANISM: Homo sapiens

<400> SEQUENCE: 8

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

```
Gly Glu Lys Arg Cys Leu Asn Pro Glu Ser Lys Ala Ile Lys Asn Leu
    50                  55                  60

Leu Lys Ala Val Ser Lys Glu Arg Ser
65                  70

<210> SEQ ID NO 9
<211> LENGTH: 73
<212> TYPE: PRT
<213> ORGANISM: Homo sapiens

<400> SEQUENCE: 9

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Met Ser
65                  70
```